US011324858B2

(12) United States Patent
Chen et al.

(10) Patent No.: US 11,324,858 B2
(45) Date of Patent: May 10, 2022

(54) BIOMATERIALS FOR ENHANCED IMPLANT-HOST INTEGRATION

(71) Applicants: Massachusetts Institute of Technology, Cambridge, MA (US); The Trustees of the University of Pennsylvania, Philadelphia, PA (US)

(72) Inventors: Christopher S. Chen, Newton, MA (US); Jan D. Baranski, Philadelphia, PA (US); Ritika Chaturvedi, Philadelphia, PA (US); Michael T. Yang, West Windsor, NJ (US); Kelly R. Stevens, Seattle, WA (US); Sangeeta N. Bhatia, Lexington, MA (US)

(73) Assignees: The Trustees of the University of Pennsylvania, Philadelphia, PA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/213,423

(22) Filed: Mar. 26, 2021

(65) Prior Publication Data
US 2021/0213171 A1 Jul. 15, 2021

Related U.S. Application Data

(60) Division of application No. 16/589,768, filed on Oct. 1, 2019, which is a division of application No. 14/593,555, filed on Jan. 9, 2015, now Pat. No. 10,426,870, which is a continuation of application No. PCT/US2013/049933, filed on Jul. 10, 2013.

(60) Provisional application No. 61/670,100, filed on Jul. 10, 2012.

(51) Int. Cl.
| *A61K 35/44* | (2015.01) |
| *A61L 27/50* | (2006.01) |
| *A61L 27/36* | (2006.01) |
| *A61L 27/38* | (2006.01) |
| *A61L 27/22* | (2006.01) |
| *A61L 27/24* | (2006.01) |
| *A61L 27/40* | (2006.01) |

(52) U.S. Cl.
CPC .............. *A61L 27/50* (2013.01); *A61K 35/44* (2013.01); *A61L 27/225* (2013.01); *A61L 27/24* (2013.01); *A61L 27/3604* (2013.01); *A61L 27/3804* (2013.01); *A61L 27/3808* (2013.01); *A61L 27/3834* (2013.01); *A61L 27/3839* (2013.01); *A61L 27/3886* (2013.01); *A61L 27/40* (2013.01); *A61L 27/507* (2013.01); *A61L 2430/20* (2013.01); *A61L 2430/28* (2013.01)

(58) Field of Classification Search
CPC ............... A61L 27/507; A61L 27/3839; A61L 27/3604; A61L 27/24; A61L 27/3808; A61K 35/44
See application file for complete search history.

(56) References Cited

U.S. PATENT DOCUMENTS

| 4,853,332 | A | 8/1989 | Mark et al. |
| 5,116,964 | A | 5/1992 | Capon et al. |
| 5,123,950 | A | 6/1992 | Homma et al. |
| 5,624,840 | A | 4/1997 | Naughton et al. |
| 5,712,161 | A | 1/1998 | Koezuka et al. |
| 6,368,612 | B1 | 4/2002 | Lanza et al. |
| 6,509,514 | B1 | 1/2003 | Kneteman et al. |
| 6,864,402 | B1 | 3/2005 | Rogier et al. |
| 6,995,299 | B2 | 2/2006 | Wu et al. |
| 7,273,963 | B2 | 9/2007 | Kneteman et al. |
| 7,498,479 | B2 | 3/2009 | Kneteman et al. |
| 7,626,075 | B2 | 12/2009 | Beschorner et al. |
| 8,852,932 | B2 | 10/2014 | Forgacs et al. |
| 10,004,826 | B2 | 6/2018 | Bhatia et al. |
| 10,072,257 | B2 | 9/2018 | Bhatia et al. |
| 10,260,039 | B2 | 4/2019 | Bhatia et al. |
| 10,426,870 | B2 | 10/2019 | Chen et al. |
| 2002/0182633 | A1 | 12/2002 | Chen et al. |
| 2003/0203003 | A1 | 10/2003 | Nelson et al. |
| 2004/0096966 | A1 | 5/2004 | Ingram |
| 2004/0121066 | A1 | 6/2004 | Anderson, Jr. et al. |
| 2004/0126405 | A1 | 7/2004 | Sahatijan et al. |
| 2005/0053642 | A1 | 3/2005 | Ulbricht et al. |
| 2005/0169962 | A1 | 8/2005 | Bhatia et al. |
| 2006/0258000 | A1 | 11/2006 | Allen et al. |

(Continued)

FOREIGN PATENT DOCUMENTS

| EP | 1083945 A1 | 3/2001 |
| EP | 1500697 A2 | 1/2005 |

(Continued)

OTHER PUBLICATIONS

Raghavan et al., Geometrically controlled endothelial tubulogenesis in micropatterned gels. Tissue Engineering Part A, vol. 16, No. 7 (Jul. 2010) pp. 2255-2263. (Year: 2010).*
Abu-Absi, S. F. et al., "Structural polarity and functional bile canaliculi in rat hepatocyte spheroids," Exp Cell Res., vol. 274(1):56-67 (2002.
Aird, W. C., "Endothelium in health and disease," Pharmacol Rep. vol. 60 (1):139-143 (2008).

(Continued)

*Primary Examiner* — Kara D Johnson
(74) *Attorney, Agent, or Firm* — McCarter & English, LLP

(57) ABSTRACT

The present disclosure provides patterned biomaterials having organized cords and extracellular matrix embedded in a 3D scaffold. According, the present disclosure provides compositions and applications for patterned biomaterials. Pre-patterning of these biomaterials can lead to enhanced integration of these materials into host organisms, providing a strategy for enhancing the viability of engineered tissues by promoting vascularization.

20 Claims, 26 Drawing Sheets

(56) References Cited

U.S. PATENT DOCUMENTS

| | | |
|---|---|---|
| 2006/0270032 A1 | 11/2006 | Bhatia et al. |
| 2008/0075750 A1 | 3/2008 | Akins |
| 2008/0226604 A9 | 9/2008 | Kellar et al. |
| 2008/0280360 A1 | 11/2008 | Kaplan et al. |
| 2009/0018033 A1 | 1/2009 | Morgan et al. |
| 2009/0035855 A1 | 2/2009 | Ying et al. |
| 2009/0117655 A1 | 5/2009 | Kubota et al. |
| 2009/0285892 A1 | 11/2009 | Sakthivel |
| 2009/0319033 A1 | 12/2009 | Niklason et al. |
| 2010/0040584 A1* | 2/2010 | Melero-Martin ... A61L 27/3804 424/93.7 |
| 2010/0099048 A1 | 4/2010 | Thomas et al. |
| 2010/0168872 A1 | 7/2010 | Brown et al. |
| 2010/0184220 A1 | 7/2010 | Ram-Liebig et al. |
| 2010/0189712 A1 | 7/2010 | L'Heureux et al. |
| 2010/0278798 A1 | 11/2010 | Sia et al. |
| 2010/0285094 A1 | 11/2010 | Gupta |
| 2011/0035024 A1 | 2/2011 | Malmquist et al. |
| 2012/0141547 A1 | 6/2012 | Zhao et al. |
| 2012/0216304 A1 | 8/2012 | Bhatia et al. |
| 2014/0212910 A1 | 7/2014 | Bhatia et al. |
| 2015/0082468 A1 | 3/2015 | Bhatia et al. |
| 2015/0087004 A1 | 3/2015 | Chen et al. |
| 2015/0125507 A1 | 5/2015 | Chen et al. |
| 2019/0076578 A1 | 3/2019 | Bhatia et al. |
| 2019/0376024 A1 | 12/2019 | Bhatia et al. |
| 2020/0101201 A1 | 4/2020 | Chen et al. |

FOREIGN PATENT DOCUMENTS

| | | |
|---|---|---|
| EP | 1939280 A1 | 7/2008 |
| WO | 94/08570 A1 | 4/1994 |
| WO | 9952573 A1 | 10/1999 |
| WO | 2004/046337 A2 | 6/2004 |
| WO | 2006001778 A1 | 1/2006 |
| WO | 08/148026 A1 | 12/2008 |
| WO | 2012/048170 A2 | 4/2012 |
| WO | 2014/011775 A1 | 1/2014 |

OTHER PUBLICATIONS

Akselrod, G. M. et al., "Laser-guided assembly of heterotypic three-dimensional living cell microarrays," Biophys J., vol. 91 (1): 3465-3473 (2006).

Albrecht, D. R., et al."Probing the role of multicellular organization in three-dimensional microenvironments," Nat Methods, vol. 3(5): 369-375 (2006).

Antonchuk, J. et al., "AggreWell 400 and AggreWell 800 Provide a Unique Platform for Generation of Size-Controlled Aggregates Including Human Embryoid Bodies," STEMCell Technologies, Poster Presentation, 1 page (2010).

Arcaute, K. et al., "Stereolithography of three-dimensional bioactive poly(ethylene glycol) constructs with encapsulated cells," Annals of Biomedical Engineering, vol. 34(9):1429-1441 (2006).

Atala, A., "Engineering organs," Curr Opin Biotechnol., vol. 20(5):575-592 (2009).

Au, P., et al., Bone marrow-derived mesenchymal stem cells facilitate engineering of long-lasting functional vasculature. Blood, 2008. 111(9): p. 4551-4558.

Azuma, Hisaya et al., "Robust expansion of human hepatocytes in Fah-/-/Rag2-/-/Il2rg-/- mice," Nature Biotechnology, vol. 25(8):903-910 (2007).

Baranski, J. et al., "Geometric control of vascular networks to enhance engineered tissue in-tegration and function," PNAS, vol. 110(19): 7586-7591 (2013).

Barron, J. A, et al., "Biological laser printing: a novel technique for creating heterogeneous 3-dimensional cell patterns," Biomed Microdevices, vol. 6 (2):139-147 (2004).

Baudin et al. A protocol for isolation and culture of human umbilical vein endothelial cells. Nature Protocols, vol. 2(3):481-485 (2007).

Berry, M.N., et al., "High-yield preparation of isolated rat liver parenchymal cells: a biochemical and fine structural study," J. Cell Biol., vol. 43(3), pp. 506-520 (1969).

Glicklis, R., et al., "Hepatocyte behavior within three-dimensional porous alginate scaffolds," Biotechnol Bioeng., vol. 67(3), 344-353 (2000).

Hamada, H., "In search of Turing in vivo: understanding Nodal and Lefty behavior," Dev Cell, vol. 22(5): 911-912 (2012).

Bhatia, S.N. et al., "Effect of cell-cell interactions in preservation of cellular phenotype: cocultivation of hepatocytes and nonparenchymal cells," FASEB J., vol. 13:1883-1900 (1999).

Brophy, C. M. et al."Rat hepatocyte spheroids formed by rocked technique maintain differentiated hepatocyte gene expression and function," Hepatology vol. 49(2):578-586 (2009).

Cao, X. et al., "Differentiation and Functional Comparison of Monocytes and Macrophages from hiPSCs with Peripheral Blood Derivatives," Stem Cell Reports, vol. 12(6): 1282-1297 (2019).

Chan, V. et al., "Three-dimensional photopatterning of hydrogels using stereolithography for long-term cell encapsulation," Lab Chip, vol. 10: 2062-2070 (2010).

Chen, A. A., et al., "Humanized mice with ectopic artificial liver tissues," Proc Natl Acad Sci USA, vol. 108(29):11842-11847 (2011).

He, J. Q. et al., "Human embryonic stem cells develop into multiple types of cardiac myocytes: action potential characterization," Circ Res., vol. 93(1): 32-39 (2003).

Chen, et al., "Spatio-temporal VEGF and PDGF delivery patterns blood vessel formation and maturation" Pharm Res 24(2):258-264. (2007).

Chen, et al. (2009) Prevascularization of a fibrin-based tissue construct accelerates the formation of functional anastomosis with host vasculature. Tissue Eng Part A 15(6):1363-1371.

Chen, et al. (2010) Rapid anastomosis of endothelial progenitor cell-derived vessels with host vasculature is promoted by a high density of cotransplanted fibroblasts. Tissue Eng Part A 16(2):585-594.

Harding, et al., "An Implantable Vascularized Protein Gel Construct That Supports Human Fetal Hepatoblast Survival and Infection by Hepatitis C Virus in Mice" Plos One, 2010. 5(4).

Cheng, et al. (2011) Engineered blood vessel networks connect to host vasculature via wrapping-and-tapping anastomosis. Blood 118(17):4740-4749.

Cho, C. et al., "Layered patterning of hepatocytes in co-culture systems using microfabricated stencils," Biotechniques, vol. 48(1): 47-52 (2010).

Cho, N-M., et al., "Viral infection of human progenitor and liver-derived cells encapsulated in three-dimensional PEG-based hydrogel ," Biomedical Materials, vol. 4: 1-7 (2009).

Choi et al. "Patterning and transferring hydrogel-encapsulated bacterial cells for quantitative analysis of synthetically engineered genetic circuits." Biomaterials. Jan. 2012;33(2):624-33. doi: 10.1016/j.biomaterials.2011.09.069. Epub Oct. 19, 2011.

Cleaver, O.et al., "Endothelial signaling during development," Nat Med, vol. 9(6):661-668 (2003).

Culver, J. C., et al., "Three-dimensional biomimetic patterning in hydrogels to guide cellular organization," Adv Mater, vol. 24(17):2344-2348 (2012).

Database, U., National Organ transplant waiting list report, US Department of Health and Human Services.

Debbage, et al. (1998) Lectin intravital perfusion studies in tumor-bearing mice: Micrometer-resolution, wide-area mapping of microvascular labeling, distinguishing efficiently and inefficiently perfused microregions in the tumor. J HistochemCytochem 46(5):627-639.

Debbage, et al. (2001) Intravital lectin perfusion analysis of vascular permeability in human micro- and macro-blood vessels. Histochem Cell Biol 116(4):349-359.

DeForest, C. A., et al.,"Cytocompatible click-based hydrogels with dynamically tunable properties through orthogonal photoconjugation and photocleavage reactions," Nat Chem., vol. 3(12):925-931 (2011).

Ding, B. S. et al., "Endothelial-derived angiocrine signals induce and sustain regenerative lung alveolarization," Cell, vol. 147(3):539-553 (2011).

(56) References Cited

OTHER PUBLICATIONS

Ding, B. S. et al., "Inductive angiocrine signals from sinusoidal endothelium are required for liver regeneration," Nature, vol. 468(7321):310-315 (2010).
Douglas, E. et al., "Self-assembled cellular microarrays patterned using DNA barcodes," Lab on a Chip, vol. 7(11), 7 pages (2007).
Du, Y, et al., "Directed assembly of cell-laden microgels for fabrication of 3D tissue constructs," Proc Natl Acad Sci USA, vol. 105(28):9522-9527 (2008).
Dunn, J. C., et al., "Long-term in vitro function of adult hepatocytes in a collagen sandwich configuration," Biotechnol Prog., vol. 7(3):237-245 (1991).
Ennett, A. B. et al., "Tissue engineering strategies for in vivo neovascularisation," Expert Opin Biol Ther., vol. 2(8):805-818 (2002).
Folkman, "Looking for a good endothelial address" Cancer Cell 1(2):113-115. (2002).
Francipane, M. et al., "Maturation of embryonic tissues in a lymph node: a new approach for bioengineering complex organs," Organogenesis, vol. 10 (3):323-331(2014).
Franses, J. W., et al., "Stromal endothelial cells directly influence cancer progression," Sci Transl Med., vol. 3 (66):66ra5, 18 pages (2011).
Gartner, Z. J., et al. "Programmed assembly of 3-dimensional microtissues with defined cellular connectivity" PNAS, vol. 106(12), pp. 4606-4610 (2009).
Gjorevski, et al., "Endogenous patterns of mechanical stress are required for branching morphogenesis" Integrative Biology, 2010. 2(9): p. 424-434.
Hristov et al., "Endothelial Progenitor Cells: Mobilization, Differentiation, and Homing," Arterioscler. Thromb. Vasc. Biol. 23:1185-1189 (2003).
Hui, E. et al., "Micromechanical control of cell-cell interactions," Proc Natl Acad Sci USA, vol. 104(14):5722-5726 (2007).
Inman, J. L. et al., "Apical polarity in three-dimensional culture systems: where to now?," J. Biol., vol. 9(1): 2 (2010).
Intaglietta, et al., "Microvascular and tissue oxygen distribution" Cardiovasc Res 32(4):632-643. (1996).
International Preliminary Reporton Patentability for Application No. PCT/US2011/055179, 12 pages, dated Apr. 9, 2013.
International Preliminary Report on Patentability, PCT/US2012/037656, dated Nov. 12, 2013, 9 pages.
International Preliminary Report on Patentability, PCT/US2013/028345, dated Sep. 2, 2014, 6 pages.
International Preliminary Report on Patentability, PCT/US2016/055972, dated Apr. 10, 2018, 6 pages.
International Search Report and Written Opinion for Application No. PCT/US2011/055179, 17 pages, dated May 23, 2012.
International Search Report and Written Opinion, PCT/US2012/037656, dated Oct. 17, 2012, 9 pages.
International Search Report and Written Opinion, PCT/US2013/028345, dated May 24, 2013, 9 pages.
International Search Report and Written Opinion, PCT/US2016/055972, dated Oct. 10, 2017, 8 pages.
International Search Report dated Dec. 17, 2013 in International Application No. PCT/US13/49933.
Invitation to Pay Additional Fees, and, Where Applicable, Protest Fee for Application No. PCT/US2011/055179, 5 pages, dated Feb. 13, 2012.
Jain, "Transport of molecules, particles, and cells in solid tumors" Annu Rev Biomed Eng 1:241-263. (1999).
Jakab, K, et al., "Engineering biological structures of prescribed shape using self-assembling multicellular systems," Proc Natl Acad Sci USA, vol. 101(9):2864-2869 (2004).
Jakab, K., et al., "Tissue engineering by self-assembly and bio-printing of living cells," Biofabrication, vol. 2(2): 022001 (2010).
Kachouie, N. et al., "Directed assembly of cell-laden hydrogels for engineering functional tissues," Organogenesis, pp. 234-244 (2010) <URL:http://ukpmc.ac.uk/articles/PMC3055649 /pdf/org0604 0234.pdf> [retrieved on Oct. 2, 2012].

Kaji, H. et al., "Engineering systems for the generation of patterned co-cultures for control-ling cell-cell interactions," Biochim Biophys Acta, vol. 1810(3): 239-250 (2011).
Kaufman-Francis, et al., "Engineered vascular beds provide key signals to pancreatic hormone-producing cells" PLoS One 7(7):e40741 (2012).
Kaufmann, P.M. et al., "Highly Porous Polymer Matrices as a Three-dimensional Culture System for Hepatocytes," Cell Transplantation, vol. 6(5):463-468 (1997).
Khademhosseini, Ali et al., "Progress in Tissue Engineering," Scientific American, vol. 300:64-71 (2009).
Khetani, Salman R. et al., "Exploring Interactions Between Rat Hepatocytes and Nonparenchymal Cells Using Gene Expression Profiling," Hepatology, vol. 40:545-554 (2004).
Khetani, Salman R. et al., "Microscale culture of human liver cells for drug development," Nature Biotechnology, vol. 26(1):120-126 (2008).
Khetani, SR et al., "T-cadherin modulates hepatocyte functions in vitro," FASEB J vol. 22(11):3768-3775 (2008).
Mailleux, A. A., et al., "Lumen formation during mammary epithelial morphogenesis: insights from in vitro and in vivo models," Cell Cycle, vol. 7 (1) :57-62 (2008).
Kloxin, A. M., et al."Photodegradable hydrogels for dynamic tuning of physical and chemical properties," Science, vol. 324(5293): 59-63 (2009).
Kneser, Ulrich et al., "Long-term differentiated function of heterotopically transplanted hepatocytes on three-dimensional polymer matrices," J. Biomed. Mater. Res., vol. 47:494-503 (1999).
Koffler J, et al., "Improved vascular organization enhances functional integration of engineered skeletal muscle grafts" Proc Natl Acad Sci USA 108(36): 14789-14794 (2011).
Koike N, et al., "Tissue engineering: Creation of long-lasting blood vessels" Nature 428(6979):138-139 (2004).
Komori, J. et al., "the mouse lymph node as an ectopic transplantation site for multiple tis-sues," Nature Biotechnology, vol. 30(10):976-985 (2012).
Lammert, E., et al., "Induction of pancreatic differentiation by signals from blood vessels," Science, vol. 294(5542):564-567 (2001).
Lammert, E., et al., "Role of endothelial cells in early pancreas and liver development," Mech Dev., vol. 120(1): 59-64 (2003).
Landry, J., et al., "Spheroidal aggregate culture of rat liver cells: histotypic reorganization, biomatrix deposition, and maintenance of functional activities," J Cell Biol, vol. 101(3): 914-923 (1985).
Lang, H. et al., "Transplantation of Mouse Embryonic Stem Cells into the Cochlea of an Au-ditory-Neuropathy Animal Model: Effects of Timing after Injury," JARO, vol. 9: 225-240 (2008).
Laube, F. et al., "Re-programming of newt cardiomyocytes is induced by tissue regenera-tion," Journal of Cell Science, vol. 119 (22):4719-4729 (2006).
Lee, et al., "Controlled growth factor release from synthetic extracellular matrices" Nature 408(6815):998-1000 (2000).
Lee, H. et al., "Local Delivery of Basic Fibroblast Growth Factor Increases Both Angiogenesis and Engradtment of Hepatocytes in Tissue-Engineered Polymer Devices," Transplantation, vol. 73:1589-1593 (2002).
Leight et al., "Manipulation of 3D Cluster Size and Geometry by Release from 2D Micropatterns", Cellular and Molecular Bioengineering 5(3): 299-306 (Jun. 27, 2012).
Levenberg, Shulamit et al., "Engineering vascularized skeletal muscle tissue," Nature Biotechnology, vol. 23(7):879-884 (2005).
Li, C. et al. "DNA-templated assembly of droplet-derived PEG microtissues," Lab on a Chip, vol. 11(17), 9 pages ( 2011).
Li, G. et al., "The dose of growth factors influences the synergistic effect of vascular endothe-lial growth factor on bone morphogenetic protein 4-induced ectopic bone formation," Tissue Engineering, vol. 15(8) 2123-2133 (2009).
Liu, Valerie A. et al., "Three-Dimensional Photopatterning of Hydrogels Containing Living Cells," Biomedical Microdevices, vol. 4(4):257-266 (2002).
Lovett, et al., "Vascularization strategies for tissue engineering" Tissue Eng Part B Rev 15(3):353-370 (2009).

(56) References Cited

OTHER PUBLICATIONS

Lu, H. F. et al., "Three-dimensional co-culture of rat hepatocyte spheroids and NIH/3T3 fibroblasts enhances hepatocyte functional maintenance," Acta Biomater., vol. 1(4):399-410 (2005).
MacNeil, S., "Progress and opportunities for tissue-engineered skin," Nature vol. 445(7130):874-880 (2007).
Takebe, T. et al., "Vascularized and functional human liver from an iPSC-derived organ bud transplant," Nature, vol. 499: 481-485 (2013).
Tamai et al. Characterization of a Liver Organoid Tissue Composed of Hepatocytes and Fibroblasts in Dense Collagen Fibrils. Tissue Engineering Part A (2013), 19(21), 2527-2535. (2013).
Tan, W. et al., "Layer-by-layer microfluidics for biomimetic three-dimensional structures," Biomaterials, vol. 25(7-8):1355-1364, (2004).
Tateno, Chise et al., "Near Completely Humanized Liver in Mice Shows Human-Type Metabolic Responses to Drugs," American Journal of Pathology, vol. 165(3):901-912 (2004).
Tekin, H., et al., "Responsive micromolds for sequential patterning of hydrogel microstructures," J Am Chem Soc., vol. 133(33): 12944-12947 (2011).
Traktuev, et al., "Robust Functional Vascular Network Formation In Vivo by Cooperation of Adipose Progenitor and Endothelial Cells" Circulation Research, 2009. 104(12): p. 1410-U320.
Tsang, L. V. et al., "Three-dimensional tissue fabrication," Advanced Drug Delivery Reviews, Elsevier BV, Amsterdam, NL, vol. 56(11):1635-1647 (2004).
Tsang, L.V. et al., "Fabrication of 3D hepatic tissues by additive photopatterning of cellular hydrogels," FASEB J., vol. 21(3): 790-801 (2007).
Tsuda, Y. et al., "Cellular control of tissue architectures using a three-dimensional tissue fabrication technique," Biomaterials, vol. 28(33): 4939-4946 (2007).
Ulbricht, J. et al., "On the biodegradability of polyethylene glycol, polypeptoids and poly(2-oxazoline)s," Biomaterials, vol. 35:4848-4861 (2014).
Underhill, G. H. et al., "Assessment of hepatocellular function within PEG hydrogels," Biomaterials, vol. 28(2):256-270 (2007).
Ungrin, M. D., et al., :Reproducible, Ultra High-Throughput Formation of Multicellular Organization from Single Cell Suspension-Derived Human Embryonic Stem Cell Aggregates, PLoS One vol. 3 (2):e1565(2008).
Uyama, Shiro et al., "Hepatocyte Transplantation Using Biodegradable Matrices in Ascorbic Acid-deficient Rats: Comparison with Heterotopically Transplanted Liver Grafts," Transplantation, vol. 71(9):1226-1231 (2001).
Vacanti, "Tissue engineering and the road to whole organs" Br J Surg 99(4): 451-453. (2012).
Vacanti, "Tissue engineering: The design and fabrication of living replacement devices for surgical reconstruction and transplantation" Lancet 354(Suppl 1):SI32-SI34. (1999).
Valignat, M-P., et al., "Reversible self-assembly and directed assembly of DNA-linked micrometer-sized colloids," PNAS, vol. 1020(12), pp. 4225-4229 (2005).
Vanbuskirk, Kelley M. et al., "Preerythrocytic, live-attenuated Plasmodium falciparum vaccine candidates by design," PNAS, vol. 106(31):13004-13009 (2009).
Weber, et al., "Cell-Matrix Interactions Improve beta-Cell Survival and Insulin Secretion in Three-Dimensional Culture" Tissue Engineering Part A, 2008. 14(12): p. 1959-1968.
White, et al., "Longitudinal in vivo imaging to assess blood flow and oxygenation in implantable engineered tissues" Tissue Eng Part C Methods 18(9):697-709. (2012).
Williams, C. M. et al., "Autocrine-Controlled Formation and Function of Tissue-Like Aggregates by Primary Hepatocytes in Micropatterned Hydrogel Arrays," Tissue Eng Part A vol. 17 (7-8), 1055-1068 (2011).
Wong, S. F., et al., "Concave microwell based size-controllable hepatosphere as a three-dimensional liver tissue model," Biomaterials, vol. 32(32):8087-8096 (2011).

Wylie, R. G. et al., "Spatially controlled simultaneous patterning of multiple growth factors in three-dimensional hydrogels," Nat Mater., vol. 10 (10): 799-806 (2011).
Yokoyama, T. et al., "In Vivo Engineering of Metabolically Active Hepatic Tissues in a Neovascularized Subcutaneous Cavity," American Journal of Transplantation, vol. 6:50-59 (2006).
Zhang, S. C. et al., "In vitro differentiation of transplantable neural precursors from human embryonic stem cells," Nat Biotechnol., vol. 19(12): 1129-1133(2001).
Zhou, J. et al., "Neural cell injury microenvironment induces neural differentiation of human umbilical cord mesenchymal stem cells," Neural Regen Res., vol. 7(34): 2689-2697 (2012).
March, S., et al., "Microenvironmental regulation of the sinusoidal endothelial cell phenotype in vitro," Hepatology, vol. 50(3):920-928 (2009).
Matsumoto, K., "Liver organogenesis promoted by endothelial cells prior to vascular function," Science, vol. 294(5542):559-563 (2001).
Matsumura, T. et al., "Establishment of an immortalized human-liver endothelial cell line with SV40T and hTERT," Transplantation, vol. 77(9):1357-1365 (2004).
Maurice et al.,"Effects of Imidazole derivatives on cytochromes P450 from human hepatocytes in primary culture," FASEB J., 752-758. (1992).
McGuigan, et al., "Vascularized organoid engineered by modular assembly enables blood perfusion" Proc Natl Acad Sci USA 103(31):11461-11466. (2006).
Mei, J. et al., "Improved survival of fulminant liver failure by transplantation of microencap-sulated cryopreserved porcine hepatocytes in mice," Cell Transplantation, vol. 18:101-110 (2009).
Melero-Martin, et al., "Engineering robust and functional vascular networks in vivo with human adult and cord blood-derived progenitor cells" Circ Res 103(2): 194-202 (2008).
Mikos, A. G., et al., "Engineering Complex Tissues," Tissue Eng vol. 12 (12): 3307-3339(2006).
Miller, J. S., et al. "Rapid casting of patterned vascular networks for perfusable engineered three-dimensional tissues," Nat Mater., vol. 11(9): 768-774 (2012).
Mironov, V. et al., "Organ printing: tissue spheroids as building blocks," Biomaterials, vol. 30(12):2164-2174 (2009).
Mironov, V., et al., "Organ printing: computer-aided jet-based 3D tissue engineering.," Trends Biotechnol., vol. 21(4):157-161 (2003).
Mooney, et al., "Growing new organs" Scientific American, 1999. 280(4): p. 60-65.
Moscona, A., "Rotation-mediated histogenetic aggregation of dissociated cells. A quantifiable approach to cell interactions in vitro," Exp Cell Res., vol. 22:455-475 (1961).
Muller, P., et al., "Differential diffusivity of Nodal and Lefty underlies a reaction-diffusion patterning system," Science, vol. 336(6082): 721-724(2012).
Muller, P., et al., "Extracellular movement of signaling molecules," Dev Cell., vol. 21(1): 145-158 (2011).
Nahmias, Y., et al., "Integration of technologies for hepatic tissue engineering," Adv Biochem Eng Biotechnol., vol. 103:309-329 (2007).
Nahmias, Y., et al., "Laser-guided direct writing for three-dimensional tissue engineering," Biotechnol Bioeng., vol. 92(2):129-136 (2005).
Nelson, C. et al., "Microstructured extracellular matrices in tissue engineering and develop-ment," Current Opinion in Biotechnology, vol. 17:518-523 (2006).
Nelson, C. M., et al., "Tissue geometry determines sites of mammary branching morphogenesis in organotypic cultures," Science, vol. 314(5797): 298-300 (2006).
Nikkhah, M. et al., "Directed Endothelial Cell Morphogenesis in Micropatterned Gelatin Methacrylate Hydrogels," Biomaterials, vol. 33(35): 9009-9018. (2012).
Nikolova, et al., "The vascular basement membrane: A niche for insulin gene expression and beta cell proliferation" Developmental Cell, 2006. 10(3): p. 397-405.
Nomi, M. et al., "Principals of neovascularization for tissue engineering," Molecular Aspects of Med., vol. 23: 463-483 (2002).

(56) References Cited

OTHER PUBLICATIONS

Ohashi, Kazuo et al., "Liver Tissue Engineering at Extrahepatic Sites in Mice as a Potential New Therapy for Genetic Liver Diseases," Hepatology, vol. 41:132-140 (2005).
Panda, P. et al., Stop-flow lithography to generate cell-laden microgel particles, Lab in a Chip, vol. 8(7):1056-1061 (2008).
Parenteau, N. L., "Commercial development of cell-based therapeutics: strategic considerations along the drug to tissue spectrum," Regen Med., vol. 4(4): 601-611 (2009).
Partial Supplementary European Search Report dated Feb. 24, 2016 in EP Application No. 13817119.4.
Peshwa, M. V., et al., "Mechanistics of formation and ultrastructural evaluation of hepatocyte spheroids," In Vitro Cell Dev Biol Anim., vol. 32(4): 197-203 (1996).
Phelps, et al., "Engineering more than a cell: vascularization strategies in tissue engineering" Current Opinion in Biotechnology, 2010. 21(5): p. 704-709.
Pittman, "Influence of microvascular architecture on oxygen exchange in skeletal muscle" Microcirculation 2(1):1-18. (1995).
Qiu et al. "Generation of Uniformly Sized Alginate Microparticles for Cell Encapsulation by Using a Soft-Lithography Approach." Advanced Materials 19.12 (2007): 1603-1607.
Radisic, et al., "High-density seeding of myocyte cells for cardiac tissue engineering" Biotechnol Bioeng 82(4):403-414 (2003).
Raghavan, S., et al., "Geometrically controlled endothelial tubulogenesis in micropatterned gels," Tissue Eng Part A., vol. 16(7):2255-2263 (2010).
Rago, A. P., et al., "Encapsulated Arrays of Self-Assembled Microtissues: An Alternative to Spherical Microcapsules," Tissue Eng Part A 15, 387-395 (2009).
Ramanan, V. et al., "Engineered ectopic human livers organize and proliferate in vivo in re-sponse to regenerative cues," BMES, 1 page (2015).
Reid, et al., "Extracellular matrix gradients in the space of Disse: Relevance to liver biology" Hepatology 15(6):1198-1203 (1992).
Richardson, et al., "Polymeric system for dual growth factor delivery" Nat Biotechnol 19(11):1029-1034. (2001).
Roh, et al., "Tissue-engineered vascular grafts transform into mature blood vessels via an inflammation-mediated process of vascular remodeling" Proceedings of the National Academy of Sciences of the United States of America, 2010. 107(10): p. 4669-4674.
Rosmorduc, et al. "Hypoxia: A link between fibrogenesis, angiogenesis, and carcinogenesis in liver disease" Semin Liver Dis 30(3):258-270. (2010).
Sakai, Y., et al., "A new bioartificial liver using porcine hepatocyte spheroids in high-cell-density suspension perfusion culture: in vitro performance in synthesized culture medium and in 100% human plasma.," Cell Transplant, vol. 8(5):531-541 (1999).
Schwartz, R.E., et al., "Modeling hepatitis C virus infection using human induced pluripotent stem cells," Proc Natl Acad Sci USA, vol. 109(7):2544-2548 (2012).
Seglen, P. O., "Preparation of isolated rat liver cells," Methods Cell Biol., vol. 13: 29-83 (1976).
Seo, S. et al., "Enhanced liver functions of hepatocytes cocultured with NIH 3T3 in the algi-nate/galactosylated chitosan scaffold," Biomaterials, vol. 27: 1487-1495 (2007).
Si-Tayeb, K. et al., "Highly efficient generation of human hepatocyte-like cells from induced pluripotent stem cells," Hepatology, vol. 51(1): 297-305 (2010).
Smith, et al., "Locally enhanced angiogenesis promotes transplanted cell survival" Tissue Engineering, 2004. 10(1-2): p. 63-71.
Stevens KR, et al., "InVERT molding for scalable control of tissue microarchitecture," Nat Commun., vol. 4 (1847) doi:10.1038/ncomms2853 (2013).
Stevens, K. R et al., "Physiological function and transplantation of scaffold-free and vascularized human cardiac muscle tissue," Proc Natl Acad Sci USA., vol. 106(39): 16568-16573 (2009).
Stevens, Molly M. et al., "In vivo engineering of organs: The bone bioreactor," PNAS, vol. 102(32):11450-11455 (2005).
Takahashi K. et al., "Induction of pluripotent stem cells from mouse embryonic and adult fibroblast cultures by defined factors," Cell, vol. 126 (4): 663-676 (2006).
Takebe et al. Engineering of human hepatic tissue with functional vascular networks. Organogenesis (Apr. 2014), 10 (2), (2014).
Takebe, T. et al., "Generation of a vascularized and functional human liver from an iPSC-derived organ bud transplant," Nature Protocols, vol. 9 (2): 396-409 (2014).
U.S. Appl. No. 15/765,526, filed Apr. 3, 2018, Sangeeta N. Bhatia.
U.S. Appl. No. 17/213,436, filed Mar. 26, 2021, Sangeeta N. Bhatia.
U.S. Appl. No. 16/589,768, filed Oct. 1, 2019, Christopher S. Chen.
U.S. Appl. No. 14/593,555, filed Jan. 9, 2015, Christopher S. Chen.
U.S. Appl. No. 14/116,901, filed Apr. 14, 2014, Sangeeta N. Bhatia.
U.S. Appl. No. 16/358,160, filed Mar. 19, 2019, Sangeeta N. Bhatia.
U.S. Appl. No. 14/381,866, filed Aug. 28, 2014, Sangeeta N. Bhatia.
U.S. Appl. No. 13/267,866, filed Oct. 6, 2011, Sangeeta N. Bhatia.
U.S. Appl. No. 15/765,526, Mar. 12, 2021.
U.S. Appl. No. 15/765,526, Apr. 28, 2020.
U.S. Appl. No. 15/765,526, Aug. 28, 2019.
U.S. Appl. No. 15/765,526, May 29, 2019.
U.S. Appl. No. 14/593,555, Aug. 1, 2019.
U.S. Appl. No. 14/593,555, Nov. 26, 2018.
U.S. Appl. No. 14/593,555, Jun. 5, 2018.
U.S. Appl. No. 14/593,555, Jan. 12, 2018.
U.S. Appl. No. 14/593,555, Nov. 18, 2016..
U.S. Appl. No. 14/593,555, Aug. 29, 2016.
U.S. Appl. No. 14/116,901, Nov. 21, 2018.
U.S. Appl. No. 14/116,901, Mar. 9, 2018.
U.S. Appl. No. 14/116,901, Mar. 2, 2017.
U.S. Appl. No. 14/116,901, Jun. 17, 2016.
U.S. Appl. No. 14/116,901, Sep. 24, 2015.
U.S. Appl. No. 16/358,160, Mar. 25, 2021.
U.S. Appl. No. 16/358,160, Nov. 17, 2020.
U.S. Appl. No. 16/358,160, Jul. 22, 2020.
U.S. Appl. No. 16/358,160, May 17, 2018.
U.S. Appl. No. 14/381,866, Apr. 26, 2017.
U.S. Appl. No. 14/381,866, Jun. 30, 2016.
U.S. Appl. No. 14/381,866, Nov. 18, 2015.
U.S. Appl. No. 13/267,866, Mar. 8, 2018.
U.S. Appl. No. 13/267,866, Feb. 9, 2017.
U.S. Appl. No. 13/267,866, Mar. 21, 2016.
U.S. Appl. No. 13/267,866, Jul. 31, 2014.
U.S. Appl. No. 13/267,866, Aug. 5, 2013.
U.S. Appl. No. 13/267,866, Sep. 11, 2012.
Aubin et al., Directed 3D cell alignment and elongation in microengineered hydrogels. Biomaterials. Sep. 2010;31(27):6941-51.
Dickinson et al., Guiding endothelial progenitor cell tube formation using patterned fibronectin surfaces. Soft Matter. 2010;6:5109-19.
Hsiao et al., Direct cell surface modification with DNA for the capture of primary cells and the investigation of myotube formation on defined patterns. Langmuir. Jun. 1, 20096;25(12):6985-91.
Jeong et al., "Living" microvascular stamp for patterning of functional neovessels; orchestrated control of matrix property and geometry. Adv Mater. Jan. 3, 2012;24(1):58-63.
Kang et al., Bioengineered human vascular networks transplanted into secondary mice reconnect with the host vasculature and re-establish perfusion. Blood. Dec. 1, 20115,118(25):6718-21.
Omidan et al., Swelling and mechanical properties of modified hema-based superporous hydrogels. J Bioact Compat Polym. Sep. 2010;25:483-97.
Rnjak et al., Primary human dermal fibroblast interactions with open weave three-dimensional scaffolds prepared from synthetic human elastin. Biomaterials Nov. 2009;30(32):6469-77.

* cited by examiner

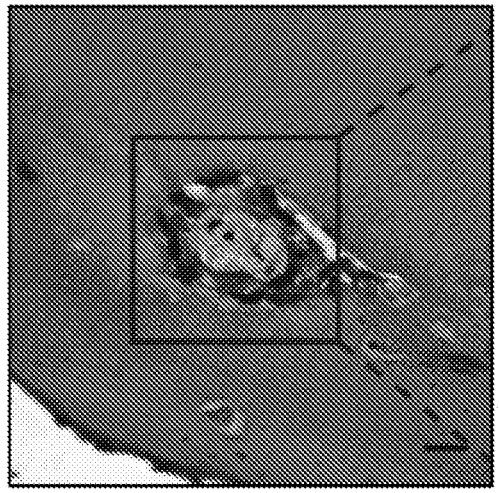 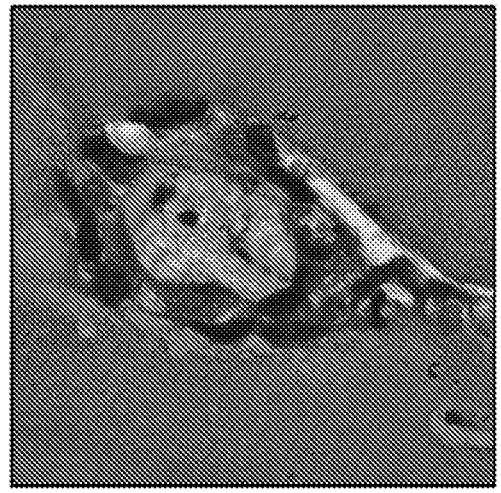
FIG. 1F
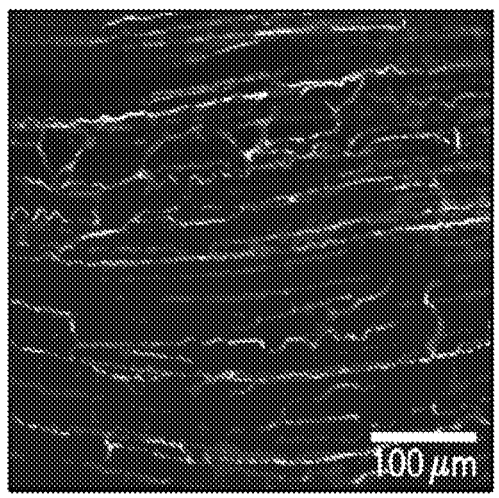 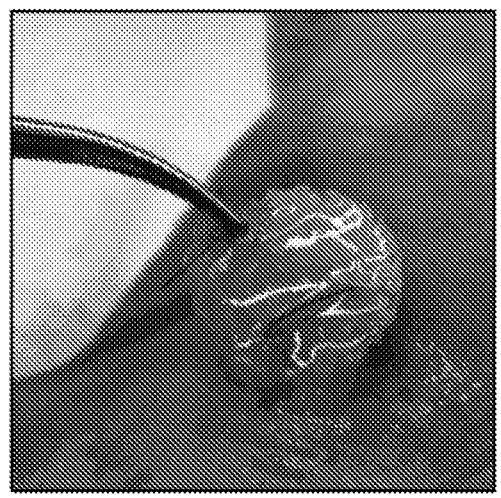
FIG. 1G  FIG. 1H

Implanted Cord Architecture        Resultant in vivo host vasculature

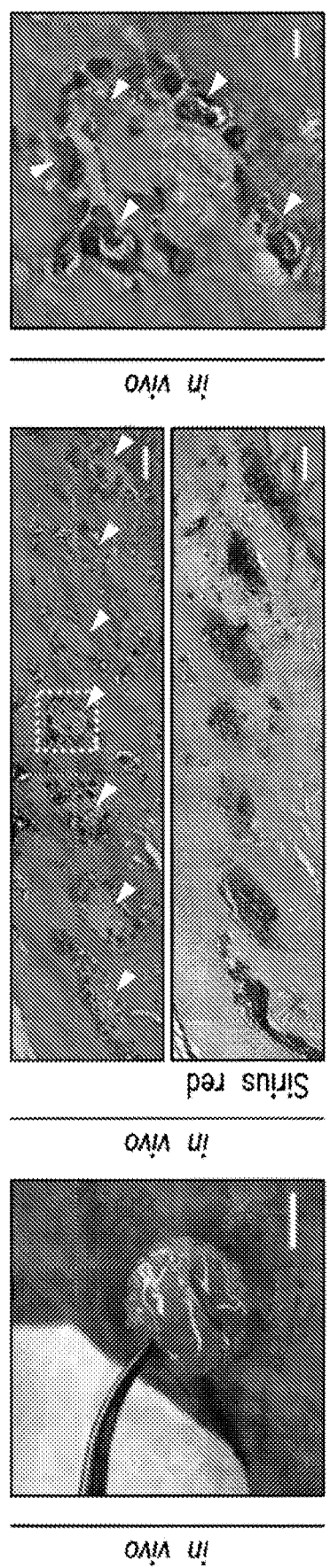

Sirius red Fast green

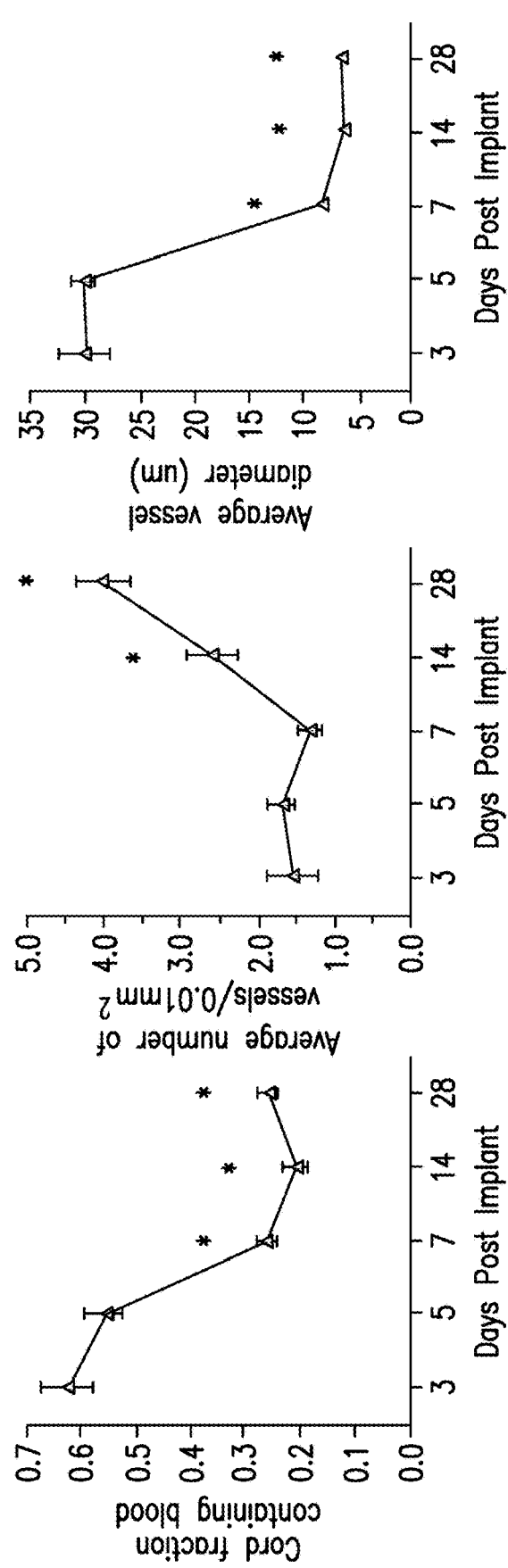
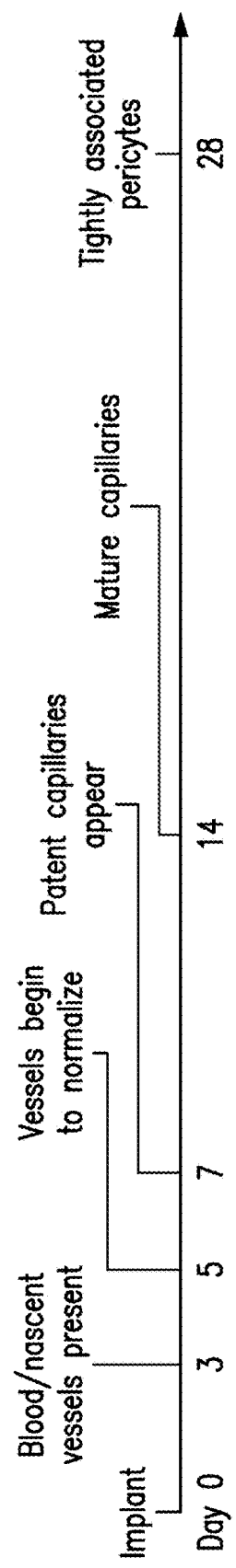
FIG. 8E
FIG. 8F

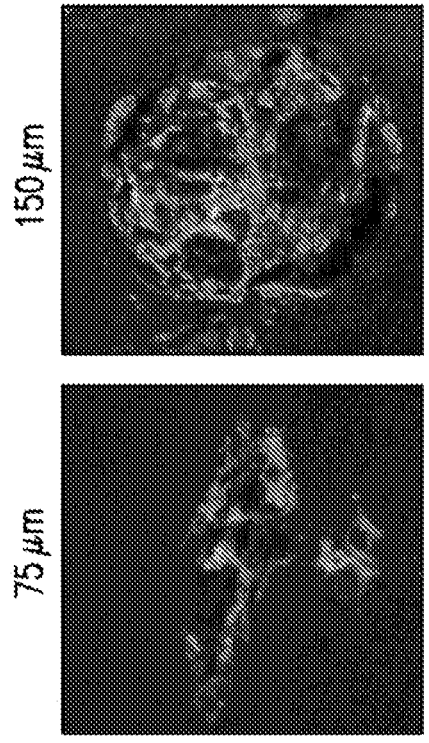
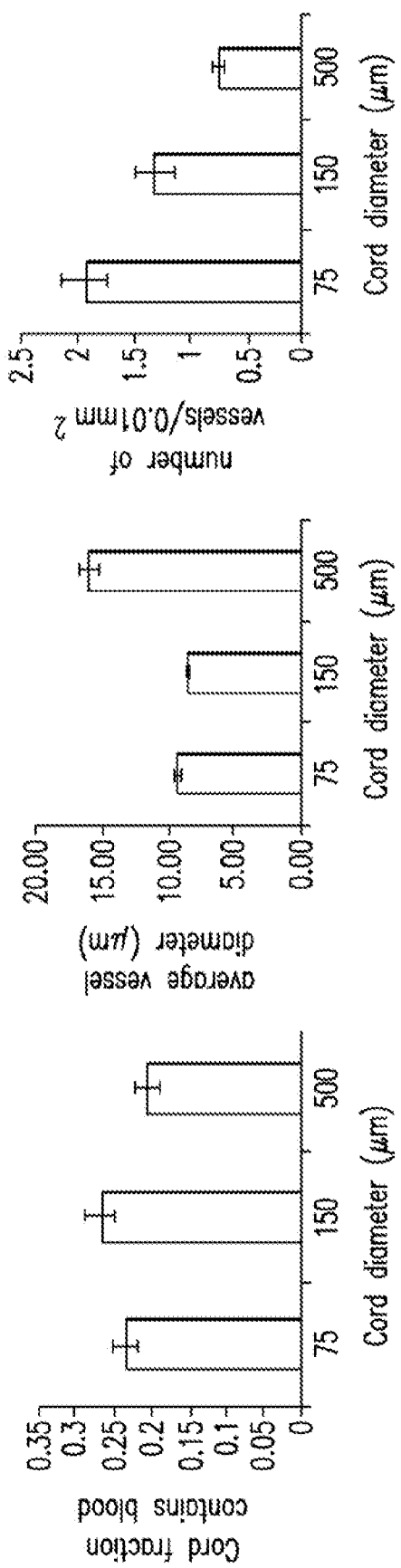
FIG. 18C
FIG. 18D

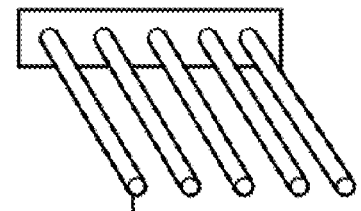
Sacrificial Filaments
FIG. 20A
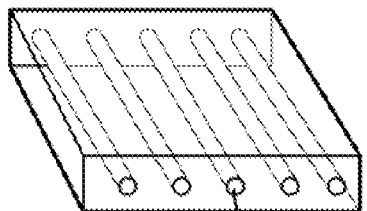
Casing    Channels
FIG. 20B
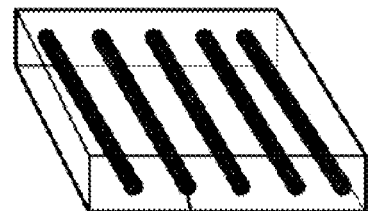
Cell Cords
FIG. 20C
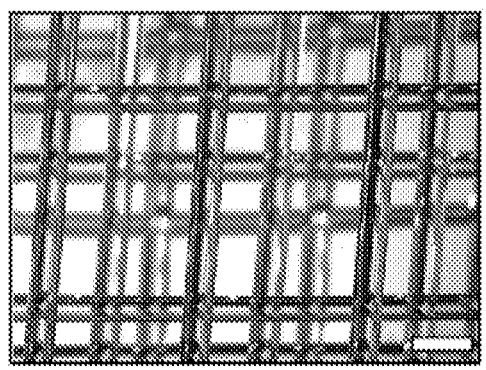
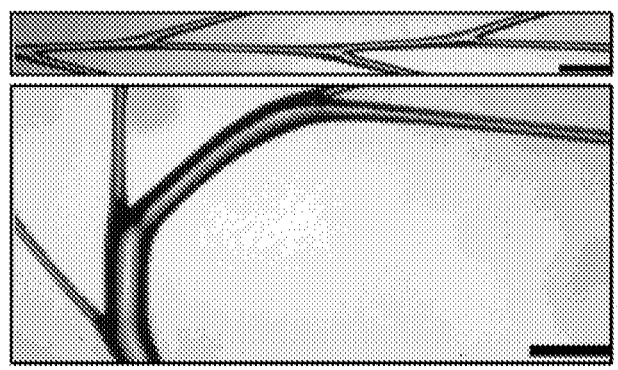
FIG. 20D
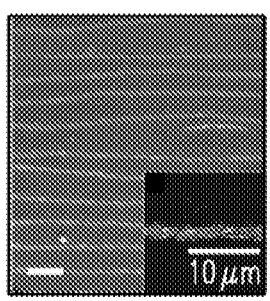 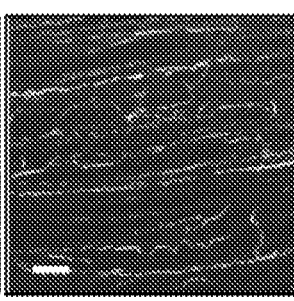 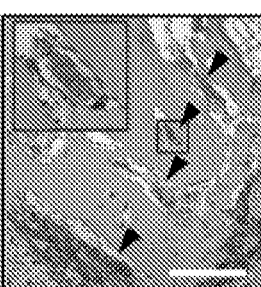 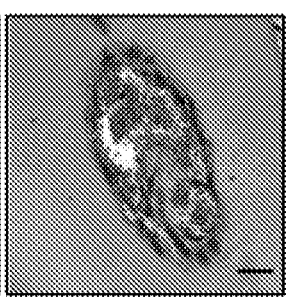
FIG. 21A  FIG. 21B  FIG. 21C  FIG. 21D

BIOMATERIALS FOR ENHANCED IMPLANT-HOST INTEGRATION

CROSS-REFERENCE TO RELATED APPLICATION

This application is a divisional of U.S. patent application Ser. No. 16/589,768, filed on Oct. 1, 2019, which application is a divisional of U.S. patent application Ser. No. 14/593,555, filed on Jan. 9, 2015, now U.S. Pat. No. 10,426,870, which is a continuation of International Application No. PCT/US2013/049933, filed on Jul. 10, 2013, which claims priority to U.S. Provisional Application Ser. No. 61/670,100, filed on Jul. 10, 2012, each of which is incorporated herein by reference in their entireties.

STATEMENT OF GOVERNMENT INTEREST

This invention was made with government support under Grant Numbers EB00262 and EB08396 awarded by the National Institutes of Health. The government has certain rights in the invention.

BACKGROUND

Many diseases result from damage, malfunction, or loss of a single organ or tissue type (1). While certain strategies such as organ transplants can be effective, the demand for replacement organs far exceeds availability, resulting in an average of 18 deaths per day in the US alone (3). The development of engineered tissues count among the most promising multidisciplinary approaches to fulfill this demand (1, 4). However, formation of large tissue constructs with sufficient cell mass to replace critical organ functions can be hampered by the diffusion limit of oxygen and nutrients to cells within the construct. Based on the rates of oxygen exchange, transport of nutrients and secreted factors, and waste removal, it is estimated that cells must be located within 150-200 µm of the nearest capillary blood vessel to survive and function optimally (5, 6). As such, certain efforts to implant large engineered tissue structures are hindered by significant cell death in areas that exceed this diffusion limit within hours to days of implantation.

Although some tissues can function with lower capillary densities, adequate perfusion of metabolically active tissue requires intimate localization of parenchymal cells to a dense vasculature in a highly organized manner (21, 32, 19). For example, the liver has a precisely defined organization in which hepatocytes and microvessels are interdigitated in a highly aligned microarchitecture (24, 25). In addition, the architecture of the vasculature itself, e.g., the branching frequency and angles, alignment of vessels, and tortuosity, constrains gradients of metabolite exchange and the overall flow fields through the tissue. Therefore, the engineering of such tissues can require approaches to define the geometric architecture of vascular networks for tissue-specific applications.

Certain cell-based pre-vascularization strategies of engineered tissues have utilized randomly seeded cells embedded within a three dimensional matrix. For example, investigators discovered that the speed of vascularization can be increased by allowing endothelial cells to form rudimentary networks in vitro prior to implantation (9). It has been demonstrated that implantation of scaffolds pre-seeded with endothelial cells (ECs) facilitates tubulogenesis (the formation of interconnected web-like networks of interconnected endothelial cells) within the scaffold and eventual anastomosis (connection) of the newly formed tubules to host vessels within days to weeks (6-9). Unfortunately, such networks are randomly distributed, and it is difficult to control the formation and structure of vessels in a fixed and reproducible manner. For example, the random organization of endothelial networks provides no directional guidance to incoming host vessels, often resulting in only an outer shell of the implant becomes perfused, leaving the interior core under-perfused. Furthermore, the strict spatial organization of cells, the surrounding extracellular matrix (ECM), and vasculature can impact paracrine signaling gradients that define cellular phenotypes and tissue function [10]. Therefore, the ability to precisely control the 3D geometry of vascular networks is important for the development of therapeutic tissue engineering constructs.

Although the field of tissue engineering has made progress since its inception, a question remains regarding how to rapidly and adequately vascularize and integrate an engineered tissue with host tissue. Although certain techniques have emerged as potential solutions (11, 12), and approaches that include cells have shown some promise in enhancing tissue integration, they have focused on injecting cells directly into a site or a randomly organized suspension of cells inside a biomaterial that can form small, randomly dispersed networks of cells. In addition, certain studies have not demonstrated the ability to rapidly create long-lasting vessels with the capability of long-term support of parenchymal cells (6, 13).

SUMMARY

The present disclosure provides engineered biomaterials, including patterned biomaterials having organized cell structures embedded in an extracellular matrix. The present disclosure also provides for systems and methods of a patterned biomaterial.

In certain embodiments, the cells are organized into cords. In certain embodiments, the patterned biomaterial includes an extracellular matrix scaffold having at least one organized cord. In certain embodiments, the patterned biomaterial can include a plurality of cords.

In certain embodiments, the cells are organized in clusters or islands of cells. In certain embodiments, the patterned biomaterial includes an extracellular matrix scaffold having at least one organized cluster or island of cells. In certain embodiments, the patterned biomaterial can include a plurality of cells clusters or islands.

In certain embodiments, the patterned biomaterial can include one or more cords and/or one or more clusters or islands of cells.

In certain embodiments, the cords and/or cell clusters can be formed from a suspension of cells of at least one or more cell types. For example, the cords and/or cell clusters can be formed from cell suspensions that contain endothelial cells, such as human umbilical vein endothelial cells (HUVECs). In certain embodiments, the cords and/or cell clusters can be formed from cell suspensions of at least two or more cell types. For example, cords and/or cell clusters can be formed from cell suspensions that contain endothelial cells and fibroblast-like cells, such as mesenchymal stem cells.

In certain embodiments, the cells are embedded in a naturally-derived or synthetic scaffolding to form cords. In certain embodiments, the cells are embedded in a naturally-derived or synthetic scaffolding to form clusters or islands of cells. For example, the scaffold can include, but is not limited to, peptides, proteins, carbohydrates, collagen, fibrin, fibrinogen, matrigel, agarose, polyethylene glycol, dextran, hyaluronic acid, or a combination thereof. In certain embodiments, the cells are embedded in Type 1 collagen.

In certain embodiments of the present disclosure, the cords and/or clusters of cells formed by embedding cells in a naturally-derived or synthetic scaffolding can be at least partially encapsulated in an extracellular matrix (ECM) or other physically solid scaffold. For example, in certain embodiments, the ECM scaffold can contain peptides, proteins, carbohydrates, collagen, fibrin, fibrinogen, matrigel, agarose, polyethylene glycol, dextran, hyaluronic acid, or a combination thereof, and a physical solid can include silicone rubber, plastics, glass, hydroxyappetite, poly-lactic acid, poly-glycolic acid, or other materials. In certain embodiments, the ECM scaffold is fibrin. In certain embodiments, the ECM can be seeded with one or more cells of one or more types. For example, the ECM can be seeded with hepatocytes.

In certain embodiments, the cords and/or clusters of cells are used to form a construct without any ECM scaffolding material, wherein the cords and/or clusters of cells are implanted directly with or without other cells co-mixed.

In certain embodiments, the method of fabricating a patterned biomaterial includes the placement of suspended cells into a three-dimensional (3D) mold template that contains at least one channel. For example, the method can include generating templates that have been defined with channels or trenches, suspending cells in liquid collagen and placing these cells into the channels of the template, allowing cords to form from the cells, and removing cords from templates via encapsulation in an extracellular matrix scaffold. In certain embodiments, the method can include the use of prefabricated templates.

In certain embodiments, the method of fabricating a patterned biomaterial includes the placement of suspended cells into a 3D mold template comprising an ECM scaffolding. For example, the method can include generating a 3D lattice, at least partially encapsulating the 3D lattice in an ECM scaffolding, removing the lattice to form channels, wells, or grooves within the ECM, and suspending cells in liquid collagen and placing these cells into the channels, wells, or grooves of the ECM scaffolding. In certain embodiments, the lattice can include carbohydrates that dissolve upon contact with liquid, such as cell culture media.

In certain embodiments, the channels of the template can differ in shape, diameter, and length to generate cords of varying structures. For example, cords can be fabricated into cylindrical, Y-shaped, and T-shaped structures. In certain embodiments, the cords can be fabricated into structures that differ in length, diameter, density, and shape. In certain embodiments, the properties of the cords can be altered to suit a particular application. In certain embodiments, the overall network organization of cords can be defined, for example, by the number and location of branchpoints, connections, three-dimensional organization, degree of anisotropy, alignment, diameters, lengths, and more.

In certain embodiments, the template can contain one or more wells and/or channels to generate clusters or islands of cells. In certain embodiments, the islands and/or cluster of cells can be fabricated into structures that differ in diameter, density, three dimensional organization and shape. In certain embodiments, the properties of the clusters or islands of cells can be altered to suit a particular application.

In certain embodiments, the patterned biomaterial can be used to treat an ischemic tissue of a subject. For example, the patterned biomaterial can be implanted onto a subject to increase the blood flow to regions of a tissue that are not receiving adequate blood flow. In certain embodiments, pattern biomaterial can be used to treat cardiac ischemia, peripheral vascular disease, or chronic wounds such as diabetic ulcers.

BRIEF DESCRIPTION OF THE DRAWINGS

Exemplary embodiments of the disclosure can be understood by referring, in part, to the following description and the accompanying drawings.

FIGS. 1A-1H illustrate methods and results of testing whether patterned cords induced the extent and organization of vivo vessel formation in vivo.

FIG. 5A shows a process flow for fabricating and implanting extracellular matrix pre-embedded with cord aggregates. 10T1/2 cells enhance cord formation by increasing contraction of the cell/collagen gels within the channels. This leads to a dramatic reduction of the cord diameter compared to the channel width, as shown in FIG. 5B. FIG. 5D shows endothelial cells (red) and 10T1/2 cells (green). Cords that initially form inside parallel channels are encapsulated in parallel arrangement within fibrin, as shown in FIG. 5C.

FIGS. 7A-7H depict the generation of EC cords. FIG. 7A shows a schematic representation of the process used to generate cords. Collagen, red; fibrin, pink. FIG. 7B shows merged phase and fluorescence images of cord formation at 0 and 10 h within PDMS microchannels (HUVECs, calcein AM red-orange; 10T1/2s, calcein AM green; bar, 50 µm). FIG. 7C shows a maximum-intensity z-projection of fluorescently labeled HUVECs (magenta) and 10T1/2s (green) (bar, 50 µm). FIG. 7D shows H&E and Sirius red/hematoxylin staining of paraffin-embedded cord constructs showing distribution of cells and collagen in cross-section (bar, 20 µm). FIG. 7E shows a bright field micrograph of EC cord constructs after removal from PDMS substrate and embedding within fibrin gel. Dark circle indicates the portion of the gel that was cut with a biopsy punch in preparation for implantation (bar, 500 µm). FIG. 7F shows a tissue construct containing cords sutured in place adjacent to the parametrial fat pad of an athymic mouse. FIG. 7G shows H&E and sirius red staining of cord-containing tissue constructs resected after 7 d in vivo. Arrowheads indicate the location of cords (bar, 25 µm). FIG. 7H depicts an inset showing higher magnification H&E staining of single cord. Arrowheads indicate areas of blood around the periphery of the cord (bar, 5 µm).

FIGS. 8A-8F illustrate that implanted EC cords drive formation of stable capillaries. FIG. 8A shows H&E staining of EC cords resected at days 3, 5, 7, 14, and 28 PI suggests the presence of blood within vessels that organize into small capillaries by day 7 (arrowheads) (bar, 10 µm). FIG. 8B shows sirius red/fast-green staining of collagen within the cords after harvest (bar, 10 µm). FIG. 8C shows Ter-119 (red) and human-specific CD31 (green) staining positively identifing RBCs and ECs and suggesting that vessels were of human origin (bar, 10 µm). FIG. 8D shows α-SMA-positive (magenta) cells with a perivascular localization seen at higher magnification (bar, 20 µm). FIG. 8E shows quantification of blood area, vessel diameter, and vessel numbers over 28 d. *P<0.05 for comparison of days 7, 14, and 28 vs. 3 and 5 in blood area and vessel diameter measurements, and days 14 and 28 vs. 3, 5, and 7 in vessel number measurements. Error bars: SEM, n≥20, one-way ANOVA followed by Tukey's post hoc test. FIG. 8F shows a timeline representation of vessel maturation.

FIG. 9A shows bright field images of fibrin gels in vitro before implantation, which contain self-organized networks of HUVECs and 10T1/2s, patterned EC cords, or EC cords patterned into a branched topology (Upper row; bars: 250 µm, 500 µm, and 500 µm, respectively). (Upper row) These samples were implanted in the intraperitoneum of nude mice, and after 14 d FITC-dextran was perfused via tail vein injection. (Lower row) Representative FITC-dextran images (bars, 100 µm). To further distinguish human from mouse endothelium, gels containing parallel arrays of cords were implanted, and mice were perfused with human-specific lectin (UEA-1—TRITC) and mouse-specific lectin (HPA—Alexa 488) via tail vein injection at 14 d PI as shown by FIG. 9B. Representative images demonstrate that the resultant perfused microvascular network of the graft is composed of a parallel array of patent capillaries that are chimeric in composition (red, human; green, mouse; bar, 150 µm).

FIG. 10A shows three types of tissue constructs were generated: (i) hepatocyte aggregates only (No EC), (ii) randomly seeded HUVECs and 10T1/2s with hepatocyte aggregates (Random EC), and (iii) hepatocyte aggregates adjacent to EC cords (EC Cord; bar, 20 µm) using labeled hepatocytes (green, calcein AM) and HUVECs (calcein, red-orange). FIG. 10B shows sirius red/fast-green staining (Left) revealed cellular aggregates (dotted line) close to spatially patterned collagen structures (black arrows) indicative of cords as well as to vessels that appeared to carry fast-green-stained blood (white arrows; bar, 50 µm). Immunostaining for Ter-119 (red; erythrocytes) and ARG-1 (green; hepatocytes) confirmed the presence of RBCs directly adjacent to viable hepatocyte aggregates at 20 d PI (Right bars, 25 µm). FIG. 10C depicts luciferase activity showing significantly increased albumin promoter activity in the tissue constructs containing patterned rat hepatocyte aggregates and EC cords at least 20 d PI. Error bars: SEM, n=13 and 5 for EC Cords and No EC groups, respectively. *P<0.05, one-way ANOVA followed by Tukey's post hoc test. Similar to histochemistry for rat hepatic tissues, Sirius red staining demonstrated the presence of patterned collagen remnants of cords (Left) as shown by FIG. 10D. Further addition of fast green identified capillaries containing blood (white arrows) as well as cellular aggregates (dotted line) near these collagen cores (Center). Triple immunostaining for ARG-1 (green; hepatocytes), Ter-119 (white; erythrocytes), and huCD31 (red; human endothelial cells) demonstrated localization of RBCs within capillaries that were lined with human endothelium and immediately adjacent to viable hepatocyte aggregates (Right; bars, 25 µm). FIG. 10E shows a representative image of luciferase activity under the control of the albumin promoter showing increased primary human hepatocyte function in constructs containing patterned EC cords. Constructs containing human hepatocytes patterned with EC cords performed significantly better than all control groups for at least 18 d PI. Albumin promoter activity was similar among control groups, which contained EC cords but were ligated upon implantation (EC Cord Ligated), randomly seeded HUVECs and 10T1/2s (Random EC), or no cells (No EC). Error bars: SEM, n=11, 7, 5, and 6 for EC Cord, No EC, EC Cord Ligated, and Random EC groups, respectively. *P<0.05, one-way ANOVA followed by Tukey's post hoc test.

FIG. 11A shows a time-lapse imaging depicting cord formation in samples treated with vehicle, blebbistatin, or Y27632 (bar, 50 µm). FIG. 11B shows a quantification of cord contraction revealing rapid increase in contraction after wash-out of contractility inhibitors. Constructs were treated with 20 µM blebbistatin or 25 µM Y27632 at 7.5 or 6.5 h.

FIG. 12A shows H&E staining of fibrin gel (no cells) implanted and resected 5 d PI. FIG. 12B shows H&E staining of fibrin gel containing decellularized endothelial cell (EC) cords 5 d PI (bars, 25 µm). FIG. 12C shows fibrin gel containing a mixture of HUVECs and 10T1/2s used in making EC cords. Cells were allowed to organize into networks in vitro for 2 d before implantation and resected 5 d PI.

FIG. 16A shows a single dispersed DAPI-positive cells that could be identified in constructs as early as 1 min after DAPI injection. By 20 min post injection, DAPI-positive hepatic aggregates were identified throughout the constructs as shown by FIG. 16B. These studies demonstrate that a small molecule similar in size to luciferin permeates the construct and stains hepatic aggregates within 20 min post injection within time scales relevant for bioluminescence imaging (bar, 50 µm).

FIGS. 18A-18D show that the cord diameter can be altered and still promote vessel formation.

FIGS. 20A-20D show a certain embodiment by which the patterned biomaterial can be generated. FIG. 20A shows fabrication of patterned biomaterial involving printing 3D filament networks, FIG. 20B shows polymerization of casing matrix and dissolution of filaments to leave channels, and FIG. 20C shows forming cell cords in the channels. FIG. 20D shows examples of printed filaments, which range from 50 to 500 μm diameter.

FIGS. 21A-21D show the direct vascularization and perfusion achieved with the patterned biomaterial of the present disclosure. FIG. 21A shows the patterned biomaterial with parallel cords. Inset shows cellular organization imaged by confocal microscopy. FIG. 21B shows direct demonstration of perfused parallel host vasculature, where FITC-dextran was injected by tail vein and immediately appeared in the implant neovessels. FIG. 21C shows staining of host vessels that have invaded into an implant. Blood is evident 5 days post implantation in pre patterned periodic intervals due to the location of the cords (green arrows). Note inset and FIG. 21D each show endothelial-lined blood vessels in cross section, with red blood cells inside indicating perfusion by the host.

DETAILED DESCRIPTION

Figure 1A:
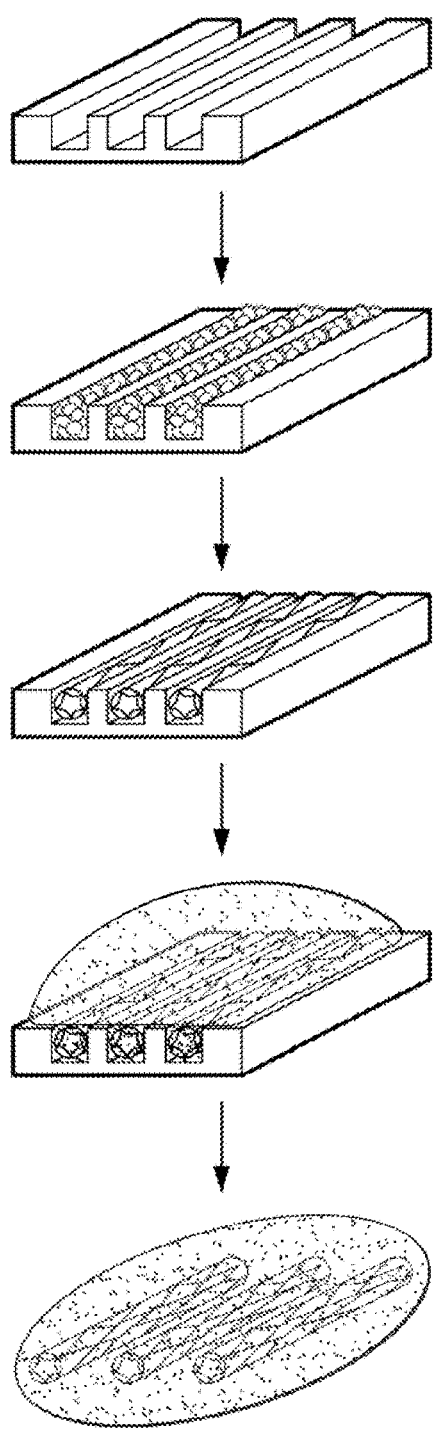

The present disclosure provides engineered biomaterials, including a patterned biomaterial having organized "cords" and extracellular matrix embedded in a 3D scaffold template.

As used herein, the term "cords" refers to cells and/or a naturally-derived and/or synthetic scaffolding that are organized into structures that resemble cylinders, rods, strings, or filaments and networks of such structures. Pre-patterning of these biomaterials can lead to enhanced integration of these materials into host organisms, wherein host cells can invade or integrate in a manner guided by the architecture of the cords. This integration can involve blood vessels, thus providing a strategy for enhancing the viability of engineered tissues by allowing for increased vascularization of engineered tissue. In addition, these patterned biomaterials provide a method for promoting vasculogenesis in a host tissue. This integration can also involve other host systems such as the nervous system, muscle, bone, or immune system, and thereby promote engineered tissue innervation, muscle integration, bone integration, or immune surveillance, respectively. In certain embodiments, a cord of the present disclosure can include cells and a naturally-derived and/or synthetic scaffolding. In certain embodiments, the cords can include a naturally-derived and/or synthetic scaffolding without cells, or fragments thereof. In certain embodiments, the cords can include cells, or fragments thereof, without a naturally-derived and/or synthetic scaffolding.

In certain embodiments, the present disclosure provides a patterned biomaterial having cells organized in clusters and/or islands embedded in an extracellular matrix (ECM) scaffolding.

As used herein, the term cell "clusters" and/or "islands" refer to one or more cells, with or without extracellular matrix, that are organized in unconnected structures that resemble balls, discs, or islands. Pre-patterning of these cells can provide a method for providing bioactive agents, such as paracrine factors, to the one or more cells embedded in the ECM scaffolding, or act to modulate how host tissue and cells respond to the patterned biomaterial. In certain embodiments, a cluster or island of the present disclosure can include cells and a naturally-derived and/or synthetic scaffolding. In certain embodiments, the clusters or islands can include a naturally-derived and/or synthetic scaffolding without cells, or fragments thereof. In certain embodiments, the clusters or islands can include cells, or fragments thereof, without a naturally-derived and/or synthetic scaffolding.

There is a need to develop a technique for inducing angiogenesis, the formation of new blood vessels, in a controlled fashion within organized 3D tissue constructs. There is also a need to induce blood vessel formation of a tissue in a subject that does not receive adequate blood flow. The present disclosure addresses this need by engineering a patterned biomaterial comprising an extracellular matrix (ECM) scaffold that has been embedded with geometrically-defined aggregates of cells. In certain embodiments, the cords of the present disclosure have a tubular structure. In certain embodiments, the cords of the present disclosure are at least partially embedded in the ECM scaffold. In certain embodiments, the cell clusters and/or islands of the present disclosure are at least partially embedded in the ECM scaffold.

The patterned biomaterials of the present disclosure promote the rapid formation of vessels that are spatially delineated, providing novel approaches to vascularizing engineered tissues, treating ischemic diseases, and promoting tissue healing and integration. Implantation of pre-formed cords into a subject can lead to engraftment, remodeling of the local microenvironment, anastomosis, and formation of stable capillaries within an implanted scaffold that directs blood vessels and blood flow. By employing cords generated in vitro, the subsequent formation of blood vessels in vivo is able to be spatially controlled.

The pre-organization of cells into patterned networks (i.e., cords or cylinders) of the present disclosure provides a means to support rapid invasion and integration of host vasculature into the device to generate perfused, functional blood vessels by providing a pre-specified architecture as a template in which the new blood vessels mirror the diameter and architecture of the implanted cords. The architecture of the networks of cells engineered in vitro during the assembly of the patterned biomaterial defines the in vivo architecture (vessel diameters and network topology) of the blood vessel network that forms after implantation. Because these patterned networks act as "blood vessel highways" for the invading host tissue, their organization (patterned orientation, size, density, connectivity) can be engineered to rationally impact the rate and extent of host cell integration, and thus be used as a means to direct revascularization from a well perfused site to reach into and support ischemic tissues. In certain embodiments, the cells and matrix originally in the patterned biomaterial can be partially or entirely replaced by host cells and tissue, with the architecture of the patterned biomaterial being templated and preserved by the new host tissue.

This use of patterning technology for pre-organizing cells into cords with increased cell-cell contacts and for controlling the ultimate in vivo geometry of blood vessels has not been previously described. Successful patterning of cells and subsequent formation of vessels in vivo constitutes a significant technical advance within the field of tissue engineering. As a result, the functional importance of tissue architecture is not limited to vascularization. As such, the concepts of tissue patterning of the present disclosure are widely applicable to many different types of engineered tissues and cell types.

Understanding the cellular dynamics underlying the vascularization process within an engineered tissue is critical to designing optimal vascularization strategies. The present disclosure provides for investigation of some of the biological mechanisms within these processes including the role of the implanted cells and their contribution to the nascent vasculature, the dynamics of host vessel invasion and anastomosis and the role of cell-cell contacts during vessel formation. Insights gained from the present disclosure can shed additional light on questions regarding network formation/tube assembly, differentiation and anastomosis during development as well as aiding in the development of new vascularization strategies.

Methods of Fabricating the Patterned Biomaterial

Figure 5B:
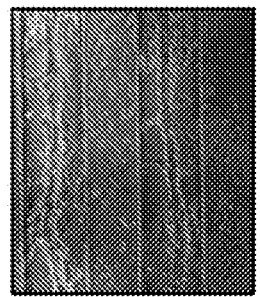
FIGS. 5A-5D illustrate a schematic of certain embodiments of the present disclosure.
Figure 5C:
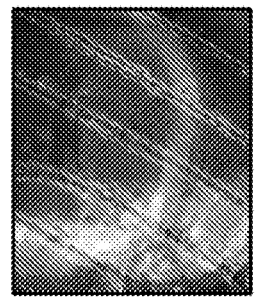
Figure 5D:
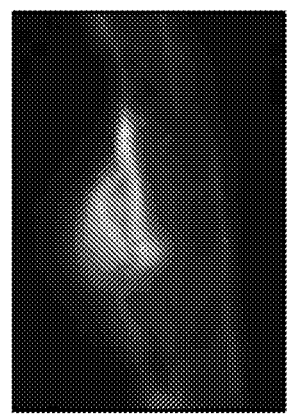
Figure 5A:
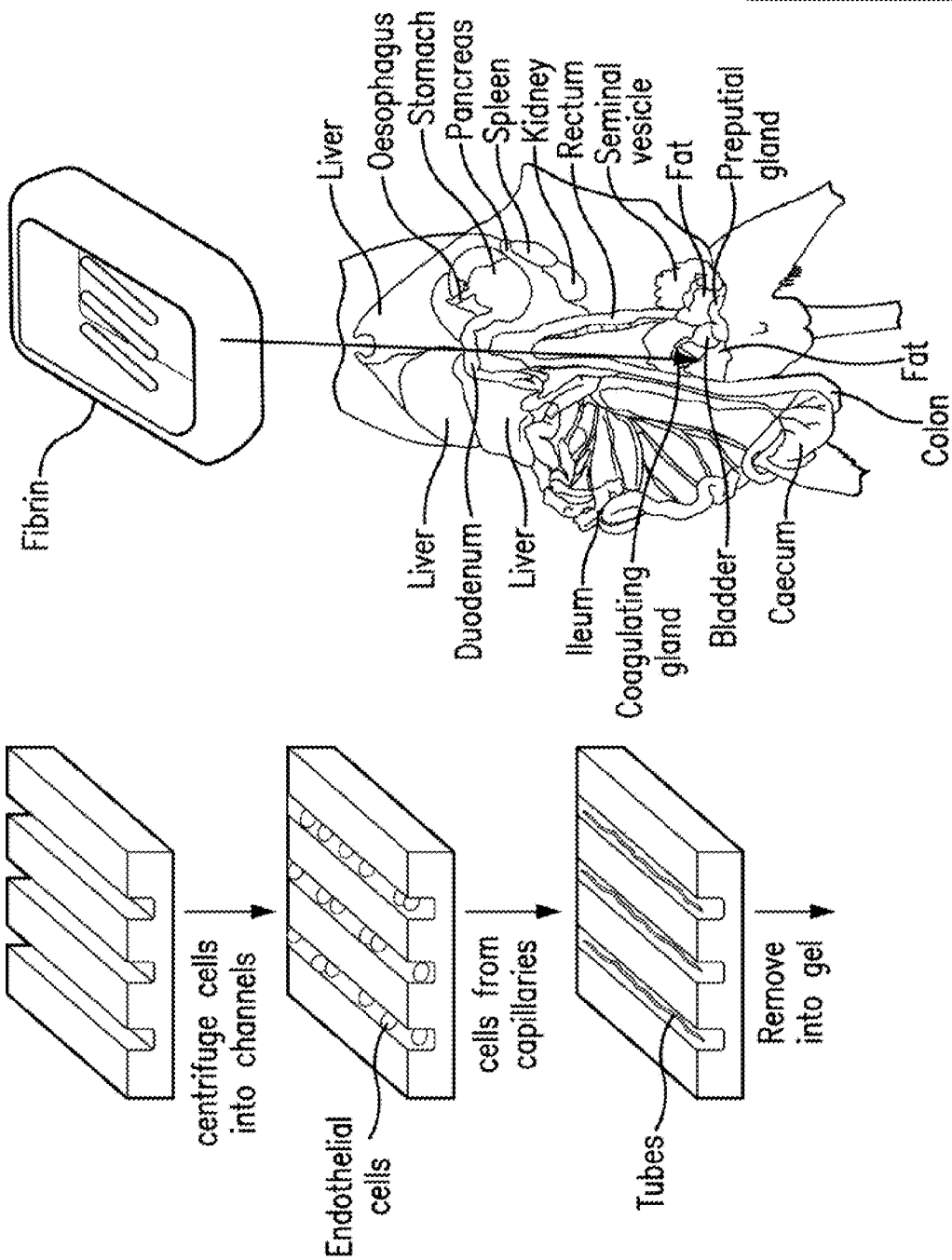

In certain embodiments, the patterned biomaterials of the present disclosure can be formed by a process according to FIG. 5A. In certain embodiments, the method for fabricating cords and embedding these structures in extracellular matrix includes (1) generating 3D templates that have been defined with channels or trenches, (2) suspending endothelial cells in liquid collagen and centrifuging these cells into the channels of the template, (3) removing excess cell/collagen suspension to allow cord aggregates to form, and (4) removing cords from templates via encapsulation in an extracellular matrix scaffold.

In certain embodiments, the method for fabricating the patterned biomaterials of the present disclosure is provided in Raghavan et al., the disclosure of which is incorporated herein by reference (2).

In certain embodiments, the method for fabricating the patterned biomaterial includes (1) suspending cells in a naturally-derived and/or synthetic scaffolding, (2) placing the suspended cells into the channels of a 3D template, and (3) allowing the cells to form one or more cords at least partially embedded in the naturally-derived and/or synthetic scaffolding. In certain embodiments, the method for fabricating the patterned biomaterial can include the removal of the cords from the 3D template via encapsulation in an extracellular matrix scaffold. In certain embodiments, the cords are not encapsulated in an ECM scaffold.

In certain embodiments, organizing cells and material into spatial arrangements, such as cords and/or cell clusters or islands, can be accomplished by physically constraining the placement of cells/material by the use of wells or grooves, or injecting cells into microfluidic channels or oriented void spaces/pores. In certain embodiments, the cells can be organized by physically positioning cells with electric fields, magnetic tweezers, optical tweezers, ultrasound waves, pressure waves, or micromanipulators. In certain embodiments, cells can be organized by patterning the attachment of cells into specific arrangements by seeding them onto fibers. In certain embodiments, cells can be organized by novo fabrication such as by layer-by-layer or 3D printing.

In certain embodiments, the naturally-derived and/or synthetic scaffolding, can include, but is limited to, fibrin, fibrinogen, fibronectin, collagen, polyorthoester, polyvinyl alcohol, polyamide, polycarbonate, carbohydrates, agarose, alginate, poly(ethylene) glycol, polylactic acid, polyglycolic acid, polycaprolactone, polyvinyl pyrrolidone, a marine adhesive protein, cyanoacrylate, polymeric hydrogel, analogs, or a combination thereof.

In certain embodiments, the patterned biomaterial can be formed by adding cells directly into or onto an extracellular matrix scaffold, in the absence of collagen. For example, cords can be formed by seeding cells without collagen into pre-existing hollow channels of a 3D template and encapsulating the cells into an ECM scaffold.

In certain embodiments, the patterned biomaterial does not contain the naturally-derived and/or synthetic scaffolding or the ECM scaffolding material. In certain embodiments, the patterned biomaterial of the present disclosure is formed in the absence of ECM scaffolding.

In certain embodiments, the patterned biomaterial does not contain cells, either because the cells were introduced and then later removed or killed or because the cells were never introduced. In certain embodiments, the patterned biomaterial does not contain living cells. In certain embodiments, the cords and/or clusters of the patterned biomaterial can contain a naturally-derived and/or synthetic scaffolding in the absence of cells. For example, the naturally-derived and/or synthetic scaffolding can be directly added without cells to form cords and/or clusters. In certain embodiments, the naturally-derived and/or synthetic scaffolding can be remodeled by cells, secreted by cells, and/or produced by cells that were later removed or killed.

In certain embodiments, the patterned biomaterial can contain two or more cell types. In certain embodiments of the method, the two or more cell types can be co-introduced or sequentially introduced in the patterned biomaterial. For example, the two or more cell types can be introduced in the same spatial position, similar spatial positions, or different spatial positions, relative to each other. In certain embodiments, the two or more cell types are introduced into or onto different areas of the patterned biomaterial. For example, the cords and/or cell clusters can be embedded in a naturally-derived and/or synthetic scaffolding, e.g., collagen, which can be further encapsulated in an ECM scaffold that is seeded with a distinct cell type.

In certain embodiments, the 3D templates can include naturally-derived and/or synthetic material. For example, the template can be composed of silicone or PDMS. In certain embodiments, the template can contain one or more channels. For example, the template can contain at least 1, 2, 3, 4, 5, 6, 7, 8, 9, 10, 15, 20, 30, or 40 channels. In certain embodiments, the one or more channels can be arranged in parallel formation. In certain embodiments, the one or more channels can be arranged in a non-parallel formation. In certain embodiments, the one or more channels can be organized with specific branch patterns such as rectilinear grids, bifurcated trees, in 2D or 3D organizations, with certain spacings of less than about 1 µm, greater than about 1 µm, 2, 4, 5, 8, 10, 15, 20, 25, 30, 40, 50, 80, 100, 150, 200, 250, 300, 500, 700, or 900 µm. The width of each line, groove and/or structure can be less than about 1 µm, greater than about 1 µm, 2, 4, 5, 8, 10, 15, 20, 25, 30, 40, 50, 80, 100, 150, 200, 250, 300, 500, 700, 900 µm, 1 mm, 2 mm, 5 mm, 10 mm, or 20 mm.

In certain embodiments, the template can contain one or more wells and/or grooves to form one or more cell clusters or islands. For example, the template can contain at least 1, 2, 3, 4, 5, 6, 7, 8, 9, 10, 15, 20, 30, or 40 wells. In certain embodiments, the one or more wells can be organized with certain spacings of less than about 1 µm, greater than about 1 µm, 2, 4, 5, 8, 10, 15, 20, 25, 30, 40, 50, 80, 100, 150, 200, 250, 300, 500, 700, 900 µm, 1 mm, 2 mm, 5 mm, 10 mm, or 20 mm.

In certain embodiments, the 3D template can be generated by molding, templating, photolithography, printing, deposition, sacrificial molding, stereolithography, or a combination thereof.

In certain embodiments, the ECM scaffold can function as the 3D template. For example, the patterned biomaterial can be formed by at least partially encasing the 3D template in an ECM scaffold. The 3D template can then be removed to create channels, wells and/or grooves in the ECM scaffold. Cells can then be added to the newly created channels, wells and/or grooves of the ECM scaffold to form cords and/or clusters or islands of cells. In certain embodiments, the 3D template can be a carbohydrate lattice that dissolves following incubation in cell media to form empty channels, wells, and/or grooves in the ECM scaffold.

In certain embodiments, the patterned biomaterial of the present disclosure can be fabricated through the use a custom 3D printer technology to extrude lattices of carbohydrate glass filaments with predefined diameters, spacings and orientations. In certain embodiments, soluble (clinical-grade, sterile) fibrinogen and thrombin are then combined and poured over the lattice. After the solution has polymerized into insoluble fibrin, the carbohydrate filaments are dissolved, leaving behind channels within the fibrin. The channels can then be filled with a suspension of cells, such as endothelial and perivascular cells, in a naturally-derived or synthetic scaffolding (e.g., soluble type I collagen) that subsequently is polymerized to trap the cells within the channels to form cords.

Patterned Cell Structures

In certain embodiments, the cords and/or cell clusters or islands of the present disclosure can be formed from any cell type using any naturally-derived or synthetic scaffolding, including, but not limited to peptides, proteins, carbohydrates, matrigel, hyaluronic acid, collagen, fibrin, fibrinogen, fibronectin, polyorthoester, polyvinyl alcohol, polyamide, polycarbonate, agarose, alginate, poly(ethylene) glycol, polylactic acid, polyglycolic acid, polycaprolactone, polyvinyl pyrrolidone, a marine adhesive protein, cyanoacrylate, polymeric hydrogel, analogs, or a combination thereof. Additional examples of scaffolding are disclosed in U.S. Pat. No. 8,318,193 and U.S. Patent Application No. 20012/0288564, which are incorporated in their entirety by reference herein.

In certain embodiments, the scaffolding can be collagen. For example, the cells can be suspended in collagen and placed in the channels or wells of a 3D template to form organized cords and/or cell clusters or islands in a collagen scaffold. In certain embodiments, the cells can be placed between two layers of collagen in the channels of a 3D template.

In certain embodiments, the collagen is human collagen, recombinant collagen, or recombinant human collagen. In certain embodiments, the liquid collagen can contain collagen type I, type II, type III, type IV, type V, type VI, type VII, type VIII, type IX, type X, type XI, type XII, type XIII, type XIV, type XV, type XVI, type XVII, type XVIII, type XIX, type XX, type XXI, type XXII, type XXIII, type XXIV, type XXV, type XXVI, XXVII, type XXVIII, or type XXIX, or mixtures thereof. In certain embodiments, the collagen is Type I collagen and/or approved for clinical use. In certain embodiments, the collagen is obtained from an animal, including, but not limited to, mouse, rat, bovine, and porcine.

In certain embodiments, the naturally-derived or synthetic scaffolding can be degradable upon exposure to environmental conditions. For example, the ECM scaffold can be degraded by the presence of hydrolytic enzymes, presence of proteasomal enzymes, pH lower than 5 and reducing conditions.

In certain embodiments, the cords and/or cell clusters or islands of the present disclosure can be formed without using any naturally-derived or synthetic scaffolding.

In certain embodiments, the cords and/or cell clusters or islands of the patterned biomaterial of the present disclosure can be formed from a monotypic suspension of cells. In certain embodiments, a monotypic suspension of cells suspended in liquid collagen can be used. For example, human mesenchymal stem cells or neuronal cells can be used. In certain embodiments, the monotypic suspension of cells contains endothelial cells.

In certain embodiments, the cords and/or cell clusters or islands of the patterned biomaterial of the present disclosure can be formed from a heterotypic suspension of cells. For example, the cords of the patterned biomaterial of the present disclosure can be formed from a heterotypic suspension of cells suspended in liquid collagen. In certain embodiments, the heterotypic suspension of cells of the cords and/or cell clusters or islands of the present disclosure contains two or more cell types.

In certain embodiments, the cell suspension can contain endothelial cells. In certain embodiments, the endothelial cells are adult vein endothelial cells, adult artery endothelial cells, embryonic stem cell-derived endothelial cells, iPS-derived endothelial cells, umbilical vein endothelial cells, umbilical artery endothelial cells, endothelial progenitors cells derived from bone marrow, endothelial progenitors cells derived from cord blood, endothelial progenitors cells derived from peripheral blood, endothelial progenitors cells derived from adipose tissues, endothelial cells derived from adult skin, or a combination thereof. In certain embodiments, the umbilical vein endothelial cells are human umbilical vein endothelial cells (HUVEC).

In certain embodiments, the cell suspension can contain fibroblast and/or fibroblast-like cells. In certain embodiments, the fibroblasts are human foreskin fibroblasts, human embryonic fibroblasts, mouse embryonic fibroblasts, skin fibroblasts cells, vascular fibroblast cells, myofibroblasts, smooth muscle cells, mesenchymal stem cells (MSCs)-derived fibroblast cells, or a combination thereof.

In certain embodiments, the cell suspension can contain tissue-specific cells. The tissue-specific cells can be muscle cells, pancreatic beta cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, stem cell or iPS-cell derived tissue specific cells, or a combination thereof. In certain embodiments, the tissue-specific cells are muscle cells, pancreatic beta-islet cells, cardiomyocytes, liver cells, lung cells, neural cells, bone or kidney cells, or a combination thereof.

In certain embodiments, the tissue-specific cells are of a neuronal cell type, including, but not limited to, astrocytes, glial cells, neuronal cells, or neuronal stem cells.

In certain embodiments, the heterotypic cell suspension can contain, for example, at least one of the following cell types: endothelial cells, fibroblast cells, pericytes, mesenchymal stem cells, smooth muscle cells, any other cell type that exhibits fibroblast-like properties, epithelial cells, neuronal cells, stem cells, lung cells, kidney cells, pancreatic cells, cardiac cells, liver cells, skeletal cells, urethral cells, progenitor cells, or a combination thereof.

In certain embodiments, the cells present in the heterotypic cell suspension can be in a ratio of about 50:1, 20:1, 10:1, 5:1, 2:1, or 1:1, with endothelial cells generally being the predominant cell present in the heterotypic suspension, but these ratios can vary depending on the type of cells involved. One of ordinary skill in the art, with the benefit of this disclosure, will be able to determine the appropriate ratio of cell types in a heterotypic suspension to achieve the objectives of the present disclosure.

In certain embodiments, the ratio of endothelial cells to other cell types present in the cell suspension can be from about 1:1000, about 1:100, about 50:1, about 30:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:30, about 1:50, about 1:100 or about 1:1000. In certain embodiments, the ratio of endothelial cells to other cell types can be from about 50:1 to about 1:3.

In certain embodiments, the endothelial cells can be present in the cell suspension at a volume percentage from about 1%, 5%, 10%, 15%, 20%, 25%, 30%, 33%, 40%, 50%, 66%, 75%, 80%, 90%, 95%, 99%, or 100%. In certain embodiments, the endothelial cells are present in the cell suspension at a volume percentage from about 30%.

Cells suitable for forming the cords and/or cell clusters or islands of the patterned biomaterial of the present disclosure can be derived from any suitable source. The subject to receive the implant of the patterned biomaterial of the present disclosure can determine the source of the cells to form the cords and/or cell clusters of the patterned biomaterial. In certain embodiments, the cells can be derived from an autologous source. For example, the cells can be derived from the subject to be implanted with the patterned biomaterial. For example, endothelial cells can be derived from the skin of the subject to be implanted with the patterned biomaterial. In certain embodiments, endothelial cells can be obtained from any tissue in the body, including, but not limited to, umbilical cord, skin, heart, liver, kidney, adrenals, brain, muscle, bone, bone marrow and fat tissue. In certain embodiments, endothelial cells can also be generated from stem cells derived from various sources that are then differentiated into endothelial cells. In certain embodiments, cells can be cultured for a period of time under various conditions to induce certain phenotypes before patterning into the cords and/or cell clusters or islands.

In certain embodiments, the patterned biomaterial contains a combination of at least one type of endothelial cell and at least one other cell type for the formation of a three-dimensional engineered tissue containing an internal blood vessel architecture.

A heterotypic cell suspension of cells of the engineered biomaterial of the present disclosure can have certain advantages over the use of a monotypic suspension of endothelial cells. First, a heterotypic cell suspension having endothelial cells enhances cord formation by increasing contraction of the cell/ECM gels within the channels or trenches of the template. The resulting cords have a reduced cord diameter as compared to the channel/trench width of the template. Second, in certain instances, endothelial cells can survive and function better in the presence of other cell types.

The properties of the cords of the present disclosure can be varied to suit a particular application. In certain embodiments, the density of the cords can be changed. In certain embodiments, cords of different diameters and shapes can be fabricated. Examples of the certain shapes and diameters that the cords can be fabricated into include, but are not limited to, cylindrical, Y-shaped, and T-shaped structures. In certain embodiments, the overall network organization of cords can be defined, for example, by the number and location of branchpoints, connections, three-dimensional organization, degree of anisotropy, alignment, diameters, lengths, and the like. In certain embodiments, the organization of the one or more cords within the patterned biomaterial can be arranged to dictate the organization of the new vasculature and the directionality of blood flow. For example, the one or more cords can be organized in a parallel arrangement. In certain embodiments, the one or more cords can be organized in a non parallel arrangement.

In certain embodiments, the cords can be organized with specific branch patterns such as rectilinear grids, bifurcated trees, in 2D or 3D organizations. In certain embodiments, the spacing between adjacent cords can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the width and/or diameter of the one or more cords of the present disclosure can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the length of the one or more cords of the patterned biomaterial can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, or 900 µm, 1 mm, 2 mm, 5 mm, 1 cm, 2 cm, 3 cm, 4 cm, 10 cm, 20 cm, 50 cm, 75 cm, 100 cm, or a combination thereof.

In certain embodiments, the number of cords contained within the patterned biomaterial can vary. In certain embodiments, the patterned biomaterial includes at least 1, 2, 3, 4, 5, 10, 15, 20, 25, 30, 35, 50, 100, 150, 200, 300, 400, 500, 1000, 10,000, 100,000, or 1,000,000 organized cords. For example, in treatment areas where high vascular density is required or desired, the number of cords in the patterned biomaterial can be increased to the proper number. In certain embodiments, in treatment areas where lower vascular density is required or desired, the number of cords in the patterned biomaterial can be modified to the proper number to achieve the desired vascular density.

In certain embodiments, the properties of each cord within a patterned biomaterial can differ. For example, each cord of a patterned biomaterial can have different properties, such as diameter, length, density, shape and pattern. In certain embodiments, the spacing between a subset of cords can differ from the spacing between another subset of cords of the same patterned biomaterial. In certain embodiments, the 3D arrangement or pattern of a subset of cords can differ from the 3D arrangement or pattern of another subset of cords. In certain embodiments, the density, length, shape, or diameter of a subset of cords can differ from the density, length, shape, or diameter of another subset of cords.

In certain embodiments, sections of the patterned biomaterial can contain one or more cords of different alignments. For example, in one section of the patterned biomaterial, the one or more cords can be organized in a parallel arrangement and in a different section of the patterned biomaterial, the one or more cords can be organized in a non-parallel arrangement.

In certain embodiments, each cord of the patterned biomaterial can be comprised of a different cell type. For example, one cord of the patterned biomaterial can be comprised of endothelial cells and another cord of the same patterned biomaterial can be comprised of epithelial cells.

In certain embodiments, the diameters of the cords can include, but are not limited to, 75 µm, 150 µm, and/or 500 µm. One of ordinary skill in the art, with the benefit of this disclosure, will be able to optimize the cord arrangement and properties of the cords, including but not limited to, the cells used in their formation, the number, size, aspect ratio, and orientation, to meet the specific requirements for a particular tissue engineering application.

The properties of the cluster and/or island of cells of the present disclosure can be varied to suit a particular application. In certain embodiments, the density of the cell clusters can be changed. In certain embodiments, cell clusters of different diameters can be fabricated. In certain embodiments, the overall network organization of the one or more cell clusters can be defined, for example, by the number, three-dimensional organization, alignment, diameters, density, and the like.

In certain embodiments, the width and/or diameter of the one or more cell clusters of the present disclosure can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the spacing between adjacent cell clusters can be less than about 1 µm, greater than about 1 µm, 2 µm, 4 µm, 5 µm, 8 µm, 10 µm, 15 µm, 20 µm, 25 µm, 30 µm, 40 µm, 50 µm, 80 µm, 100 µm, 150 µm, 200 µm, 250 µm, 300 µm, 500 µm, 700 µm, 900 µm, 1 mm, 2 mm, 5 mm, 10 mm, or 20 mm or a combination thereof.

In certain embodiments, the number of cell clusters and/or islands contained within the patterned biomaterial can vary. In certain embodiments, the patterned biomaterial includes at least 1, 2, 3, 4, 5, 10, 15, 20, 25, 30, 35, 50, 100, 150, 200, 300, 400, 500, 1000, 10,000, 100,000, or 1,000,000 organized cell clusters and/or islands.

In certain embodiments, the properties of each cell cluster or island within a patterned biomaterial can differ. For example, each cell cluster or island of a patterned biomaterial can have different properties, such as diameter, density, shape, 3D organization, and pattern. In certain embodiments, the spacing between a subset of cell clusters or islands can differ from the spacing between another subset of cell clusters or islands. In certain embodiments, the 3D arrangement or pattern of a subset of cell clusters or islands can differ from the 3D arrangement or pattern of another subset of cell clusters or islands. In certain embodiments, the density, shape, or diameter of a subset of cell clusters or islands can differ from the density, shape, or diameter of another subset of cell clusters or islands.

In certain embodiments, sections of the patterned biomaterial can contain one or more cell clusters or islands of different alignments. For example, in one section of the patterned biomaterial, the one or more cell clusters or islands can be organized in the same plane of the patterned biomaterial, and in a different section of the patterned biomaterial, the one or more cell clusters or islands can be organized in a different plane of the patterned biomaterial.

In certain embodiments, each cell cluster or island of the patterned biomaterial can be comprised of a different cell type. For example, one cell cluster or island of the patterned biomaterial can be comprised of endothelial cells and another cell cluster or island of the same patterned biomaterial can be comprised of pancreatic beta-islet cells.

In certain embodiments, the patterned biomaterial can contain one or more cords and one or more cell clusters or islands. In certain embodiments, the arrangement and organization of the one or more cords and the one or more one cell clusters of the patterned biomaterial can vary. For example, the spacing between the one or more cords can differ from the spacing between the one or more cell clusters.

In certain embodiments, the one or more cell clusters or islands and the one or more cords of the patterned biomaterial can be comprised of different cell types. For example, the one or more cell clusters or islands of the patterned biomaterial can be comprised of neuronal cells and the one or more cords of the same patterned biomaterial can be comprised of endothelial cells. In certain embodiments, the one or more cell clusters or islands and the one or more cords of the patterned biomaterial can be comprised of the same cell type. For example, the one or more cell clusters or islands and the one or more cords of a patterned biomaterial can be comprised of endothelial cells.

In certain embodiments, the patterned biomaterial can include at least one cord and at least one cell cluster or island. In certain embodiments, the at least one cord can be organized in a different section of the patterned biomaterial than the at least one cell cluster. For example, one section of the patterned biomaterial can be comprised of the at least one cord, whereas another section of the patterned biomaterial can be comprised of the at least one cell cluster or island. In certain embodiments, the at least one cord and the at least one cell cluster or island can be organized in the same section of the patterned biomaterial.

In certain embodiments, the patterned biomaterial can contain one or more bioactive substances. Examples of bioactive substance(s) include, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the patterned biomaterial can include a biologically effective amount of VEGF and cords of endothelial cells.

In certain embodiments, the patterned biomaterial can be free from exogenous bioactive substances.

In certain embodiments, the patterned cords and/or clusters can contain no cells. For example, the patterned cords and/or clusters can contain no living cells. In certain embodiments, the cords can contain cell fragments and/or cell debris. In certain embodiments, the cords can contain extracellular matrix deposited by cells that were later removed and/or killed. In certain embodiments, the cords can contain a naturally-derived and/or synthetic scaffolding in the absence of cells, or fragments thereof. For example, a naturally-derived and/or synthetic scaffolding can be added to the 3D template, in the absence of cells, to form cords or clusters of the present disclosure.

In certain embodiments, the patterned cords and/or clusters can contain cells that are then removed, killed, or otherwise eliminated by known methods in the art, and the remnant biomaterial retains biological activity.

In certain embodiments, the patterned cords and/or clusters can contain cells that are then out-competed, replaced, displaced or removed during the process of host integration.

The ECM Scaffold

In certain embodiments, the ECM scaffold of the patterned biomaterial of the present disclosure can include any native or synthetic extracellular matrix material. In certain embodiments, the ECM scaffold can have one or more native and/or synthetic matrix materials.

In certain embodiments, the ECM scaffold can include peptides, proteins, carbohydrates, collagen, fibrin, fibrinogen, matrigel, agarose, polyethylene glycol, dextran, hyaluronic acid, or a combination thereof. For example in certain embodiments, the ECM scaffold can include collagen or fibrin.

In certain embodiments, the ECM scaffold can include a physical solid support such as silicone rubber, plastics, glass, hydroxyappetite, poly-lactic acid, poly-glycolic acid, or other materials.

In certain embodiments, where the patterned biomaterial is used to aid vascularization, fibrin can be used as the ECM scaffold material. Other suitable ECM materials can be used as a scaffold, depending on the specific purpose for the implant and based on the properties of the ECM material, including but not limited to, the degradation properties of the ECM materials.

In certain embodiments, the ECM scaffold can be degradable upon exposure to environmental conditions. For example, the ECM scaffold can be degraded by the presence of hydrolytic enzymes, presence of proteasomal enzymes, pH lower than 5 and reducing conditions.

In certain embodiments, the ECM scaffold can have different properties, a different composition, or elicit different responses from the host cells than the naturally-derived or synthetic scaffolding used to form the cords and/or cell clusters or islands. For example, the naturally-derived or synthetic scaffolding used to form the cords and/or cell clusters or islands can degrade at a different rate than the ECM scaffolding. In certain embodiments, the naturally-derived or synthetic scaffolding used to form the cords and/or cell clusters or islands degrades faster than the ECM scaffolding.

In certain embodiments, the naturally-derived or synthetic scaffolding used to form the cords and/or cell clusters or islands can release bioactive substances compared to the ECM scaffold. For example, naturally-derived or synthetic scaffolding used to form the cords and/or cell clusters or islands can release pro-angiogenic factors.

In certain embodiments, the composition of the ECM scaffold differs from the composition of the naturally-derived or synthetic scaffolding used to form the cords and/or cell clusters or islands. For example, the naturally-derived or synthetic scaffolding can contain collagen and the ECM scaffold can contain fibrin.

In certain embodiments, the composition of the ECM scaffold can be the same as the composition of the naturally-derived or synthetic scaffolding used to form cords and/or cell clusters or islands. For example, the naturally-derived or synthetic scaffolding and the ECM scaffold can both contain collagen.

In certain embodiments, the cords and/or clusters or islands of cells can be encapsulated in an ECM scaffold comprising cells of a distinct cell type. In certain embodiments, the ECM scaffold of the patterned biomaterial can be seeded with cells. In certain embodiments the ECM scaffold can be comprised of one or more cell types. Cells can confer tissue functionality and provide structures, which can replace or facilitate the repair of a tissue of the subject. For example, the ECM scaffold can include, but is not limited to, muscle cells to provide contractile structures, vascular and/or neural cells to provide conductive elements, metabolically active secretory cells, such as liver cells, hormone synthesizing cells, sebaceous cells, pancreatic islet cells or adrenal cortex cells to provide secretory structures, stem cells, such as bone marrow-derived or embryonic stem cells, dermal fibroblasts, skin keratinocytes, Schwann cells for nerve implants, smooth muscle cells and endothelial cells for vessel structures, urothelial and smooth muscle cells for bladder/urethra structures and osteocytes, chondrocytes, and tendon cells for bone and tendon structures, or a combination thereof. In certain embodiments, the ECM scaffold can include other cell types including, but not limited, to hepatocytes and chondrocytes.

In certain embodiments, the ECM scaffold can contain at least one cell of at least one cell type. For example, the ECM scaffold can contain at least one hepatocyte or at least one pancreatic beta-islet cell. In certain embodiments, the ECM scaffold can contain at least one cell of at least two cell types.

Cells suitable for inclusion in the ECM scaffold of the patterned biomaterial of the present disclosure can be derived from any suitable source. The subject to receive the implant of the patterned biomaterial of the present disclosure can determine the source of the cells to be included in the ECM scaffold. In certain embodiments, the cells can be derived from an autologous source. For example, the cells can be derived from the subject to be implanted with the patterned biomaterial. For example, epithelial cells can be derived from the skin of the subject to be implanted with the patterned biomaterial. In certain embodiments, the cells can also be generated from stem cells derived from various sources that are then differentiated into the desired cell type. For example, the stem cells can be derived from the subject to be implanted with the patterned biomaterial. In certain embodiments, cells can be cultured for a period of time under various conditions to induce certain phenotypes before placing the cells in the ECM scaffold.

In certain embodiments, the ECM scaffold can include an engineered tissue construct. For example, an engineered tissue construct can be encapsulated in the ECM scaffold.

In certain embodiments, the patterned biomaterial can be comprised of cords and/or clusters or islands of endothelial cells formed in a naturally-derived or synthetic scaffolding that is at least partially encapsulated in an ECM scaffolding comprising cells of a distinct cell type. For example, the ECM scaffolding can be seeded with cells, including, but not limited to, pancreatic cells, cardiac cells, skin cells muscles cells, fat cells, or bone cells.

In certain other embodiments, the patterned biomaterial of the present disclosure can be encapsulated within another biomaterial or engineered tissue.

In certain embodiments, the cords can be lifted out of their template and handled or used as a suspension of the cords without a separate ECM scaffold.

In certain embodiments, the cords of the patterned biomaterial of the present disclosure can be embedded in the ECM scaffold in a parallel arrangement. In certain embodiments, the cords can be embedded in the ECM scaffold in a non-parallel arrangement.

In certain embodiments, the ECM scaffolding can contain one or more bioactive substances. Examples of bioactive substance(s) include, but are not limited to, hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). For example, the patterned biomaterial can include a biologically effective amount of VEGF. In certain embodiments, the ECM scaffolding can contain at least one cell of one cell type and at least one bioactive agent.

In certain embodiments, the ECM scaffolding can be free from exogenous bioactive substances.

Applications Using the Patterned Biomaterials

In certain embodiments, the patterned biomaterial of the present disclosure can be implanted in a subject. Non-limiting examples of non-human subjects include non-human primates, dogs, cats, mice, rats, guinea pigs, rabbits, fowl, pigs, horses, cows, goats, sheep, etc. In certain embodiments, the subject can be any animal. In certain embodiments, the subject can be any mammal. In certain embodiments, the subject can be a human. For example, in certain embodiments, the patterned biomaterial of the present disclosure can be implanted in a subject by suturing the patterned biomaterial to fat pads in the lower abdomen.

In certain embodiments, the patterned biomaterial of the present disclosure can be used to enhance vascularization in ischemic settings, such as, by acting as a conduit to increase blood flow to regions of tissues that are not receiving sufficient blood supply. In certain embodiments, the patterned biomaterial of the present disclosure can be implanted in a region of a subject that requires an increase in blood flow. For example, the patterned biomaterial can be implanted in and/or near an ischemic tissue. In certain embodiments, the patterned biomaterial can be implanted to treat cardiac ischemia. The patterned biomaterial can be implanted to revascularize from healthy coronary circulation or neighboring non-coronary vasculature.

In certain embodiments, the patterned biomaterial of the present disclosure can be used as a novel adjunct to coronary artery bypass grafting (CABG) in addressing cardiac ischemia. In certain embodiments, during CABG surgery, a surgeon can apply the patterned biomaterial of the present disclosure across regions of incomplete reperfusion. For example, the patterned biomaterial can be placed in order to revascularize from healthy coronary circulation or neighboring non-coronary vasculature (such as circulation from the left internal mammary artery) into the ischemic zone unlikely to be addressed by the CABG procedure.

In certain embodiments, the patterned biomaterial can be used a "directional microbypass" for revascularizing ischemic myocardium not amenable to traditional therapies. In many patients that suffer from acute myocardial ischemia and in another even larger cohort of patients with untreatable coronary disease, there remain areas of viable heart that are not revascularized. In certain embodiments, the patterned biomaterial can potentially revascularize those inaccessible ischemic zones in these patients. The pre-patterned cords of the patterned biomaterial can stimulate and spatially direct revascularization and thus can form a "vascular bridge" from nearby unobstructed coronary vasculature to around and beyond a coronary obstruction leading to micro-perfused distal myocardium to protect cardiomyocytes viability and function.

Figure 6:
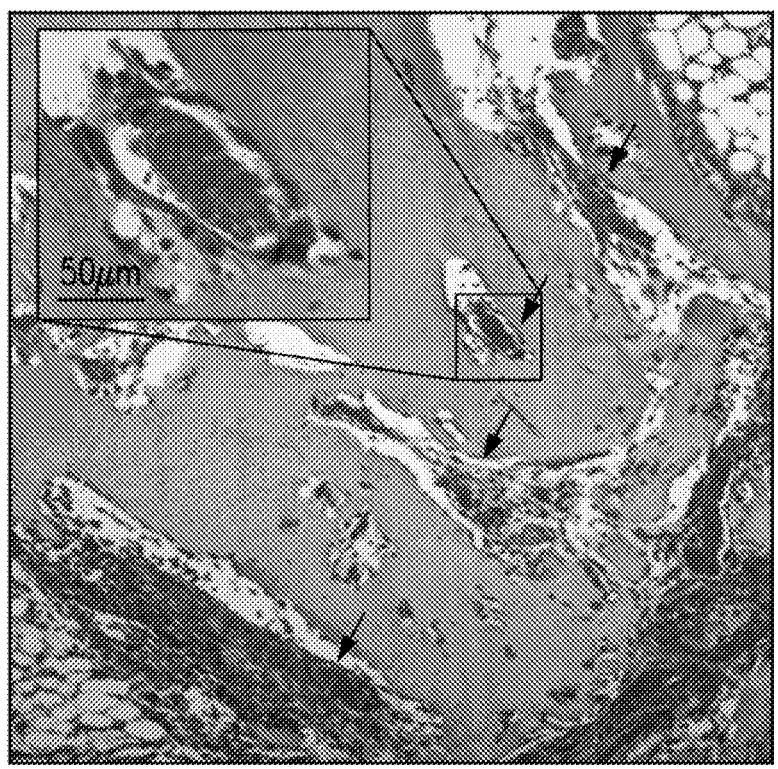
FIG. 6 depicts H&E stain of a network of ECs in parallel cords. Blood flow is evident in pre-patterned locations 5 days post implantation (arrows).

The patterned biomaterial of the present disclosure can enhance neovascularization as well as influence vascular architecture through two potential mechanisms. The embedded cords themselves can be incorporated into new capillary networks. Furthermore, embedded cords can deposit additional matrix and secrete growth factors into the scaffold thereby providing a microenvironment that more closely mimics that of native tissue. The patterned biomaterial of the present disclosure is capable of enhancing neovascularization by spatially guiding the invading sprouts of an angiogenic capillary network upon implantation, without incorporation into the nascent vessels. ECM scaffolds embedded with simple patterns of parallel cords display internal blood flow five days post-implantation in vivo (FIG. 6)—significantly faster than unpatterned constructs which typically take 7-14 days to become perfused (9). Co-linearity of the blood-filled cross-sections of the lumens suggests that the cords of the patterned biomaterial of the present disclosure provide guidance for invading vascular sprouts from the native tissue. Thus, the patterned biomaterial of the present disclosure can be used in conjunction with various types of engineered tissue constructs to aid in the vascularization of the engineered tissue construct.

In certain embodiments, the patterned biomaterials of the present disclosure can be useful in other applications in which it would be beneficial to have an engineered material to aid in spatially guiding the direction of host cell and tissue invasion. Such applications can include, but are not limited to, nerve regeneration. In certain embodiments, the components of the heterotypic cell suspension used to fabricate the cords of the present disclosure can be modified for a specific application. For example, for nerve regeneration applications, the cell suspension can include neurons, neuronal stem cells, or cells that are associated with supporting neuronal function, or a combination thereof. In certain embodiments, the patterned biomaterial can be used at a site of tissue damage, e.g., neuronal tissue damage.

In certain embodiments, the components of the ECM scaffold used to fabricate the patterned biomaterial of the present disclosure can be modified for a specific application. For example, for nerve regeneration applications, the ECM scaffold can include neurons, and the patterned biomaterial can be used at a site of tissue damage, e.g., neuronal tissue damage.

In certain embodiments, the patterned biomaterial of the present disclosure can allow for maintenance of the viability and proper function of an engineered tissue. For example, the patterned biomaterial can allow for maintenance of the viability and proper function of an engineered liver tissue. In certain embodiments, the patterned biomaterial of the present disclosure can be used to enhance the survival and function of hepatocytes within large engineered liver constructs upon implantation. Effective mass transport between the blood stream and the liver for metabolic needs relies on a precisely-defined microenvironment delineated by the paracrine and juxtacrine signaling between hepatocytes and endothelial cells. As such, the liver serves as an ideal model to study the interaction between organized endothelial networks and cellular function. In addition, the material can also be used to support function of many other engineered tissues including, but not limited to, bone, fat, muscle, heart, and pancreas.

In certain embodiments, the patterned biomaterial of the present disclosure can enhance wound healing. In certain embodiments, the patterned biomaterials can be useful in the treatment of chronic wounds such as, for example, diabetic foot ulcers. Additionally, the patterned biomaterial of the present disclosure can be useful in the treatment of wounds sustained during military combat. In certain embodiments, the patterned biomaterial can be implanted in a subject to treat peripheral vascular disease, diabetic wounds, and clinical ischemia.

In certain embodiments, the patterned biomaterial of the present disclosure can be used to enhance repair of various tissues. Examples of tissues that can be treated by the patterned biomaterial of the present disclosure includes, but is not limited to, skeletal muscle tissue, skin, fat tissue, bone, cardiac tissue, pancreatic tissue, liver tissue, lung tissue, kidney tissue, intestinal tissue, esophageal tissue, stomach tissue, nerve tissue, spinal tissue, and brain tissue.

In certain embodiments, a method of vascularizing a tissue of a subject includes providing a patterned biomaterial comprising organized endothelial-based cords and implanting the patterned biomaterial into a tissue of the subject, wherein the biomaterial promotes increased vascularity and perfusion in the subject.

To facilitate a better understanding of the present disclosure, the following examples of certain aspects of some embodiments are given. In no way should the following examples be read to limit, or define, the entire scope of the disclosure.

EXAMPLES

Example 1: Methods of Fabricating Patterned Biomaterial

Poly (dimethylsiloxane) (PDMS) stamps with topographical channels were molded from a microfabricated silicone master. These PDMS channels were seeded with human umbilical vein endothelial cells (HUVECs) and mouse mesenchymal stem cells (10T1/2s) that are suspended in liquid collagen. The collagen was subsequently polymerized, growth medium containing VEGF and bFGF was added, and the constructs were incubated over night, resulting in the formation of cords within 6-8 hours. Once the cords were formed, they were removed from the PDMS and embedded in a fibrin matrix [2]. This technique resulted in spatially organized networks of endothelial cell tubules, with clearly defined lengths, positions, and branching architectures (FIGS. 5, B and C). CD31 staining confirmed proper endothelial cell junctions and lumen formation, α smooth muscle actin staining demonstrates the perivascular localization of the 10T1/2 cells and confirms their differentiated state (FIG. 5D).

Figure 3:
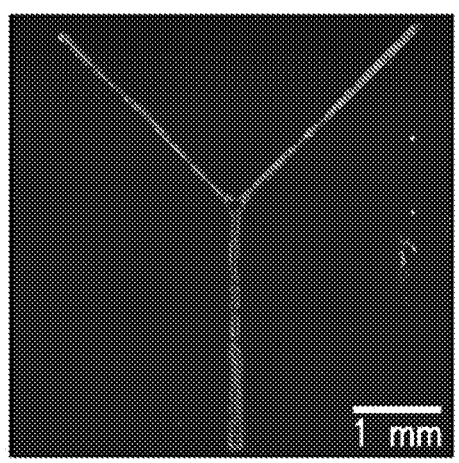
FIG. 3 is an image of comparing implanted cord architecture to the resulting in vivo host vasculature post-implantation.
Figure 3:
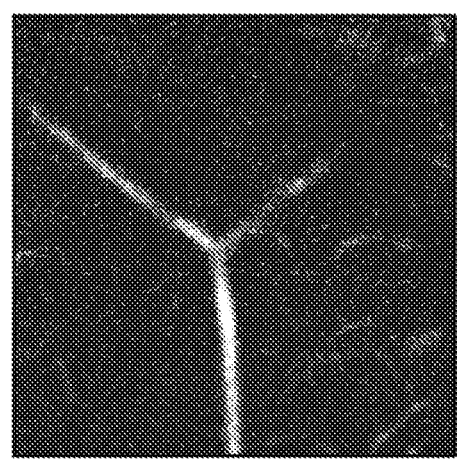

Altering the geometry of the PDMS molds allows the generation of a variety of geometries of EC cords (FIG. 3A). Upon implantation of these various cord geometries, the subsequent patterning of vessels was verified in vivo via tail vein injection of FITC-dextran (FIG. 3B). Sham injections and EC constructs with randomly seeded cells showed no visible patterning in vivo.

Figure 19:
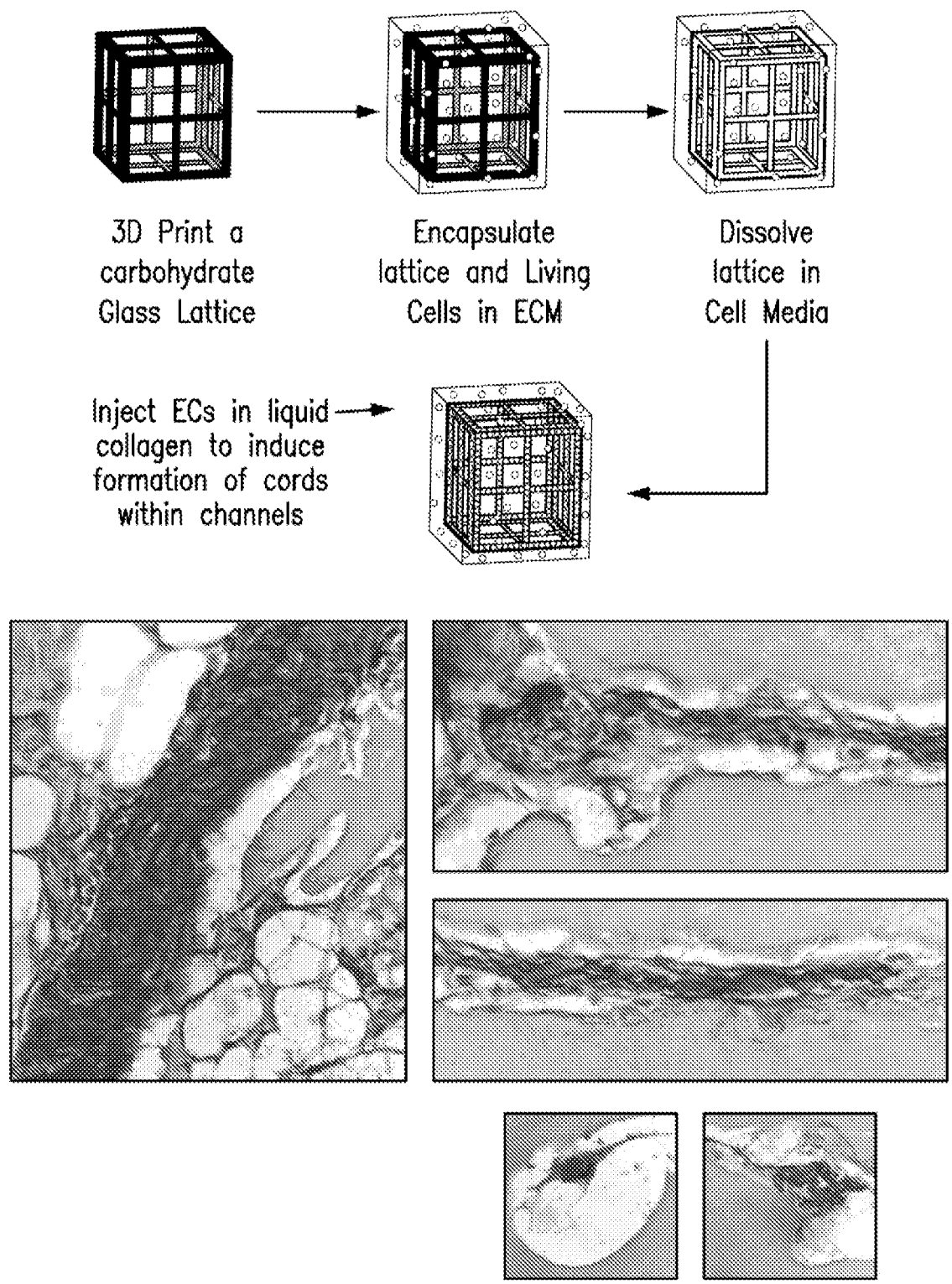
FIG. 19 shows a certain embodiment by which the patterned biomaterial can be generated.

In addition, 3D printed sugar lattices can be used to generate a patterned biomaterial. Endothelial cells suspended in liquid collagen can be placed into channels created by 3D printed sugar lattices to form cords within the channels (FIG. 19). The sugar lattice was created using 3D printing technology to generate a carbohydrate glass lattice, and encapsulated in extracellular matrix (FIG. 19). The lattice was dissolved by incubation in cell media to create channels within the ECM scaffold. Endothelial cells suspended in liquid collagen were injected in the channels to form cords within the channels (FIG. 19). Upon implantation, these cords incite a vascularization response similar to the original protocol for making cords (FIG. 19). Capillaries are formed around the circumference of the collagen core. These results indicate that 3D printing technology can be used for rapid scaleup of the cord technology for clinical and translation purposes.

Example 2: Inducement of Vivo Vessel Formation

Figure 1B:
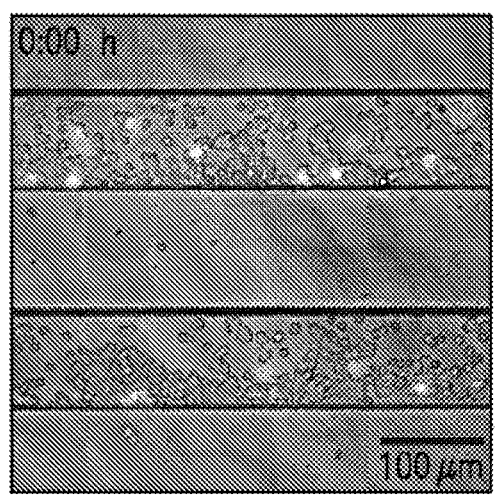
Figure 1B:
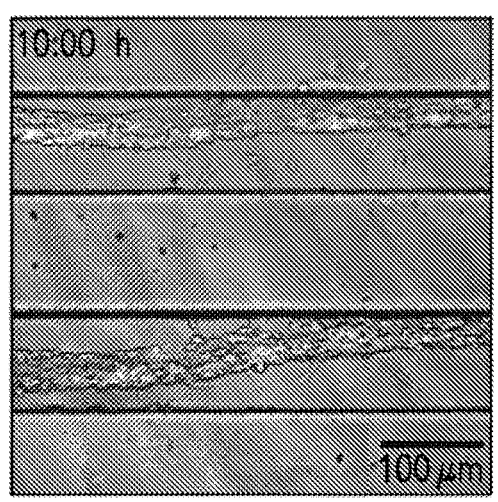
Figure 1C:
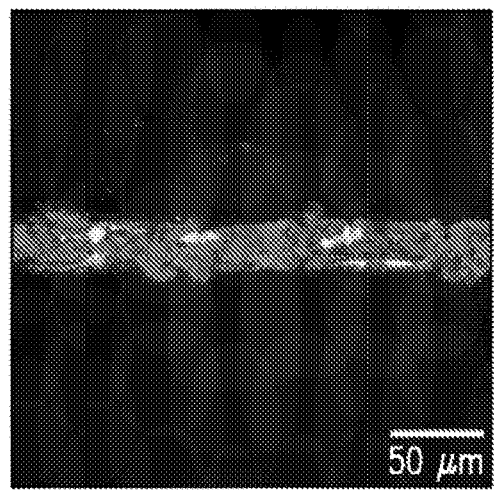
Figure 1D:
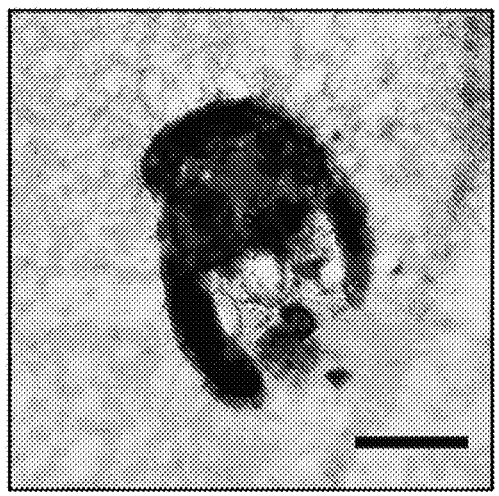
Figure 1D:
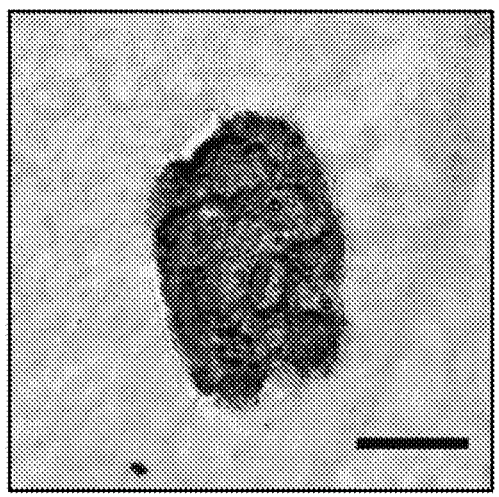
Figure 1E:
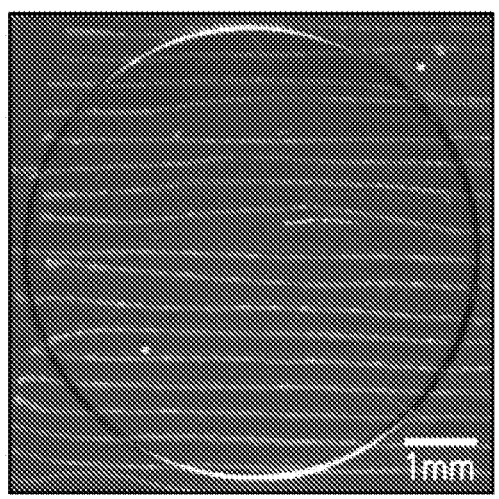

To test whether patterned endothelial cell (EC) cords induce vivo vessel formation in vivo, EC cords embedded in a fibrin matrix were implanted into the intraperitoneal space of nude mice (schematic, FIG. 1A). The cords were first prepared by seeding HUVECs and 10T1/2 cells suspended within collagen pre-polymer into a PDMS template and allowed to contract and remodel the collagen over a period of 4 hours. During this maturation period, the cells contracted against the matrix and each other, which caused the cords to shrink in diameter to approximately 50% of their original size (FIG. 1B). The HUVECs and 10T1/2 cells were mobile within the cords and also underwent some sorting during this time, with many of the 10T1/2 localizing to the periphery of the cords (FIG. 1C). Inhibiting cytoskeletal tension by treating the cords with the myosin IIa inhibitor blebbistatin prevented their contraction and elongation of the cells along the collagen. H&E and Sirius red staining of cords embedded in paraffin and sectioned revealed that the cells tend to cluster and wrap around the collagen rather than being uniformly distributed throughout the cords (FIG. 1D). After allowing the cords to contract, they were embedded into a larger fibrin gel (FIG. 1E) and prepared for implantation by attaching the samples to a polypropylene surgical mesh. The cords were implanted adjacent to a fat pad into athymic mice and resected at various time points. Tissues resected after 7 days, sectioned and stained with H&E indicated the presence of blood in areas where EC cords were initially present (FIG. 1F). Injection of FITC-dextran via the tail vein at day 14 demonstrates that the newly formed vessels are patent and successfully anastomose with the host circulation (FIG. 1g).

Figure 2A:
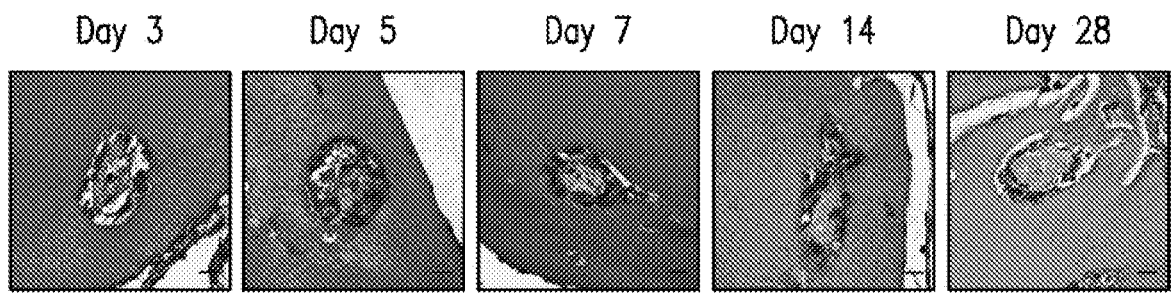
FIGS. 2A-2B depict H&E staining of resected tissues, indicating the presence of blood vessels at the sites where cords were and that these vessels contained blood.
Figure 2B:
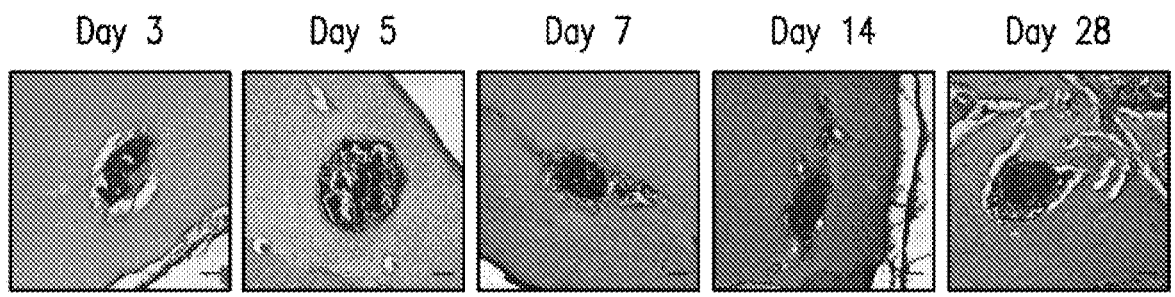

H&E staining of resected tissues showed the presence of blood as early as 3 days post implantation (FIG. 2A). Lots of blood was present at 5 days. Vessel-like structures were present at day 7 and become more organized at days 14 and 28. Sirius red and fast green staining demonstrated the persistence of the implanted collagen throughout the entire time course of the study (FIG. 2B).

The identity of the cells lining the vessel walls was confirmed via immunostaining against mouse and human CD31, and the presence of red blood cells within the lumens of the vessels was confirmed via immunostaining for ter-119. Some capillaries also displayed a mature phenotype via the presence of perivascular a-SMA-positive cells.

Example 3: Implantation of Liver Hepatocytes with EC Cords in Mice

Figure 4A:
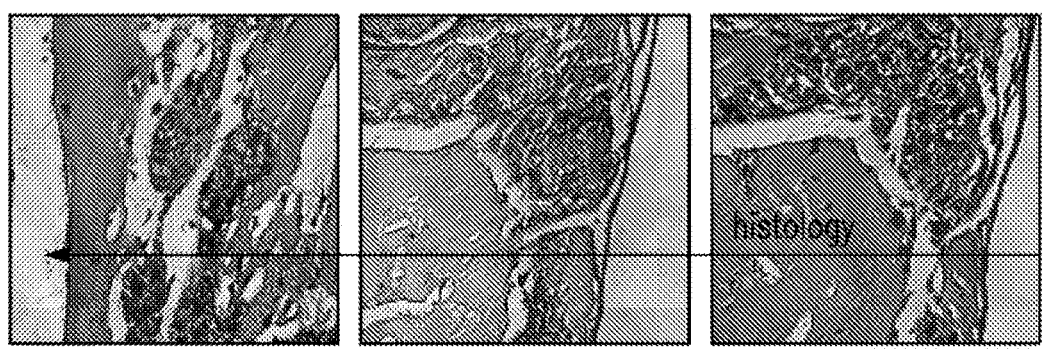
FIGS. 4A-4C depict the results of a study indicating the enhanced function of implanted liver hepatocytes using the cords of the present disclosure in mice.
Figure 4B:
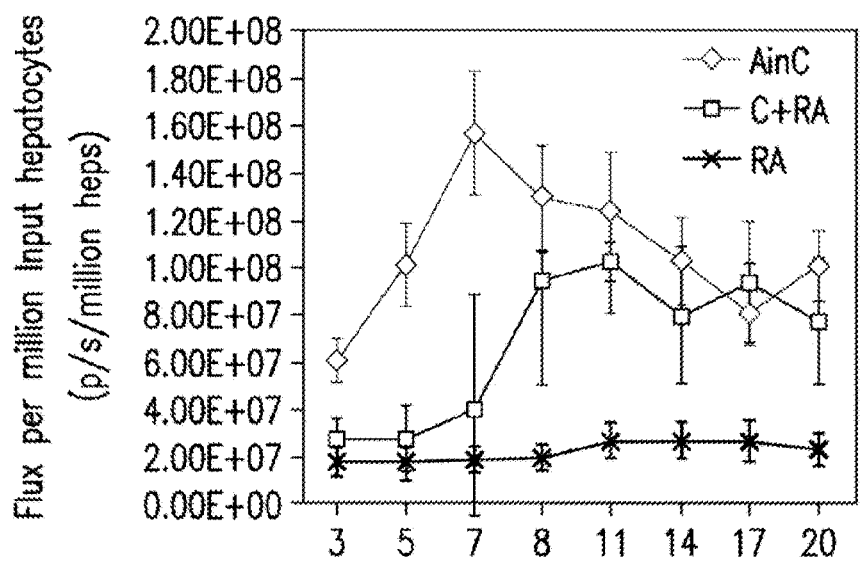
Figure 4C:
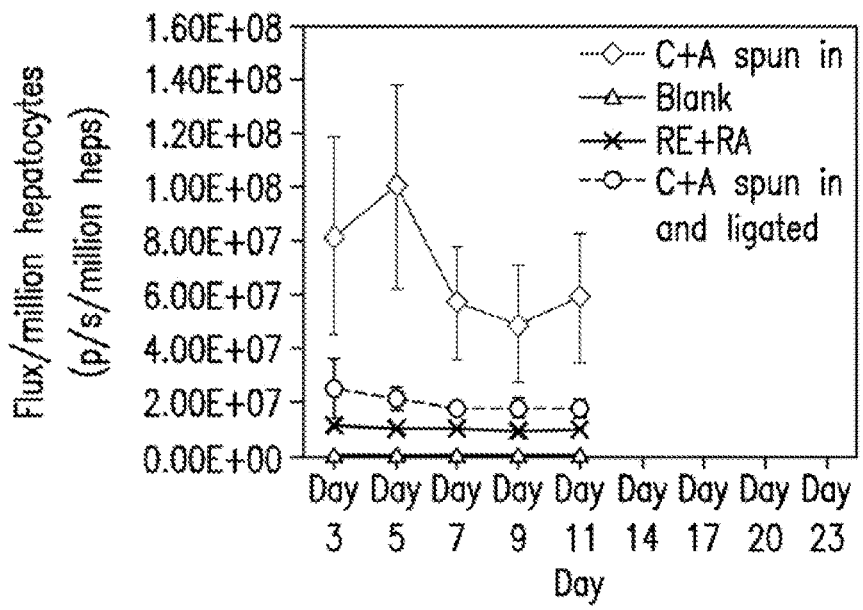

To demonstrate the ability of this vascular patterning approach to be applied to engineering functional tissues, liver hepatocytes were co-implanted with EC cords into mice. The constructs were generated by first patterning EC cords as usual. Prior to removal from the PDMS molds, however, primary rat hepatocytes were either spun down into the wells with the EC cords or left suspended throughout the fibrin gel. Prior to embedding within the constructs, the hepatocytes were transduced with a lucerifase construct under the control of the albumin promoter. Thus, whole animal imaging was used to track the viability and ability of the hepatocytes to produce albumin as shown in FIG. 4. These data indicate that vessels formed upon implantation of EC cords and were able to effectively support the ability of the hepatocytes to produce albumin in an engineered tissue.

Example 4: Geometric Control of Vascular Network to Enhance Engineered Tissue Integration and Function Materials and Methods Cell Culture. Primary human umbilical endothelial cells (HUVECs; Lonza) were maintained on 0.1% (wt/vol) gelatin-coated dishes in EGM-2 (Lonza). C3H10T1/2 cells (ATCC) were maintained in low-glucose DMEM containing 10% (vol/vol) FBS (Atlanta Biologicals), 100 U/mL penicillin, and 100 mg/mL streptomycin (Invitrogen). Primary human hepatocytes from a 1-year-old female Caucasian donor (Lot Hu8085; CellzDirect) were maintained in high-glucose DMEM (Cellgro) containing 10% (vol/vol) FBS (Gibco), 1% (vol/vol) ITS (insulin, transferrin, sodium selenite) supplement (BD Biosciences), 0.49 pg/mL glucagon, 0.08 ng/mL dexamethasone, 0.018 M Hepes, and 1% (vol/vol) penicillin-streptomycin (pen-strep; Invitrogen). Primary rat hepatocytes were isolated as described previously (51-54) and maintained in high-glucose DMEM containing 10% (vol/vol) FBS, 0.5 U/mL insulin (Lilly), 7 ng/mL glucagon (Bedford Laboratories), 7.5 µg/mL hydrocortisone (Sigma-Aldrich), and 1% (wt/vol) pen-strep. J2-3T3 fibroblasts (gift from Howard Green, Harvard Medical School, Boston) were maintained in high glucose DMEM containing 10% (vol/vol) bovine serum and 1% (wt/vol) pen-strep. Human hepatoma (Huh-7.5) cells (gift from Charles Rice, The Rockefeller University, New York) were maintained in high-glucose DMEM containing 10% (vol/vol) FBS (Atlanta Biologicals), 100 U/mL penicillin, and 100 mg/Ml streptomycin (Invitrogen) and used for in vitro imaging of hepatic constructs instead of primary hepatocytes.

Micropatterning of Endothelial cell cords. EC cords were micropatterned as previously described (2). HUVECs and 10T1/2s were suspended at a ratio of 50:1 in 2.5 mg/mL liquid collagen (BD Biosciences) and centrifuged into PDMS channels pretreated with 0.01% Pluronic F-127. Excess unpolymerized collagen and cells were removed by dewetting the surface of the substrate. The collagen was polymerized, growth medium was added, and constructs were incubated for 4-6 h. The newly formed cords were removed from the PDMS substrates by inverting onto a drop of unpolymerized 7.5 mg/mL bovine fibrin (Sigma-Aldrich). After the fibrin was polymerized, the PDMS was removed, and a second layer of unpolymerized fibrin was added and polymerized to fully encase the cords. The embedded cords were cut with a 6-mm biopsy punch before implantation. To include hepatocytes in the constructs, hepatic aggregates comprising ~100 hepatocytes and 25 J2 fibroblasts were formed in AggreWell micromodels overnight and suspended at a concentration of 15 K/mL in the fibrin gel. Random HUVEC conditions included $2 \times 10^6$ HUVECs per milliliter and 10T1/2s at a 50:1 ratio in fibrin. For decellularization, constructs were immersed in 8 mM CHAPS, 1M NaCl, and 25 mM EDTA in PBS and placed on an orbital shaker overnight. Excess cellular debris and detergent were then removed by soaking the constructs multiple times in PBS on an orbital shaker for several hours.

In Vivo Implantation of Constructs. To preserve geometry during implantation, constructs were embedded in a gasket cut from a polypropylene surgical mesh (Davol). Eight-week-old female Nu/nu nude mice (Charles River) or NCr nude mice (Taconic) were anesthetized using isoflurane, and the constructs were sutured to the mesenteric parametrial fat pad. For "cords+hepatocytes–excised" animals, engineered tissue and attached mesentery were cut from the remainder of the mesentery via an upstream excision so that the tissue and attached mesentery were isolated from host circulation. The incisions were closed aseptically, and the animals were administered 0.1 mg/mL buprenorphine every 12 h for 3 d following surgery.

In Situ Imaging. To enable noninvasive imaging of cell function, hepatocytes were transduced with a lentiviral vector expressing firefly luciferase under the human albumin promoter (pTRIP.Alb.IVSb.IRES.tagRFP-DEST; gift of Charles Rice, The Rockefeller University, New York). For luminescence imaging, mice were intraperitoneal (i.p.) injected with 250 µL of 15 mg/mL D-luciferin (Caliper Life Sciences) and then imaged using the IVIS Spectrum system (Xenogen). To visualize perfused vessels, a solution of 20 mg/mL FITC-labeled dextran (150 kDa; Sigma) in PBS was injected intravenously (i.v.) via the tail vein. To visualize mouse vs. human vessels, a solution of 500 µg/mL lectin from Helix pomatia agglutinin (HPA) conjugated to Alexa 488 (Sigma-Aldrich), and 100 µg/mL lectin from Ulex europaeus agglutinin (UEA-1) conjugated to TRITC (Vector Laboratories) in PBS was injected i.v. via the tail vein. These lectins previously were demonstrated to bind specifically to mouse or human endothelial cells, respectively (55, 56). Perfused vessels subsequently were imaged using a Zeiss 710 laser scanning confocal microscope.

Tissue Harvesting, Processing, Histology, and Immunohistochemistry. Animals were killed at various time points, and tissue was harvested from the i.p. space. Explants were fixed in 4% (vol/vol) paraformaldehyde (PFA) for 48 h at 4° C., dehydrated in graded ethanol (50-100%), embedded in paraffin, and sectioned using a microtome (6 µm) for immunohistochemical staining. For gross visualization of tissue, sections were stained with hematoxylin and eosin (H&E). For identification of cords composed partially of collagen, sections were stained with Sirius red (collagen) and fast green (other tissue elements). For identification of vessels containing human endothelial cells, mouse endothelial cells, smooth muscle cells, and erythroid cells, sections first were blocked using M.O.M. Blocking Reagent (Vector Laboratories) and normal goat serum and then immunostained using primary antibodies against human CD31 (1:20; Dako), mouse CD31 (1:50; BD Biosciences), Ter-119 (1:100; BD Biosciences), and alpha-smooth muscle actin (1:100, Abcam), respectively. Signal was visualized after incubation with secondary goat anti-IgG1-Alexa 555, goat anti-rat-Alexa 488, and donkey anti-rabbit-Alexa 647 antibodies (Jackson ImmunoResearch). For identification of primary hepatocytes adjacent to vessels containing RBCs, sections were blocked using normal donkey serum then incubated with primary antibodies against arginase 1 (ARG-1, 1:400; Sigma-Aldrich) and Ter-119 and followed with species-appropriate secondary antibodies conjugated to Alexa 488 and 555. Images were obtained using a Zeiss 710 laser scanning confocal or Nikon 1AR Ultra-Fast Spectral Scanning confocal microscope.

Statistical Analysis and Quantification of Vascularization Parameters. Quantification was performed manually on imaged H&E sections using FIJI Open Source software. Blood area was quantified by measuring the total area of tissue containing blood within a cord. Measurements were normalized to averge cord area to compensate for oblique cutting angles. Vessel number was quantified by counting individual vessels within a cord and then normalized to the average cord area. Vessel diameter was quantified by measuring the diameter of individual vessels within a cord. Sections for quantification were chosen from the center of the constructs, and a minimum of three sections at least 150 µm apart were quantified per cord. All data are expressed as the mean±SE. Statistical significance was determined using a one-way ANOVA followed by Tukey's post hoc test for group comparisons.

Introduction

The development of a unique approach for rapidly creating spatially organized vascular architectures within engineered tissues in vivo is described herein. This approach uses micropatterning techniques to organize endothelial cells (ECs) into geometrically defined "cords," which, in turn, act as a template after implantation for the guided formation of patterned capillaries integrated with host tissue. Furthermore, the spatial patterning of vascular architecture within engineered hepatic tissues leads to significantly increased levels of albumin activity, a marker of differentiated hepatocyte function, for at least 3 wk in vivo compared with nonpatterned controls. These findings demonstrate that geometric control of vascular architecture modulates the function of engineered tissues and, therefore, has broad application in the translation of cell-based regenerative therapies.

Results

Figure 7A:
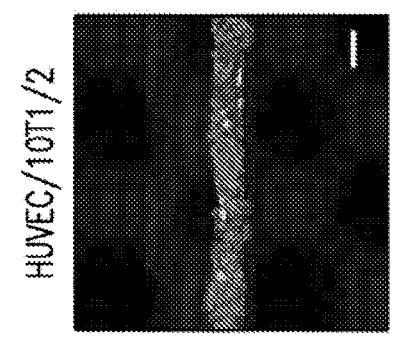
Figure 7B:
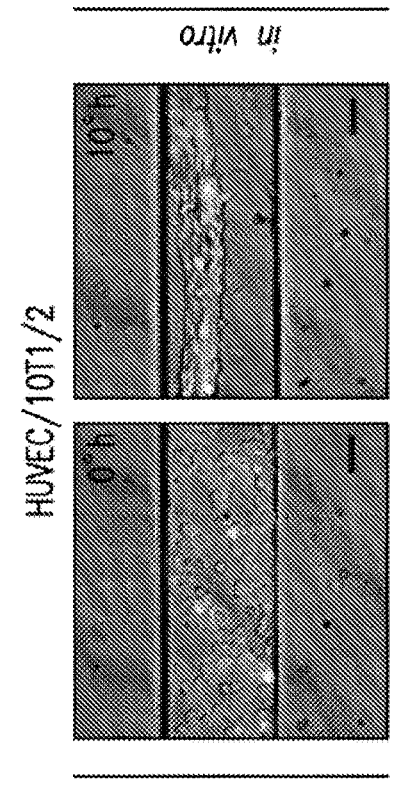
Figure 7C:
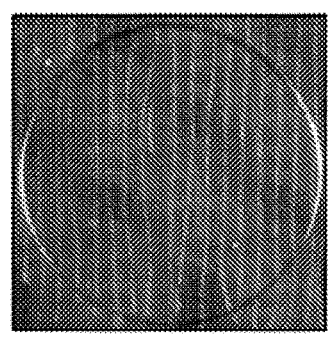
Figure 7D:
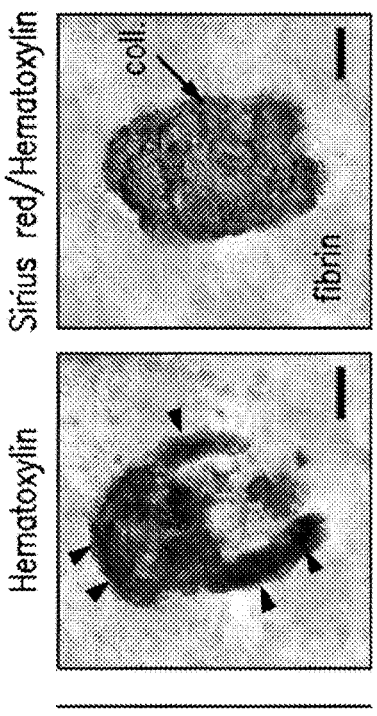
Figure 7E:
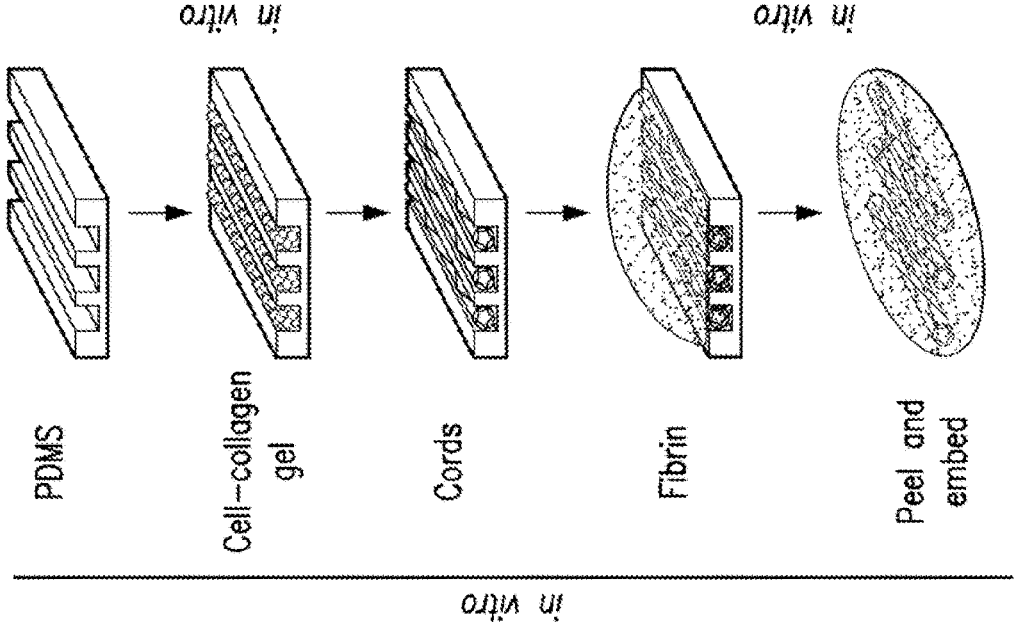
Figure 11A:
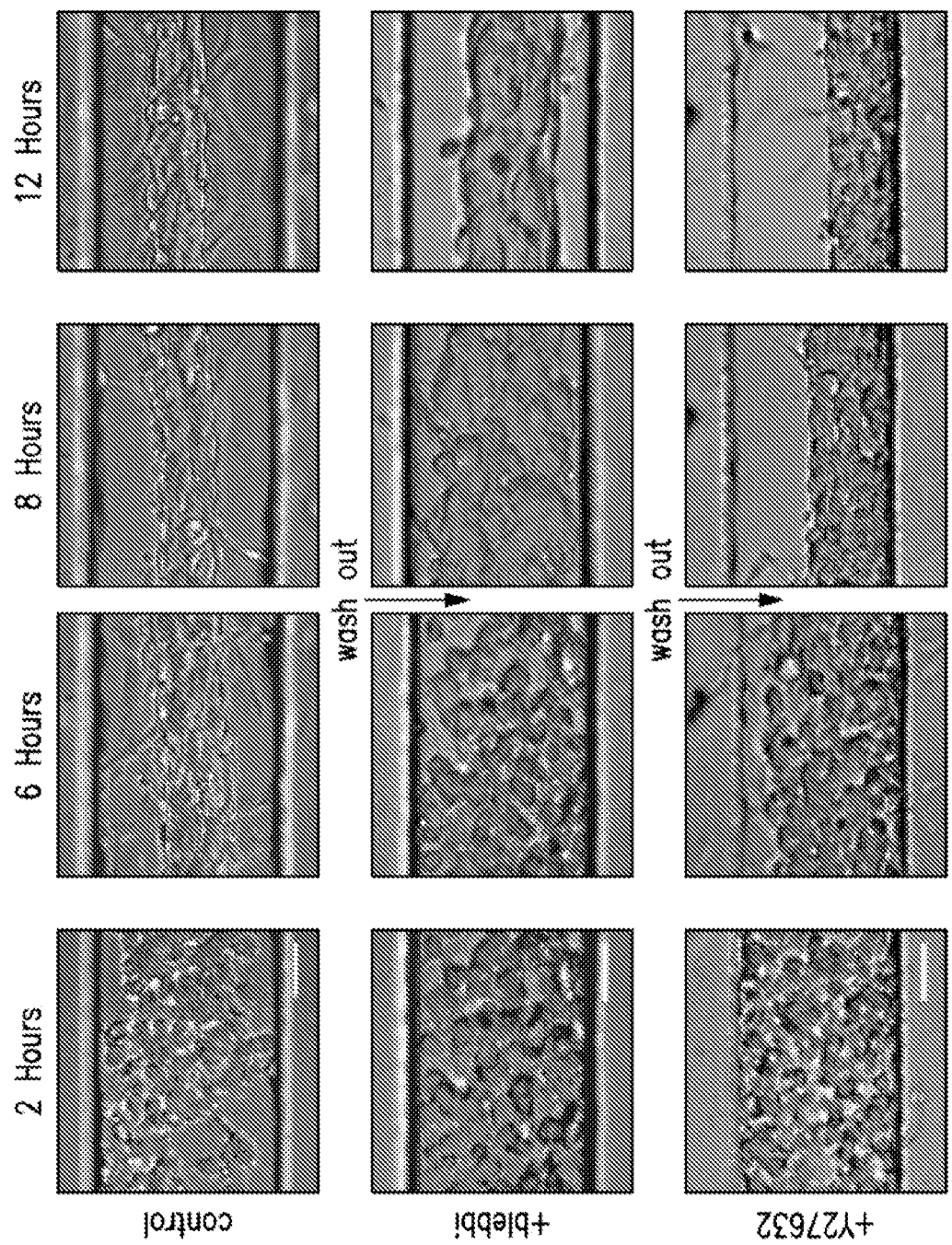
FIGS. 11A-11B show that cytoskeletal tension is required for cord contraction.
Figure 11B:
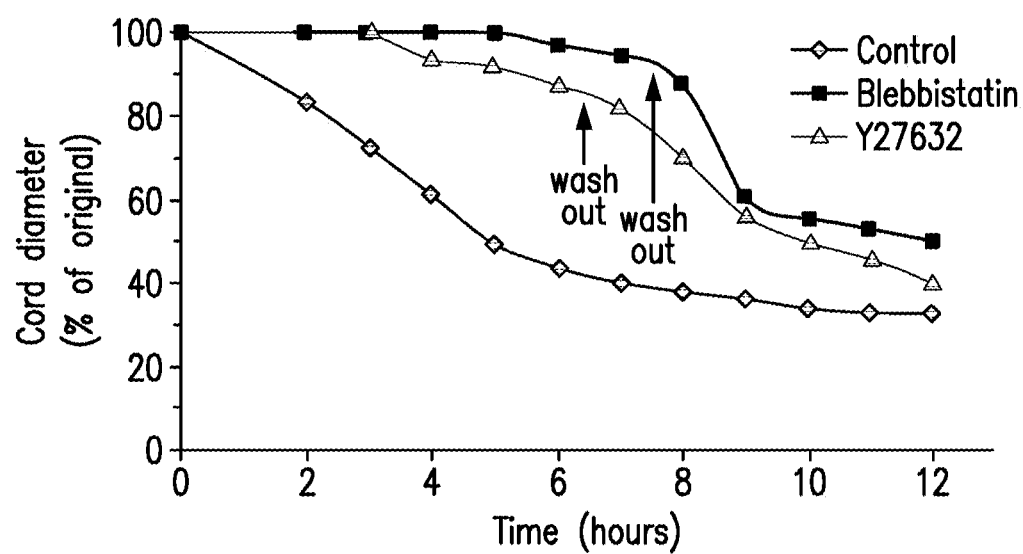

Patterned Assemblies of EC Cords Induces a Vascular Response. Adapting a previously developed approach (21, 2), geometrically defined cords of ECs that encase a collagen core were generated by seeding a suspension of human umbilical vein ECs (HUVECs) and mouse mesenchymal cells (C3H10T1/2) in liquid type I collagen into 150-µm-wide microchannels by centrifugation (FIG. 7A). After the collagen was polymerized and upon culture, the cells rapidly self-assembled into cords over approximately 4 h, during which they contracted to roughly 50% of their original diameter (FIG. 7B). This cord contraction was driven by myosin-mediated contractile activity, as cells treated with a nonmuscle myosin inhibitor (blebbistatin) or a Rho-associated protein kinase (ROCK) inhibitor (Y27632) immediately after seeding failed to form cords (FIG. 11). Time-lapse imaging of fluorescently labeled cells showed that the small population of 10T1/2s remained randomly distributed along the length of the primarily HUVEC cords throughout the contraction process (FIGS. 7B and C). Hematoxylin and eosin (H&E) and Sirius red staining of cross-sections of the fully formed, paraffin-embedded cords demonstrated clustering and wrapping of cells around a core of compacted collagen (FIG. 7D).

To test the ability of patterned EC cords to induce vascularization in vivo, cords were removed from the polydimethylsiloxane (PDMS) backing by first polymerizing a layer of fibrin over the top of the substrate, peeling the PDMS away to leave the cords on the surface of the fibrin layer, and then polymerizing a second layer of fibrin to fully encase the cords (FIGS. 7A and E). Following assembly, the constructs were sutured directly to the parametrial fat pad in the intraperitoneal (i.p.) space of athymic mice (FIG. 7F) and resected after 7 d. Histological staining of the paraffin-embedded tissues demonstrated the presence of collagen-rich, cell-laden structures within the fibrin implant that were organized spatially in a pattern mimicking the original position of the implanted cords (FIG. 7G). Higher magnification of these remnant cords indicated the presence of blood in the cell-rich regions around the perimeter alongside the axis of the cords, suggesting a directed vascularization response (FIG. 1H).

Figure 8A:
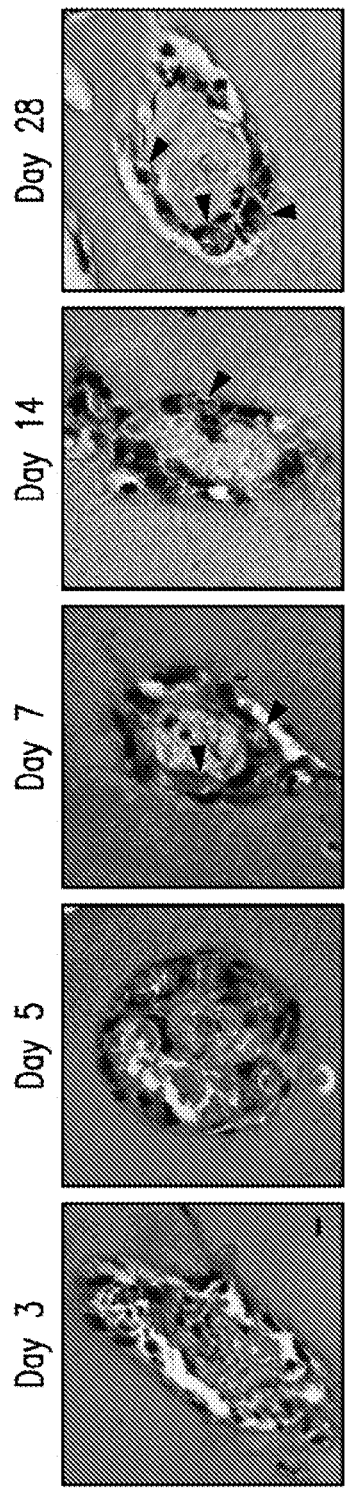
Figure 8B:
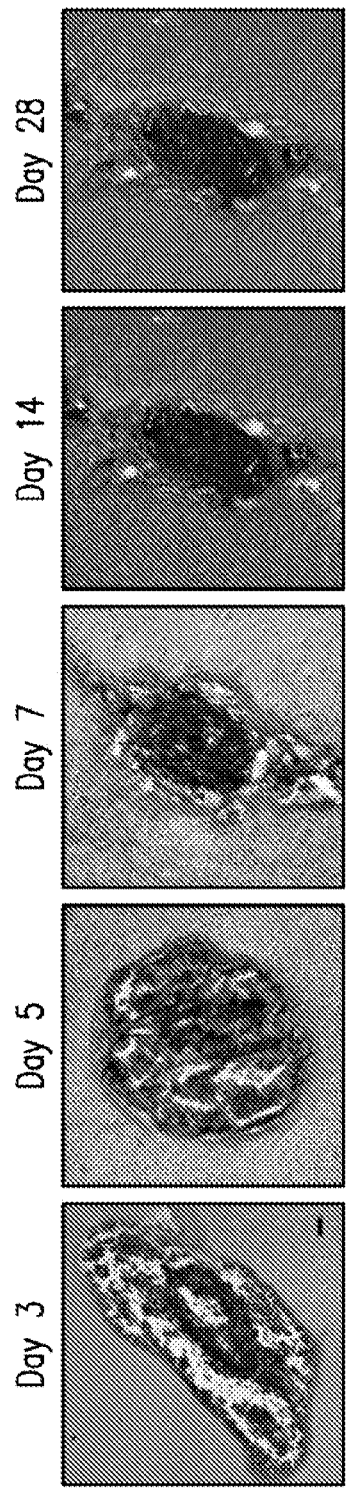
Figure 8C:
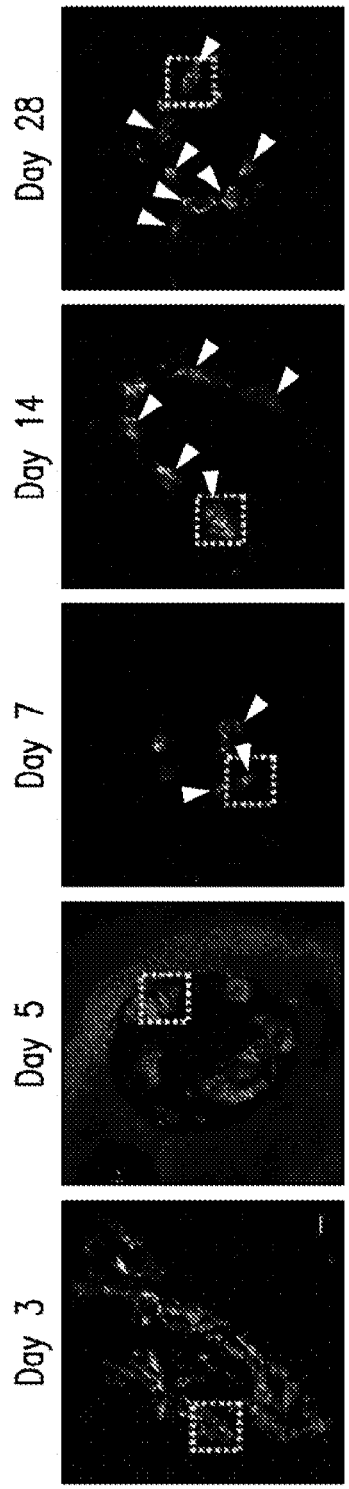
Figure 8D:
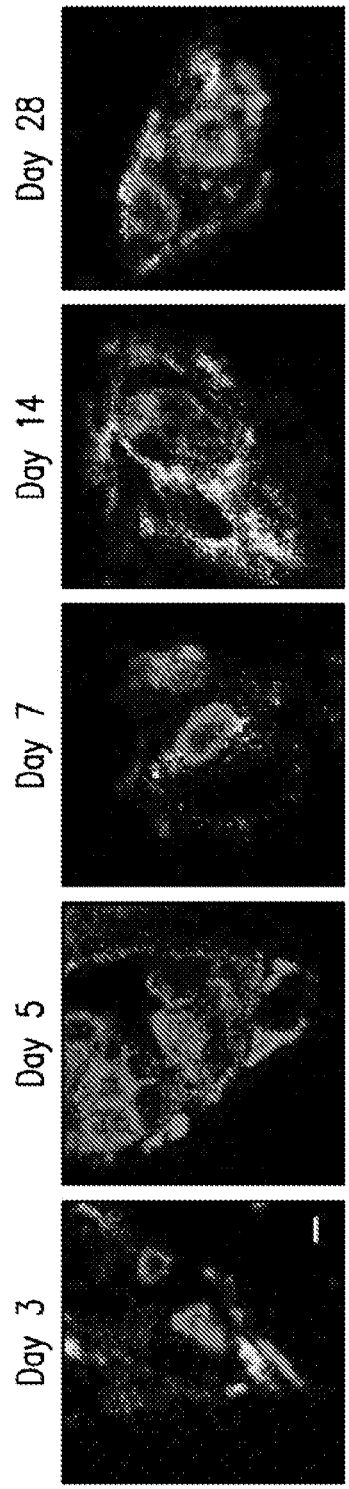

Recapitulation of Rudimentary Vessel Maturation Occurs Along Implanted Cords to Result in New Capillaries. To further characterize the blood vessel formation process resulting from the implantation of cords, tissue constructs were harvested at days 3, 5, 7, 14, and 28 post implantation (PI). H&E staining of resected tissues suggested the presence of red blood cells (RBCs) around the perimeter of cords as early as 3 d PI (FIG. 8A). Large areas of blood were present at 3 and 5 d PI and were surrounded by a fragmented layer of cells, reminiscent of the pattern observed in leaky vasculature. Loose cellular structures were replaced over time by a smaller, more definitive vessel-like cellular lining stereotypical of mature microvessels that persisted at least out to 28 d PI. Sirius red/fast green staining demonstrated the presence of collagen within the cords throughout the entire time course (FIG. 8B). To confirm the presence of RBCs and evaluate whether the ECs were of human origin, tissue sections were immunohistochemically stained for Ter-119, an erythroid cell marker, and human-specific CD31 (FIG. 8C). Ter-119 staining confirmed the presence of RBCs at all time points in localized patterns matching those previously observed with H&E staining. Human ECs circumscribed the RBCs and were found at all stages of the process, suggesting the formation of blood vessels containing ECs of human origin. These vessels appeared large and poorly organized at days 3 and 5 PI, but rapidly remodeled into smaller, lumenized capillaries that were evident as early as 7 d PI and persisted until at least 28 d PI. Staining for alpha-smooth muscle actin (α-SMA) revealed the presence of α-SMA-positive cells in a perivascular localization as early as day 3 (FIG. 8D).

As nascent vessels reorganized into smaller capillaries, the α-SMA-positive cells were tightly associated with adjacent ECs, suggesting a pericyte phenotype. To better assess the dynamics of vessel remodeling, the surface area of blood, the total number of vessels, and the diameter of vessels in H&E-stained sections were quantified. This quantification suggested that the maturation of capillaries occurred primarily between days 5 and 7 PI, during which (i) the area of blood within cords decreased from ~65% to 25% of the total cord area, (ii) the number of capillaries per cord increased from ~0.5 to 4.0, and (iii) the average vessel diameter decreased from ~30 µm to 7 µm (FIG. 2E; $P<0.05$). All trends continued until at least 28 d PI. Not limited to a specific theory, these results suggest that engineered cords anastomose quickly (by day 3 PI) with the host vasculature to form large, nascent vessels that later lumenize and reorganize into smaller, more numerous, and mature capillaries that are organized spatially around and alongside the collagen core of the endothelial cords.

Figures 12A, 12B, 12C:
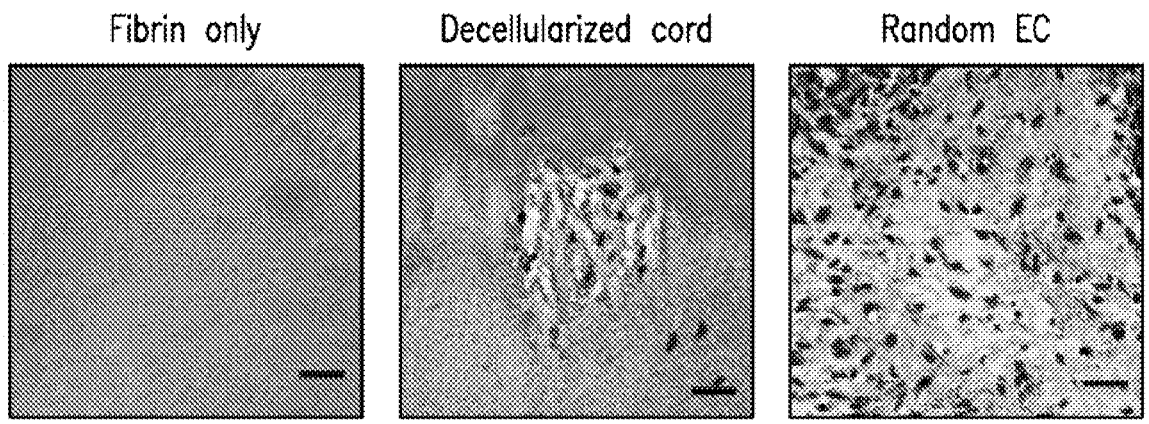
FIGS. 12A-12C show that cells are required for vascularization.

The vascularization response appeared to be specific to the cords, as implanted acellular, control fibrin gels remained absent of cells and showed no evidence of blood at 7 d PI (FIG. 12A). To determine whether cells within the engineered cords were required only for the in vitro assembly of the cord matrix and not necessary during implantation to elicit the vascularization response, tissue constructs were implanted that included fibrin gels containing cords that had been "decellularized" via treatment with CHAPS detergent before implantation. These gels retained the matrix structure of the cords, but cells were removed. Analysis of decellularized cords post implantation indicated the presence of small nuclei or DNA fragments near areas of collagen matrix, but no blood was evident (FIG. 12B). These results indicate that living cells within the cords were required for the biological activity of the constructs.

To study the impact of cellular organization within the implant on the vascularization response, fibrin gels containing randomly seeded HUVECs and 10T1/2s that had been precultured for 7 d in vitro were generated and implanted. Gels resected 7 d PI suggested the formation of a small number of capillaries limited to the periphery of the constructs penetrating no more than several hundred microns toward the core (FIG. 12C). In contrast, cord-containing constructs exhibited the presence of blood and vessels throughout the length of the cords. Notably, optimized random controls required $2\times10^6$ cells per milliliter, more than an order of magnitude more cells per implant than the patterned cord implants. These results demonstrate that viable endothelial and mural cells, as well as geometric definition of cord structure, contribute to the robust vessel formation and graft-host integration.

Figure 9A:
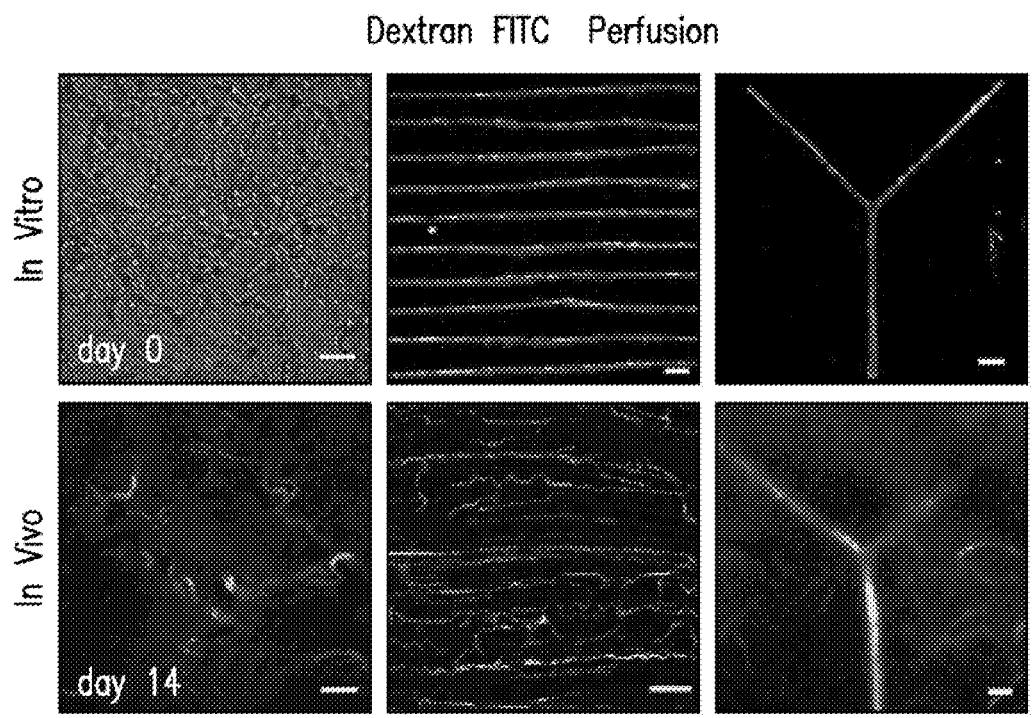
FIGS. 9A-9B show that patterned EC cords integrate with host vasculature.
Figure 13:
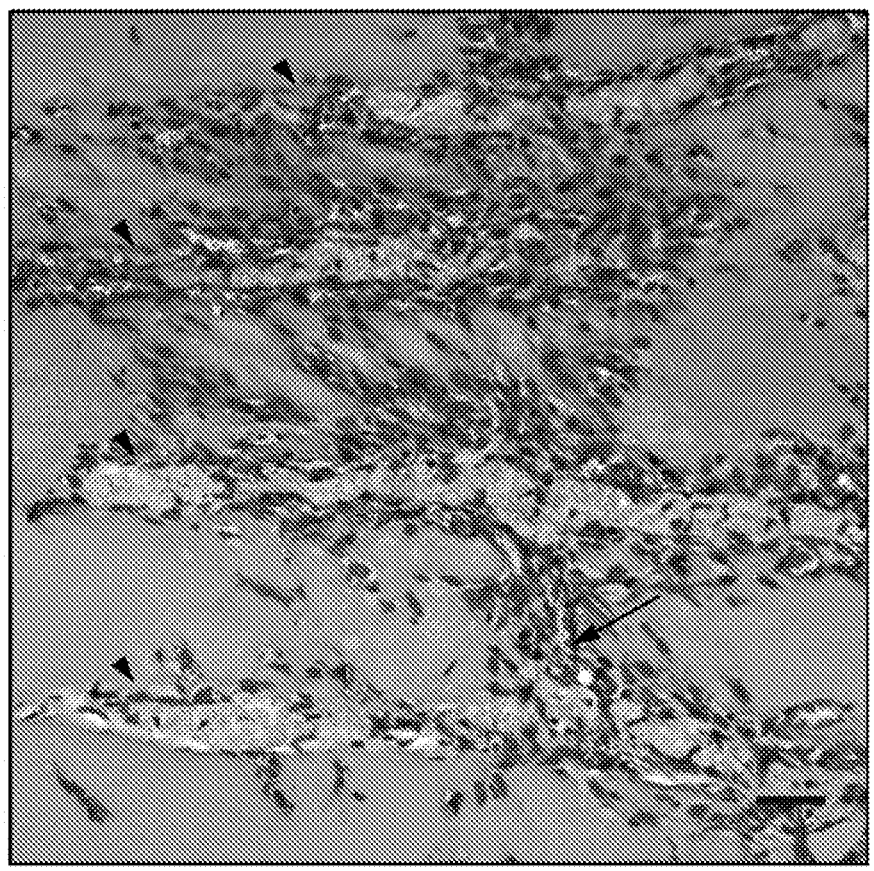
FIG. 13 shows evidence of sprouting between capillaries within adjacent cords. H&E staining of longitudinal cord cross-sections at day 7 PI revealed evidence of capillary sprouts (arrow) between adjacent cords (arrowheads) (bar, 25 µm).

Geometrically Defined EC Cords in Vitro Yield to Patterned, Perfused Vessels in Vivo After Implantation. To observe more convincingly whether these newly formed capillaries lining the cords had functionally anastomosed with the host vasculature and were perfused, injections of 150 kDa FITC-dextran via the tail vein at day 14 PI were performed and then the implant site was immediately imaged. FITC-dextran injections of control mice implanted with fibrin gels containing randomly seeded HUVECs and 10T1/2s resulted in random assembly of vessels exhibiting some degree of perfusion, but such perfusion was observed only near the periphery of implanted constructs (FIG. 9A, Left). Conversely, FITC-dextran injection of mice containing tissue constructs with cords demonstrated extensive perfusion of capillaries that spanned the entire length of the constructs. The dextran was contained exclusively within the intraluminal space of the neovessels, demonstrating that blood was not leaking into the interstitium. Importantly, the original network architecture of the cords visibly templated the new capillary vasculature. Constructs containing parallel arrays of cords resulted in a largely parallel capillary network, and introducing a single cord with a bifurcation resulted in a perfused branch point (FIG. 9A, Center and Right). For parallel cords, the resulting capillary network did not remain exclusively along the cords, as occasional sprouts containing blood extending between adjacent parallel cords were observed at day 14 (FIG. 9A, Center) and day 7 PI (FIG. 13).

Figure 9B:
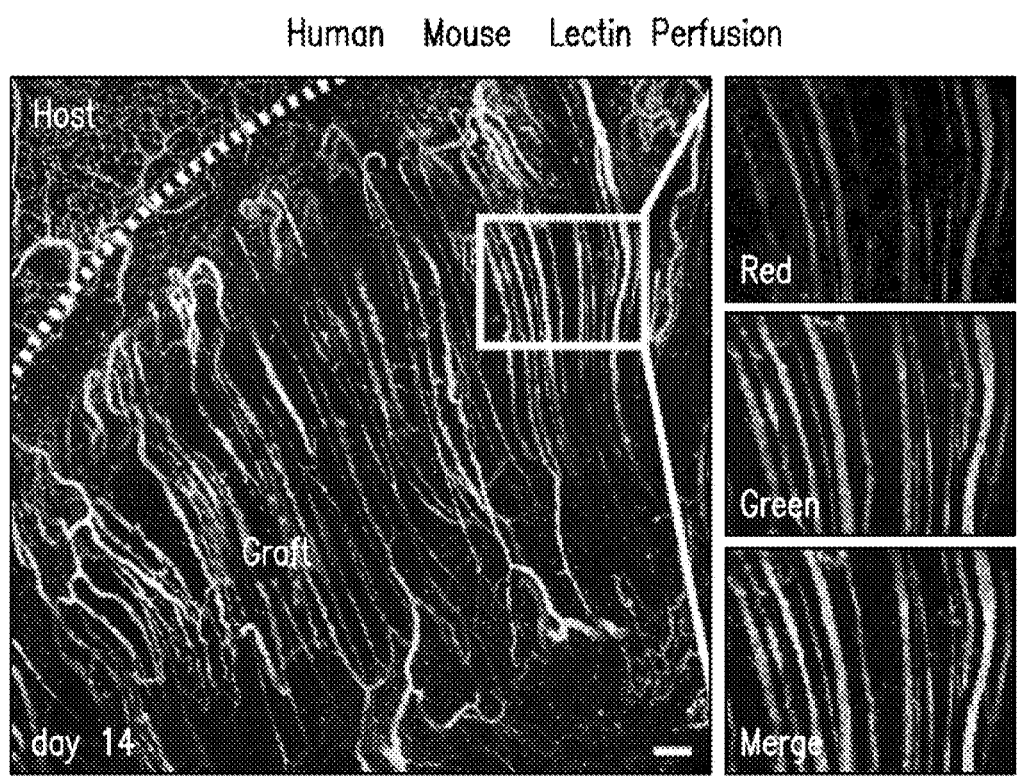
Figure 14:
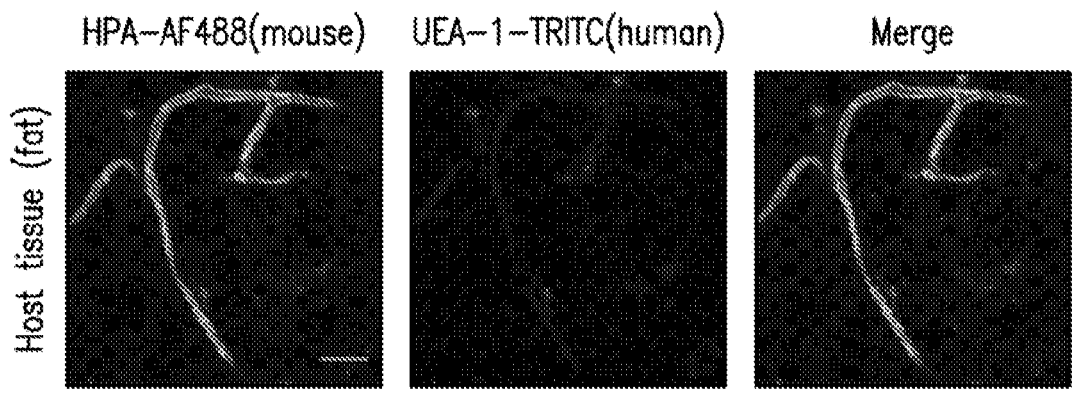
FIG. 14 shows mouse and human lectin cross-reactivity. Human-specific (UEA-1) lectin and mouse-specific (HPA) lectin were perfused at 14 d following implantation of constructs. Imaging of surrounding host adipose tissue demonstrated minimal cross-reactivity between UEA-1 and mouse vessels (bar, 25 µm).
Figure 15:
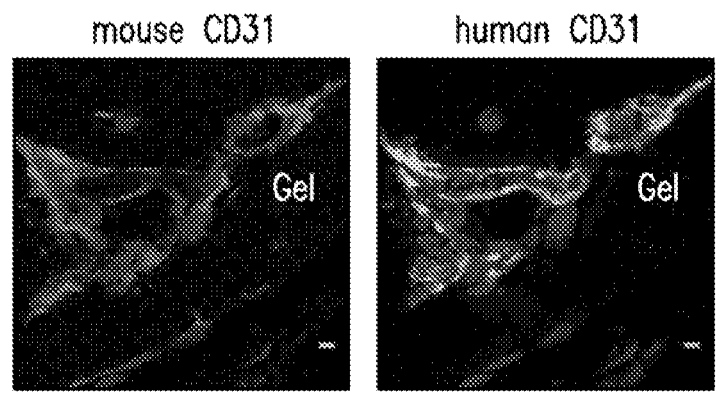
FIG. 15 illustrates the contribution of mouse vs. human endothelial cells to capillaries. Adjacent tissue sections were immunostained using antibodies specific for either mouse (Left) or human (Right) CD31. Capillaries in the grafts contained both human and mouse endothelium at 14 d PI (bar, 10 µm).

To determine the contribution of grafted and host ECs to the vascular interface of perfused capillaries, mouse- and human-specific lectins [Helix pomatia agglutinin (HPA)—Alexa Fluor 488 and Ulex europaeus agglutinin I (UEA-I)—TRITC, respectively] were injected via tail vein at day 14 PI and performed fluorescent imaging. Perfused microvascular networks in the graft area were composed of a parallel array of patent capillaries that appeared chimeric in composition (FIG. 9B). Stretches of capillaries that bound solely to UEA-1 or to HPA were visible throughout the constructs, suggesting that regions of perfused vessels were composed primarily of human or mouse ECs and confirmed previously reported species specificity of UEA-1 or HPA in the samples (22, 23). In addition, large stretches of capillaries colabeled with both lectins suggested chimeric composition of host and implanted cells in some vessels. Outside the boundary of the implant and cords, vessels were of mouse origin and individual vessels appeared to anastomose with multiple cord-associated capillaries. Imaging of host adipose tissue confirmed the lack of cross-reactivity between UEA-I and mouse vessels (FIG. 14). Further immunostaining using antibodies specific to mouse or human CD31 confirmed that both mouse and human ECs contributed extensively to capillaries in the graft (FIG. 15). These results demonstrate that geometrically controlled engineered vessels are perfused after implantation and that implanted cords anastomose with host tissue via a mechanism that involves, at least in part, ingrowth of host vessels into tissue constructs and connection to regions of vessels lined with a chimeric mixture of both graft- and host-derived endothelium.

Figure 10A:
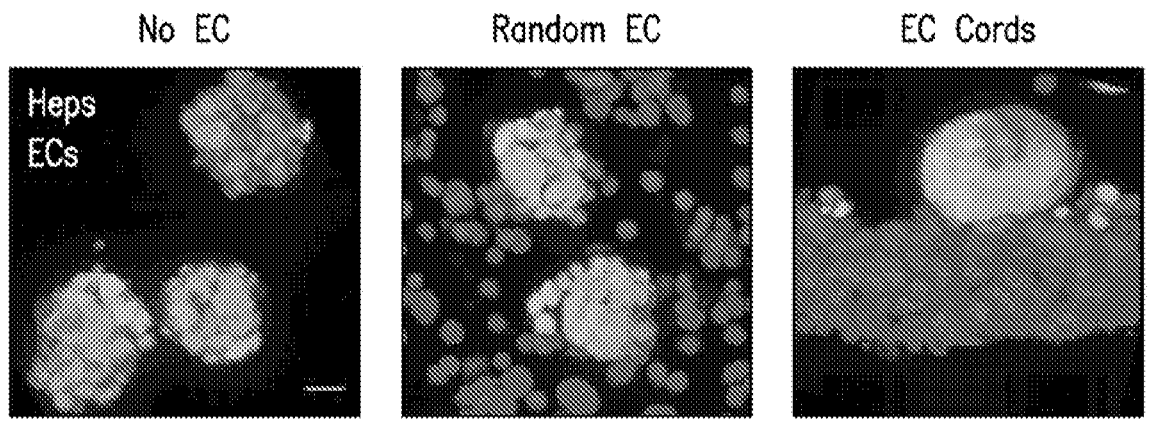
FIGS. 10A-10E show that EC cords within engineered hepatic tissue improve function.
Figure 10B:
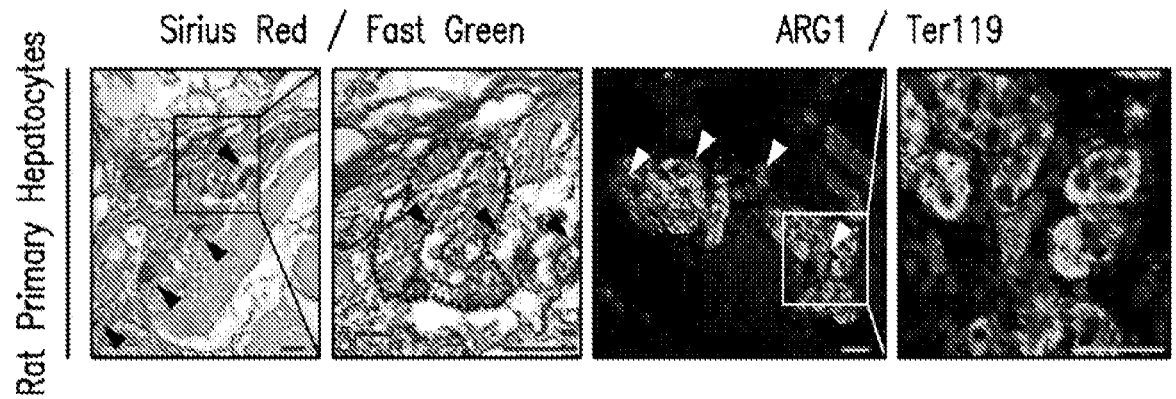
Figure 10C:
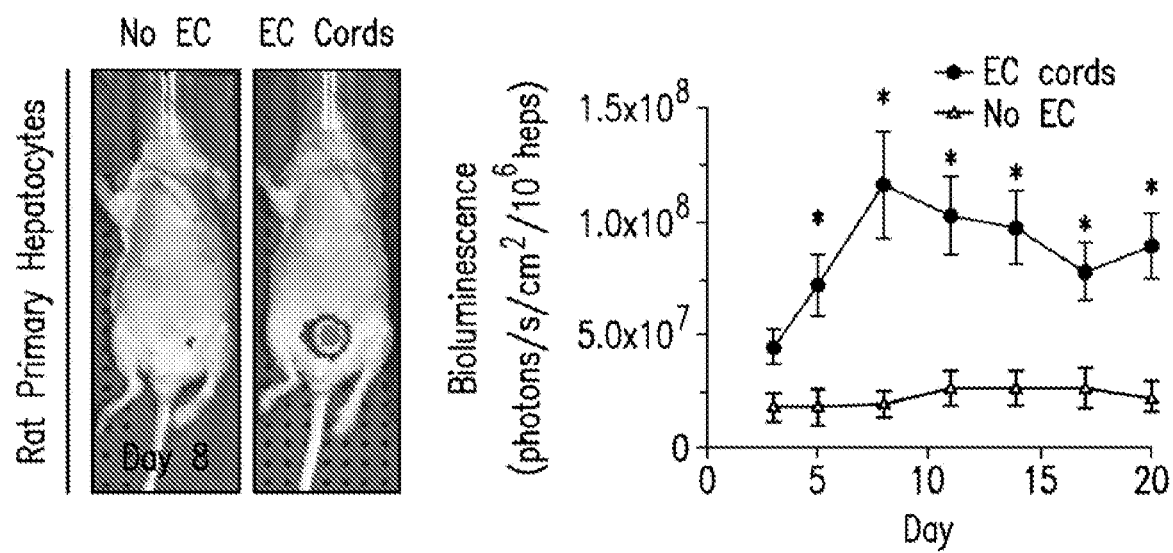

Spatially Patterned Endothelial Cords in Engineered Hepatic Tissues Improves Hepatocyte Function. Experiments were completed to determine whether geometrically controlled prevascularization of tissue constructs can affect parenchymal tissue survival and function (FIG. 4). Primary hepatocytes expressing luciferase under the control of a modified albumin promoter were aggregated into spheroids (FIG. 10A) to promote maintenance of their differentiated function (24, 25). To assess whether endothelial cords would support primary hepatocytes after implantation, tissue constructs containing rat hepatocyte aggregates and endothelial cords were sutured to the parametrial fat pad in athymic mice and were compared with control constructs containing rat hepatocyte aggregates only. Histological assessment of tissues explanted at day 20 revealed the presence of patterned collagen structures similar to those found in constructs with cords alone in earlier experiments (FIG. 10B, Left; black arrows). Collagen structures were closely associated with capillaries carrying fast-green-positive blood (FIG. 10B, white arrows) and cellular aggregates (FIG. 10B, dotted line). Immunofluorescent staining for RBCs and hepatocytes [Ter-119 and arginase 1 [ARG-1], respectively) suggested the presence of perfused neovessels directly adjacent to hepatocyte aggregates (FIG. 10B, Right). Hepatic tissues containing EC cords exhibited significantly greater albumin promoter activity for at least 20 d PI compared with tissues with no EC cords (FIG. 10C), suggesting a direct benefit from the cords.

Figure 10D:
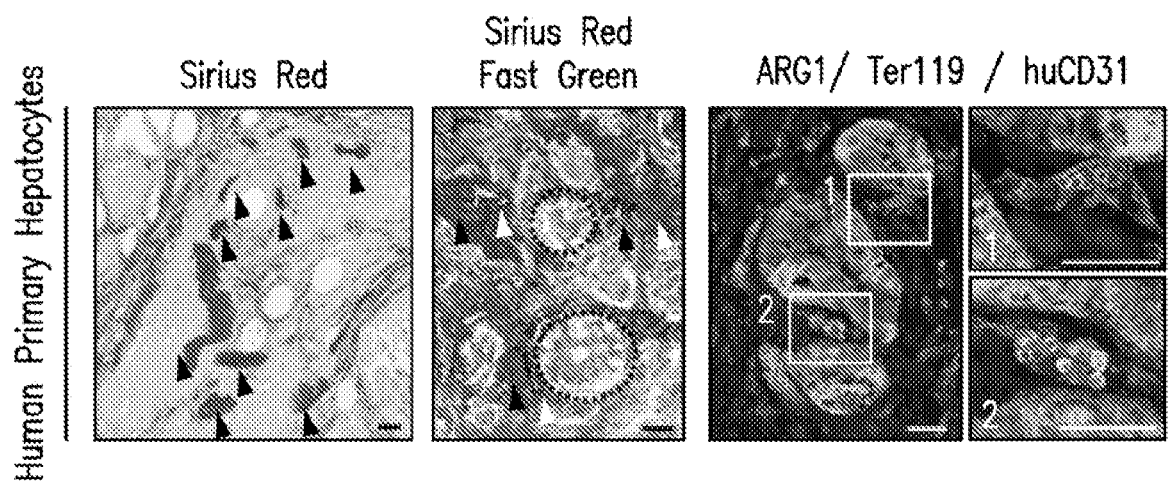
Figure 10E:
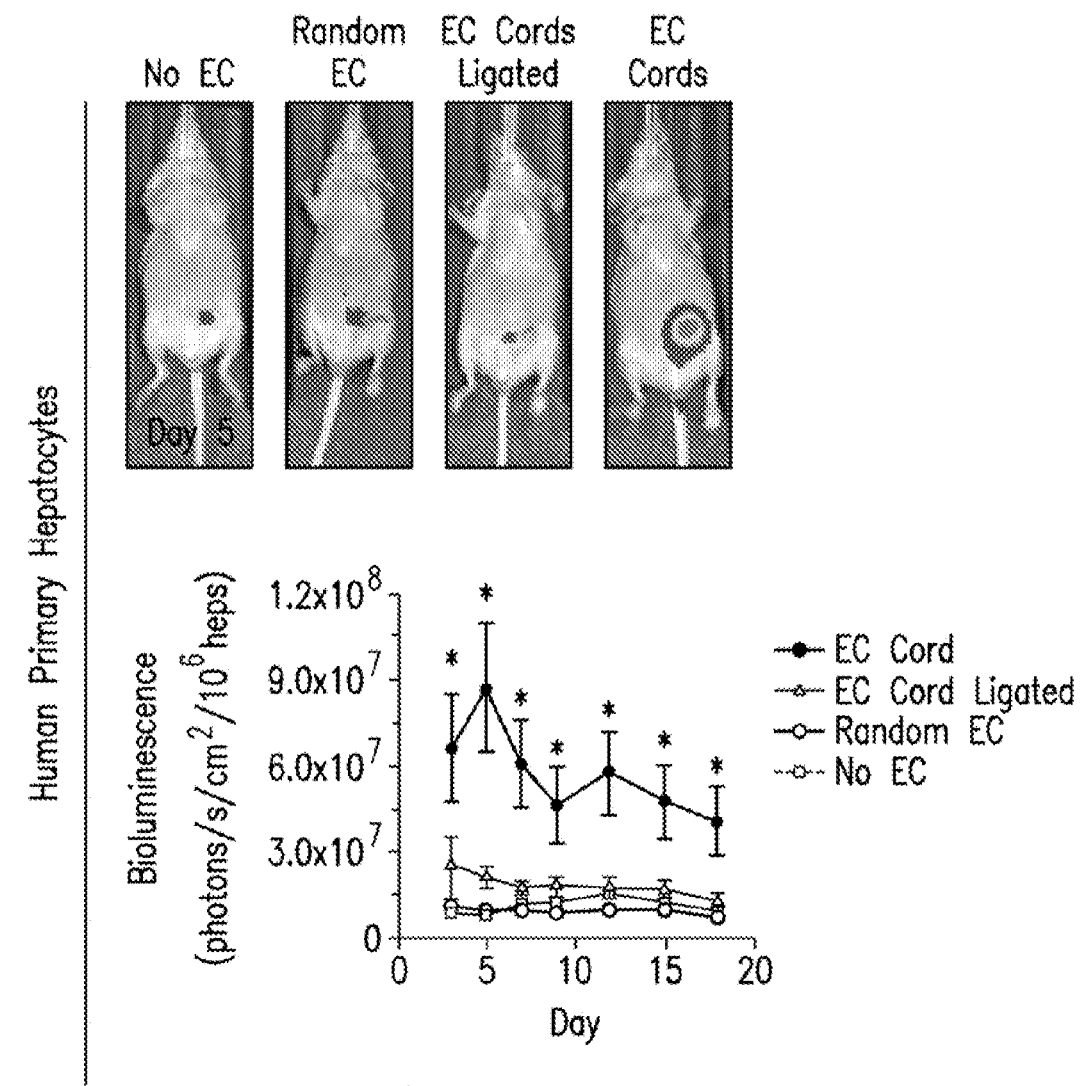
Figures 16A, 16B:
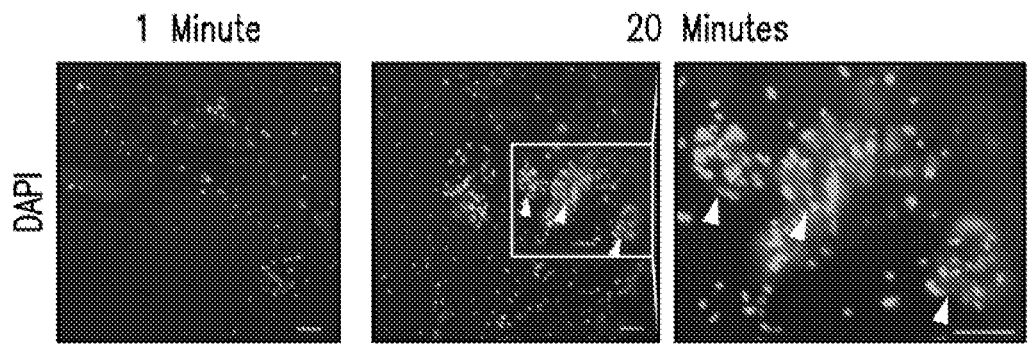
FIGS. 16A-16B show the diffusion of small-molecule DAPI through ligated constructs. Constructs containing both hepatic aggregates and cords were implanted using procedures identical to those of the "EC Cord Ligated" control. Following implantation, the animals were injected i.p. with DAPI using the same volume and concentration typically used for luciferin administration.

To explore whether this vascularization strategy has potential to enable applications such as human tissue replacement or humanized mouse models, it was tested whether coimplantation of EC cords can support primary human hepatocytes. Similar to constructs with rat hepatocytes and EC cords, constructs with human hepatocytes and EC cords exhibited Sirius red-positive collagen cores in graft areas (FIG. 10D, Left; black arrows). Further staining with both Sirius red and fast green suggested the presence of capillaries containing blood (white arrows) as well as cellular aggregates (dotted line) adjacent to collagen-rich cores (FIG. 10D, Center; black arrows). Importantly, triple immunostaining demonstrated that capillaries in the graft were lined with human endothelium (huCD31, red), contained erythrocytes (Ter-119, white), and were close to aggregates containing hepatocytes (ARG-1, green) (FIG. 10D, Right). Tissue constructs containing human hepatocyte aggregates and EC cords ("EC Cord") exhibited significantly higher levels of albumin promoter activity compared with both constructs without cords ("No EC") and constructs with randomly seeded endothelial and 10T1/2 cells ("Random EC"; FIG. 10E). To test whether enhanced hepatic function in animals with EC cords was the result of direct paracrine signaling between adjacent EC cords and hepatocytes or of improved access to a blood supply, the parametrial fat pad was severed upstream of the constructs immediately after implantation to reduce blood supply ("EC Cord Ligated"; FIG. 4E). Bioluminescence imaging was performed 20 min after luciferin injection at each time point, which was confirmed to be adequate time for diffusionbased permeation of the construct in ligated control tissues by DAPI (a small molecule similar in size to luciferin; FIG. 16). Poor functional performance of ligated control constructs suggested that enhanced hepatocyte activity in the presence of EC cords was a result of improved access to blood-carrying vasculature (FIG. 10E). These results show that geometric control of endothelial and mural cells during prevascularization of tissue constructs enhances vascular blood supply and improves survival and function of human hepatic tissue.

Discussion

Several recent studies have shown that combining randomly distributed ECs with supportive stromal cells provides a means to induce the formation of stable vasculature in a tissue engineered implant (26, 27, 28, 29, 30, 31). Allowing these cells to form interconnected networks in culture before implantation (prevascularization) appears to improve the rapidity and extent of the vascularization response (21, 32, 19, 33). The concept of prepatterning the cells using microfabrication approaches allows for the formation of reproducible, multicellular cords within hours. In contrast, culture of randomly distributed cells is typified by nonuniform rate, length, diameter, and orientation of tubule formation, and the resultant microvascular networks exhibit tortuous morphology and dense interconnectivity after implantation. Implantation of endothelial cords led to rapid anastomosis with the host vasculature (within 3 d), followed by the formation of large, nascent vessels that later reorganized into smaller, more numerous capillaries composed, at least in part, of implanted ECs. These data show, viable cells within cords were required for and contributed directly to the vascularization response. These results correspond with previous studies in which randomly distributed cells within implanted constructs contributed directly to the formation of vessels (24, 20, 27, 31). Additionally, studies have shown that implanted ECs anastomose by migrating toward and tapping into existing host vasculature (26, 34, 35, 36). Capillaries within implanted cords, however, seemed to exhibit a chimeric phenotype, suggesting that directed angiogenic sprouting of the host vasculature occurred during anastomosis. Not limited to a particular theory, the vascularization response observed upon implantation of EC cords is likely driven by a mechanism involving both angiogenesis, which promotes sprouting from the host vasculature, and vasculogenesis, which promotes the assembly of capillaries from implanted cells.

Patterning vascular architecture remains a key challenge in engineering complex, metabolically active tissues such as kidney and liver (27, 33, 41, 37, 42 23). Previously, physical and biochemical means have been used to spatially guide the host angiogenic response in tissue engineered constructs (37, 28, 38, 29, 30, 39, 40). Although these approaches rely on the relatively slow ingrowth of vessels from host tissue, the implanted EC cords described herein appear to act as a guide for a rapid vascularization response that results in nearly complete and templated perfusion of all cords throughout the construct. Importantly, the parallel capillary network formed in these studies is highly organized compared with the networks created by prevascularization via random cell seeding and self organization, which are characterized by tortuous morphology and dense interconnectivity. Indeed, a recent study demonstrated that although such randomly organized networks initially connect rapidly to host vessels, perfusion is lost after 5 d by thrombus formation secondary to low shear rates in these highly irregular networks (43). This finding is in sharp contrast to the response of architectural arrays of largely parallel capillaries, which remain patent and perfused at least 2 wk after implantation. These results suggest that the caliber, tortuosity, and interconnectivity of the endothelial networks can play a major role in the vascularization process. This hypothesis is supported by mathematical models, in which the architecture of mature capillary beds has been predicted to affect blood flow and nutrient delivery (44, 45). The ability to control vascular architecture using methods demonstrated herein will enable studies of the effects of vascular features such as vessel density, alignment, and branching on tissue oxygenation and function and will inform the generation of custom tissue-specific vascular architectures.

Intricate interactions among hepatocytes, ECs, and other nonparenchymal cell populations are critical for efficient macromolecular and drug transport as well as response to regenerative cues in the liver. For example, hypoxic hepatocytes express angiogenic factors that recruit ECs (and other nonparenchymal cells) in liver injury and repair, and liver sinusoidal ECs secrete "angiocrine" signals that mediate liver regeneration (46, 47). Furthermore, the 3D spatial arrangement of these cells is tightly regulated in development, has been suggested to at least partially coordinate regeneration, and is dysfunctional in pathological states such as cirrhosis (48). Although models have been developed to "prevascularize" engineered hepatic and hepatoma tissue using ECs in vitro (49, 50), the fate of prevascularized constructs after in vivo implantation had not been documented before. In the present disclosure it has been determined that implantation of engineered tissue containing primary hepatocytes and geometrically defined endothelial cords stabilized by stromal cells augments hepatic albumin activity following transplantation. Importantly, vessel organization and perfusion with blood were both critical to functional benefit, as this effect was not seen in constructs containing randomly seeded ECs or with cords lacking a blood supply. Thus, by improving tissue perfusion through the geometric control over implanted cells, this disclosure provides a strategy to enable improved tissue integration function due to enhanced blood supply.

Example 5: Endothelial Cells are Necessary for Vascularization Response In Vivo

Figure 17A:
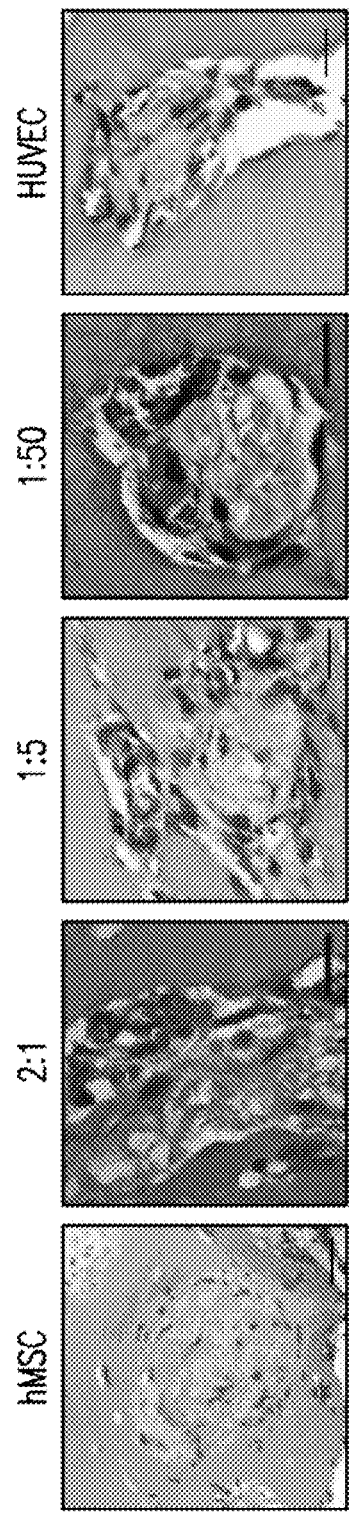
FIGS. 17A-17C show that endothelial cells are necessary for vascularization in vivo.
Figure 17B:
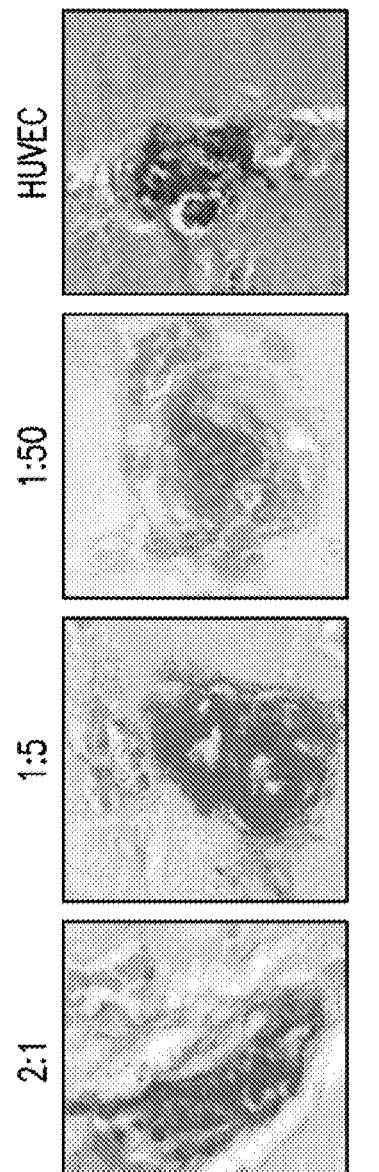
Figure 17C:
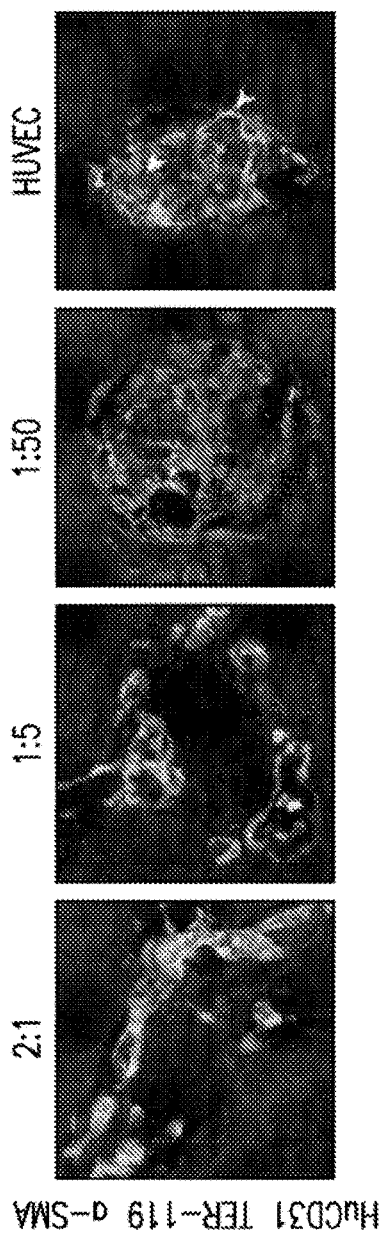
Figure 17C:
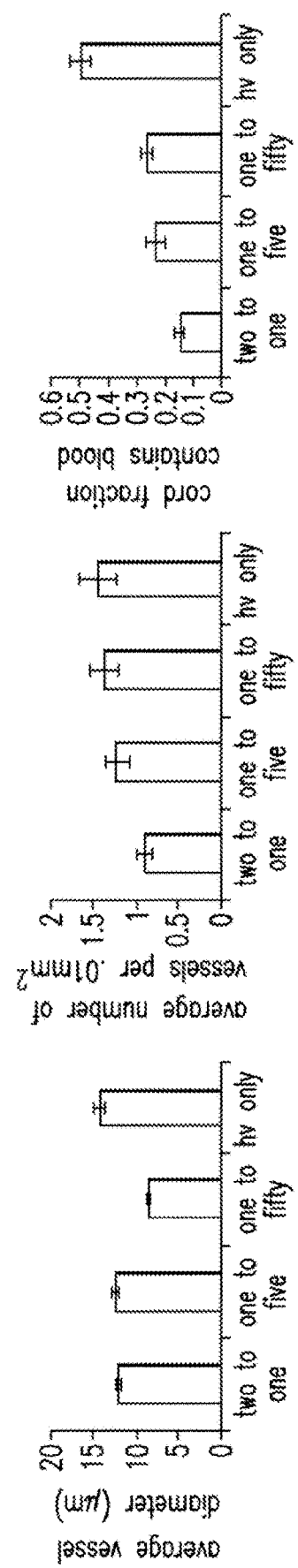

To test whether endothelial cells are necessary for a vascularization response in vivo, various concentrations of Human Umbilical Vein Endothelial Cells (HUVECs) were co-cultured with human mesenchymal stem cell (hMSC). No vessels or blood were observed in the hMSC only condition (FIG. 17A). All other conditions containing 10T1/2s cocultured with HUVECs at various ratios (2:1, 1:5, 1:50, and 0:1 (HUVEC only)) induce a vascularization response in vivo as capillaries containing blood are evident around the periphery of the cord (FIG. 17A). Immunohistochemistry confirms the presence of human CD31 positive capillaries surrounding ter-119 positive erythrocytes (FIG. 17B). All capillaries are surrounded by alpha smooth muscle actin (FIG. 17C). There is no evident difference in average vessel diameter of the neovessels between different co-culture ratios (FIG. 17). However, the average number of vessels increases slightly with increasing HUVEC ratio. Significantly, the cord fraction containing blood is significantly higher in the HUVEC only condition. This suggests that co-culturing ECs with pericyte like cells within the cords is not necessary to induce a robust vascular response. Furthermore, the HUVEC only condition is a human cell only condition, allowing for a completely humanized graft for clinical and translational purposes.

Example 6: Cord Diameter can be Varied and Still Promote Vessel Formation

Figure 18A:
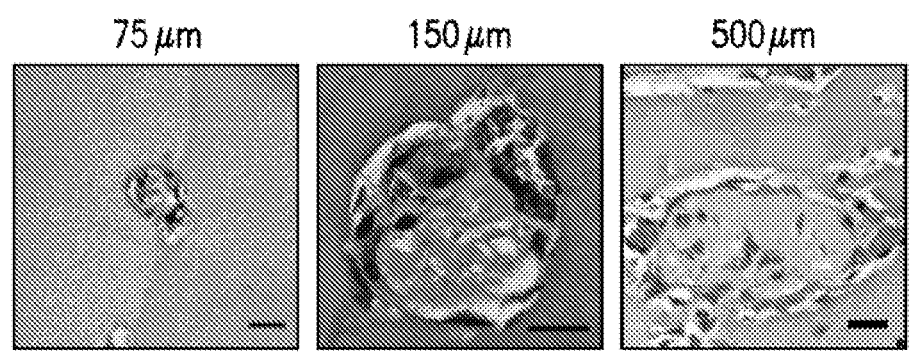
Figure 18B:
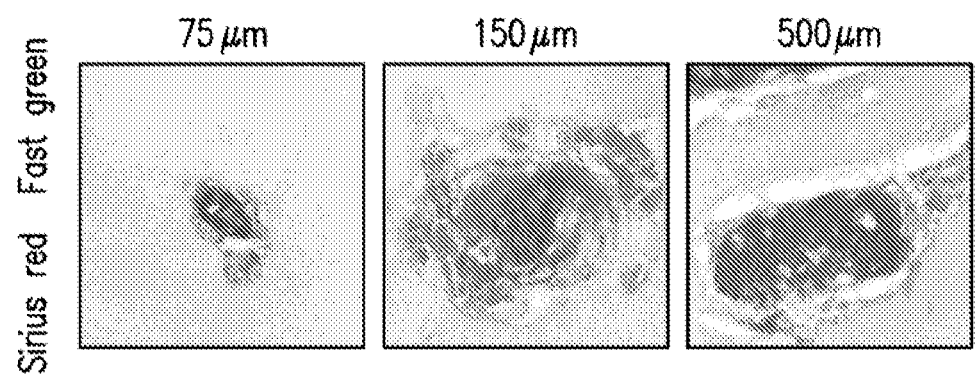

Cord diameter can be varied for tissue engineering applications. Cord diameters between 75 and 500 µm all result in a vascular response in vivo (FIG. 18A). Immunohistochemistry confirms the presence of human CD31 positive capillaries surrounding ter-119 positive erythrocytes (FIG. 18B). All capillaries are surrounded by alpha smooth muscle actin (FIG. 18C). There is no evident difference in average vessel diameter of the neovessels between different co-culture ratios. However, the 500 µm cords resulted in fewer larger vessels than the small cord diameters. Since capillaries form along the circumference of the cord, the surface area of contact between the resulting vessels and future parenchymal cell type can be varied using cord diameter to suit tissue specific needs.

Example 7: Additional Method to Form Patterned Biomaterial

A feature of the patterned biomaterial of the present disclosure is the fabrication process that allows micro-scale patterning of cells into cords with pre-specified network architectures that allows easy, reproducible assembly of these biomaterials into a final product even in the operating room. This technology involves printing of a sacrificial cytocompatible material recently described in Nature Materials (57).

To fabricate the vascular networks, sacrificial filaments of carbohydrate glass material were 3D printed. This unique 3D printing technology was used to generate filaments with specified diameters (25 to 500 um) and spacings with micrometer resolution, spanning centimeter length, and with specified branchpoints (bifurcations). The free-standing filament networks are then encapsulated in an extracellular matrix (ECM) casing, followed by filament dissolution (FIG. 20). Seeding endothelial cells into the channels with additional ECM results in spatially organized networks of EC cords, with pre-specified alignment, branching, and density. Implantation results in remarkably rapid (days) guidance of host revascularization to produce functional vasculature in the programmed architecture.

To extend the zone of perfusion for a vascular bed, the patterned biomaterial was designed to contain a high density of cell-containing cords aligned in parallel (FIG. 21A). To test the ability of patterned biomaterial to direct host revascularization, the patterned biomaterial was first implanted subcutaneously and in the peritoneal fat pad, both of which resulted in similar responses. These results demonstrated that the pre-existing vascular networks in the patterned biomaterial led to anastomosis and integration of the constructs by host tissues. The parallel cords in the patterned biomaterial triggered the host vasculature to invade and guide new vessel formation along the channels, such that systemically injected fluorescent dextran appeared immediately in the parallel array of host vessels that had formed within these constructs, indicating perfusion within these new blood vessels (FIG. 21B). Remarkably, this vascularization response occurred within five days post-implantation in vivo. This is unexpectedly and significantly faster than state-of-the-art control constructs (where cells are randomly seeded and distributed throughout the construct, or where growth factors are delivered within the implant), which typically take 7-28 days to become perfused (33). In fact, in side-by-side controlled comparisons, delayed vascularization was observed not only in the unpatterned constructs, but perfusion is limited only to the peripheral millimeter of the implant, and would not be useful for directing vascularization to new unperfused territories.

Histologic analysis of these neovessels notably demonstrated a highly geometrically regular array of vessels coursing throughout the implant, with the diameter of the neovessels and spacing between the vessels that matched the geometry of the implanted patterned biomaterial network (FIG. 21C, D). Notably the new vessels contained blood, were lined with an endothelium reminiscent of native host vessels, and the large caliber of these vessels which carry substantially more blood flow than capillaries has not been described to the best of our knowledge in any other revascularization product.

Utilizing the patterned biomaterial construct for enhancing new regions of blood flow is especially novel because of the unexpected finding that pre-organizing the implanted network of cords can enhance the extent of vascularization as well as influence the caliber of vessels and network topology. While cells randomly seeded into gels can also enhance vascularization, the patterned cords employed within the patterned biomaterial appear to mirror the architectural component of host vessel formation, thus enhancing graft vascularization in a way previously not possible, demonstrated, or articulated.

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure.

REFERENCES

1. Mooney, D. J. and A. G. Mikos, Growing new organs. Scientific American, 1999. 280(4): p. 60-65.
2. Raghavan, S., et al., Geometrically Controlled Endothelial Tubulogenesis in Micropatterned Gels. Tissue Engineering Part A, 2010. 16(7): p. 2255-2263.
3. Database, U., National Organ transplant waiting list report, US Department of Health and Human Services.
4. Vacanti, J. P. and R. Langer, Tissue engineering: the design and fabrication of living replacement devices for surgical reconstruction and transplantation. Lancet, 1999. 354: p. Si32-Si34.

5. Jain, R. K., Transport of Molecules, Particles, and Cells in Solid Tumors. Annual Reviews in Biomedical Engineering, 1999.
6. Chen, X. F., et al., Rapid Anastomosis of Endothelial Progenitor Cell-Derived Vessels with Host Vasculature Is Promoted by a High Density of Cotransplanted Fibroblasts. Tissue Engineering Part A, 2010. 16(2): p. 585-594.
7. Levenberg, S., et al., Engineering vascularized skeletal muscle tissue. Nature Biotechnology, 2005. 23(7): p. 879-884.
8. Au, P., et al., Bone marrow-derived mesenchymal stem cells facilitate engineering of long-lasting functional vasculature. Blood, 2008. 111(9): p. 4551-4558.
9. Chen, X. F., et al., Prevascularization of a Fibrin-Based Tissue Construct Accelerates the Formation of Functional Anastomosis with Host Vasculature. Tissue Engineering Part A, 2009. 15(6): p. 1363-1371.
10. Gjorevski, N. and C. M. Nelson, Endogenous patterns of mechanical stress are required for branching morphogenesis. Integrative Biology, 2010. 2(9): p. 424-434.
11. Phelps, E. A. and A. J. Garcia, Engineering more than a cell: vascularization strategies in tissue engineering. Current Opinion in Biotechnology, 2010. 21(5): p. 704-709.
12. Lovett, M., et al., Vascularization Strategies for Tissue Engineering. Tissue Engineering Part B-Reviews, 2009. 15(3): p. 353-370.
13. Traktuev, D. O., et al., Robust Functional Vascular Network Formation In Vivo by Cooperation of Adipose Progenitor and Endothelial Cells. Circulation Research, 2009. 104(12): p. 1410-U320.
14. Weber, L. M., K. N. Hayda, and K. S. Anseth, Cell-Matrix Interactions Improve beta-Cell Survival and Insulin Secretion in Three-Dimensional Culture. Tissue Engineering Part A, 2008. 14(12): p. 1959-1968.
15. Nikolova, G., et al., The vascular basement membrane: A niche for insulin gene expression and beta cell proliferation. Developmental Cell, 2006. 10(3): p. 397-405.
16. Harding, M. J., et al., An Implantable Vascularized Protein Gel Construct That Supports Human Fetal Hepatoblast Survival and Infection by Hepatitis C Virus in Mice. Plos One, 2010. 5(3).
17. Smith, M. K., et al., Locally enhanced angiogenesis promotes transplanted cell survival. Tissue Engineering, 2004. 10(1-2): p. 63-71.
18. Roh, J. D., et al., Tissue-engineered vascular grafts transform into mature blood vessels via an inflammation-mediated process of vascular remodeling. Proceedings of the National Academy of Sciences of the United States of America, 2010. 107(10): p. 4669-4674.
19. Radisic M, et al. (2003) High-density seeding of myocyte cells for cardiac tissue engineering. Biotechnol Bioeng 82(4):403-414.
20. Reid L M, Fiorino A S, Sigal S H, Brill S, Holst P A (1992) Extracellular matrix gradients in the space of Disse: Relevance to liver biology. Hepatology 15(6): 1198-1203.
21. Vacanti J P, Langer R (1999) Tissue engineering: The design and fabrication of living replacement devices for surgical reconstruction and transplantation. Lancet 354 (Suppl 1):SI32-SI34.
22. Debbage P L, et al. (2001) Intravital lectin perfusion analysis of vascular permeability in human micro- and macro-blood vessels. Histochem Cell Biol 116(4):349-359.
23. Debbage P L, et al. (1998) Lectin intravital perfusion studies in tumor-bearing mice: Micrometer-resolution, wide-area mapping of microvascular labeling, distinguishing efficiently and inefficiently perfused microregions in the tumor. J Histochem Cytochem 46(5):627-639.
24. Lovett M, Lee K, Edwards A, Kaplan D L (2009) Vascularization strategies for tissue engineering. Tissue Eng Part B Rev 15(3):353-370.
25. Brophy C M, et al. (2009) Rat hepatocyte spheroids formed by rocked technique maintain differentiated hepatocyte gene expression and function. Hepatology 49(2): 578-586.
26. Jain R K (1999) Transport of molecules, particles, and cells in solid tumors. Annu Rev Biomed Eng 1:241-263.
27. Koike N, et al. (2004) Tissue engineering: Creation of long-lasting blood vessels. Nature 428(6979):138-139.
28. Levenberg S, et al. (2005) Engineering vascularized skeletal muscle tissue. Nat Biotechnol 23(7):879-884.
29. Koffler J, et al. (2011) Improved vascular organization enhances functional integration of engineered skeletal muscle grafts. Proc Natl Acad Sci USA 108(36): 14789-14794.
30. Stevens K R, et al. (2009) Physiological function and transplantation of scaffold free and vascularized human cardiac muscle tissue. Proc Natl Acad Sci USA 106 (39):16568-16573.
31. Chen X, et al. (2010) Rapid anastomosis of endothelial progenitor cell-derived vessels with host vasculature is promoted by a high density of cotransplanted fibroblasts. Tissue Eng Part A 16(2):585-594.
32. Folkman J (2002) Looking for a good endothelial address. Cancer Cell 1(2):113-115.
33. Chen X, et al. (2009) Prevascularization of a fibrin-based tissue construct accelerates the formation of functional anastomosis with host vasculature. Tissue Eng Part A 15(6):1363-1371.
34. Richardson T P, Peters M C, Ennett A B, Mooney D J (2001) Polymeric system for dual growth factor delivery. Nat Biotechnol 19(11):1029-1034.
35. Lee K Y, Peters M C, Anderson K W, Mooney D J (2000) Controlled growth factor release from synthetic extracellular matrices. Nature 408(6815):998-1000.
36. Cheng G, et al. (2011) Engineered blood vessel networks connect to host vasculature via wrapping-and-tapping anastomosis. Blood 118(17):4740-4749.
37. Kang K-T, Allen P, Bischoff J (2011) Bioengineered human vascular networks transplanted into secondary mice reconnect with the host vasculature and re-establish perfusion. Blood 118(25):6718-6721.
38. Kaufman-Francis K, Koffler J, Weinberg N, Dor Y, Levenberg S (2012) Engineered vascular beds provide key signals to pancreatic hormone-producing cells. PLoS One 7(7):e40741.
39. Chen R R, Silva E A, Yuen W W, Mooney D J (2007) Spatio-temporal VEGF and PDGF delivery patterns blood vessel formation and maturation. Pharm Res 24(2):258-264.
40. Jeong J H, et al. (2012) "Living" microvascular stamp for patterning of functional neovessels; orchestrated control of matrix property and geometry. Adv Mater (Deerfield Beach Fla) 24(1):58-63, 1.
41. Melero-Martin J M, et al. (2008) Engineering robust and functional vascular networks in vivo with human adult and cord blood-derived progenitor cells. Circ Res 103(2): 194-202.
42. Vacanti J P (2012) Tissue engineering and the road to whole organs. Br J Surg 99(4): 451-453.

43. White S M, et al. (2012) Longitudinal in vivo imaging to assess blood flow and oxygenation in implantable engineered tissues. Tissue Eng Part C Methods 18(9):697-709.
44. Intaglietta M, Johnson P C, Winslow R M (1996) Microvascular and tissue oxygen distribution. Cardiovasc Res 32(4):632-643.
45. Pittman R N (1995) Influence of microvascular architecture on oxygen exchange in skeletal muscle. Microcirculation 2(1):1-18.
46. Rosmorduc O, Housset C (2010) Hypoxia: A link between fibrogenesis, angiogenesis, and carcinogenesis in liver disease. Semin Liver Dis 30(3):258-270.
47. Ding B-S, et al. (2010) Inductive angiocrine signals from sinusoidal endothelium are required for liver regeneration. Nature 468(7321):310-315.
48. Matsumoto K, Yoshitomi H, Rossant J, Zaret K S (2001) Liver organogenesis promoted by endothelial cells prior to vascular function. Science 294(5542):559-563.
49. McGuigan A P, Sefton M V (2006) Vascularized organoid engineered by modular assembly enables blood perfusion. Proc Natl Acad Sci USA 103(31):11461-11466.
50. Nahmias Y, Berthiaume F, Yarmush M L (2007) Integration of technologies for hepatic tissue engineering. Adv Biochem Eng Biotechnol 103:309-329.
51. March S, Hui E E, Underhill G H, Khetani S, Bhatia S N (2009) Microenvironmental regulation of the sinusoidal endothelial cell phenotype in vitro. Hepatology 50(3): 920-928.
52. Chen A A, et al. (2011) Humanized mice with ectopic artificial liver tissues. Proc Natl Acad Sci USA 108(29): 11842-11847.
53. Seglen P O (1976) Preparation of isolated rat liver cells. Methods Cell Biol 13:29-83.
54. Dunn J C, Tompkins R G, Yarmush M L (1991) Long-term in vitro function of adult hepatocytes in a collagen sandwich configuration. Biotechnol Prog 7(3): 237-245.
55. Debbage P L, et al. (2001) Intravital lectin perfusion analysis of vascular permeability in human micro- and macro-blood vessels. Histochem Cell Biol 116(4):349-359.
56. Debbage P L, et al. (1998) Lectin intravital perfusion studies in tumor-bearing mice: Micrometer-resolution, wide-area mapping of microvascular labeling, distinguishing efficiently and inefficiently perfused microregions in the tumor. J Histochem Cytochem 46(5):627-639.
57. Miller, J. S., Stevens, K. R., Yang, M. T., Baker, B. M., Nguyen, D. H., et al. (2012). Rapid casting of patterned vascular networks for perfusable engineered three-dimensional tissues. Nat Mater.

Various publications, patents and patent applications are cited herein, the contents of which are hereby incorporated by reference herein in their entireties.

The invention claimed is:

1. A method of promoting vascularization of a patterned biomaterial implanted in a subject, the method comprising:
   (a) organizing endothelial cells in micropatterns in a culture, thereby forming one or more endothelial cell cords from the endothelial cells;
   (b) at least partially embedding the one or more endothelial cell cords in a scaffolding, thereby forming a patterned biomaterial containing one or more endothelial cell cords; and
   (c) implanting the patterned biomaterial into the subject, wherein the patterned biomaterial is configured to promote the vascularization of the patterned biomaterial, and wherein the structure of the patterned biomaterial has a pre-specified architecture that acts as a template and spatial guidance for the subject's vasculature, such that the subject's vasculature invades and integrates at least partially within the one or more endothelial cell cords.

2. The method of claim 1, wherein organizing endothelial cells in micropatterns in a culture in step (a) comprises suspending cells in a liquid collagen.

3. The method of claim 1, wherein the scaffolding is a naturally-derived scaffolding.

4. The method of claim 1, wherein the scaffolding is a synthetic scaffolding.

5. The method of claim 1, wherein the scaffolding comprises collagen.

6. The method of claim 1, wherein the scaffolding comprises fibrin.

7. The method of claim 1, wherein the one or more endothelial cells cords are branched.

8. The method of claim 1, wherein the one or more endothelial cell cords are formed in a parallel arrangement within the scaffolding.

9. The method of claim 1, wherein the one or more endothelial cell cords are formed in a nonparallel arrangement within the scaffolding.

10. The method of claim 1, wherein the one or more endothelial cell cords are cylindrical, Y-shaped or T-shaped.

11. The method of claim 1, wherein the one or more endothelial cells cords are solid or hollow in cross-section.

12. A method of promoting vascularization of a patterned biomaterial implanted in a subject, the method comprising:
    (a) providing a patterned biomaterial comprising at least one endothelial cell cord, formed by embedding cells in a naturally-derived or synthetic scaffolding with a pre-specified architecture and spatially organizing the cells within the scaffolding; and
    (b) implanting the patterned biomaterial into the subject, wherein the patterned biomaterial is configured to promote the vascularization of the patterned biomaterial, and wherein the structure of the patterned biomaterial has a pre-specified architecture that acts as a template and spatial guidance for the subject's vasculature, such that the subject's vasculature invades and integrates at least partially within the at least one endothelial cell cord.

13. The method of claim 12, wherein spatially organizing the cells within the scaffolding in step (a) comprises suspending cells in a liquid collagen.

14. The method of claim 12, wherein the scaffolding comprises collagen.

15. The method of claim 12, wherein the scaffolding comprises fibrin.

16. The method of claim 12, wherein the at least one endothelial cell cord is branched.

17. The method of claim 12, wherein the at least one endothelial cell cord is formed in a parallel arrangement within the scaffolding.

18. The method of claim 12, wherein the at least one endothelial cell cord is formed in a nonparallel arrangement within the scaffolding.

19. The method of claim 12, wherein the at least one endothelial cell cord is cylindrical, Y-shaped or T-shaped.

20. The method of claim 12, wherein the at least one endothelial cell cord is solid or hollow in cross-section.

* * * * *